(12) United States Patent
Demont et al.

(10) Patent No.: US 8,222,245 B2
(45) Date of Patent: *Jul. 17, 2012

(54) OXADIAZOLE DERIVATIVES ACTIVE ON SPHINGOSINE-1-PHOSPHATE (S1P)

(75) Inventors: Emmanuel Hubert Demont, Stevenage (GB); Jag Paul Heer, Harlow (GB); John Skidmore, Harlow (GB); Ian David Wall, Harlow (GB); Jason Witherington, Stevenage (GB); Thomas Daniel Heightman, Harlow (GB); David Nigel Hurst, Harlow (GB); Christopher Norbert Johnson, Harlow (GB)

(73) Assignee: Glaxo Group Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/747,205

(22) PCT Filed: Dec. 19, 2008

(86) PCT No.: PCT/EP2008/067965
§ 371 (c)(1),
(2), (4) Date: Jun. 10, 2010

(87) PCT Pub. No.: WO2009/080725
PCT Pub. Date: Jul. 2, 2009

(65) Prior Publication Data
US 2010/0273771 A1    Oct. 28, 2010

(30) Foreign Application Priority Data

Dec. 21, 2007 (GB) .................................. 0725120.0
Dec. 1, 2008 (GB) .................................. 0821918.0

(51) Int. Cl.
| A61P 17/00 | (2006.01) |
| A61P 37/00 | (2006.01) |
| A61K 31/55 | (2006.01) |
| C07D 223/16 | (2006.01) |
| C07D 267/14 | (2006.01) |
| C07D 271/06 | (2006.01) |
| C07D 413/04 | (2006.01) |
| C07D 413/14 | (2006.01) |

(52) U.S. Cl. .................................. 514/211.09; 540/552
(58) Field of Classification Search ............ 514/211.09; 540/552
See application file for complete search history.

(56) References Cited

FOREIGN PATENT DOCUMENTS

| EP | 1760071 A | 3/2007 |
| EP | 1826197 A | 8/2007 |
| EP | 2003132 A | 12/2008 |
| WO | WO 2004/113330 | 12/2004 |
| WO | WO 2005/058848 | 6/2005 |
| WO | WO 2006/047195 | 5/2006 |
| WO | WO 2007/116866 | 10/2007 |
| WO | WO 2008/064337 | 5/2008 |
| WO | WO 2009/080724 | 7/2009 |
| WO | WO 2009/080728 | 7/2009 |
| WO | WO 2009/080729 | 7/2009 |
| WO | WO 2009/080730 | 7/2009 |

OTHER PUBLICATIONS

Nigel Cooke, et al: "Sphingosine 1-Phosphate Type 1 Receptor Modulators: Recent Advances and Therapeutic Potential" Annual Reports in Medicinal Chemistry, San Diego, US, vol. 42, Jan. 1, 2007, pp. 245-263, XP008102308; ISSN: 0065-7743.

Vachal Petr et al.: "Highly selective and potent agonists of sphingosine-1-phosphate 1 (S1P1) receptor." Bioorganic & Medicinal Chemistry Letters, Jul. 15, 2006, vol. 16, No. 14, Jul. 15, 2006 pp. 3684-3687 ISSN: 0960-894X.

Yan Lin, et al.: "SAR studies of 3-arylpropionic acids as potent and selective agonists of sphingosine-1-phosphate receptor-1 (S1P1) with enhanced pharmacokinetic properties." Bioorganic & Medicinal Chemistry Letters Feb. 1, 2007, vol. 17 No. 3. Feb. 1, 2007, pp. 828-831; ISSN: 0960-894X.

*Primary Examiner* — Brenda Coleman
(74) *Attorney, Agent, or Firm* — Linda E. Hall; John L. Lemanowicz

(57) ABSTRACT

The present invention relates to novel oxadiazole derivatives having pharmacological activity, processes for their preparation, pharmaceutical compositions containing them and their use in the treatment of various disorders.

5 Claims, No Drawings

OXADIAZOLE DERIVATIVES ACTIVE ON SPHINGOSINE-1-PHOSPHATE (S1P)

This application is a 371 of International Application No. PCT/EP2008/067965, filed 19 Dec. 2008, which claims the priority of GB Application No. GB 0821918.0 filed 1 Dec. 2008 and GB Application No. GB 0725120.0 filed 21 Dec. 2007, which are incorporated herein in their entirety.

The present invention relates to novel oxadiazole derivatives having pharmacological activity, processes for their preparation, pharmaceutical compositions containing them and their use in the treatment of various disorders.

Sphingosine 1-phosphate (S1P) is a bioactive lipid mediator formed by the phosphorylation of sphingosine by sphingosine kinases and is found in high levels in the blood. It is produced and secreted by a number of cell types, including those of hematopoietic origin such as platelets and mast cells (Okamoto et al 1998 J Biol Chem 273(42):27104; Sanchez and Hla 2004, J Cell Biochem 92:913). It has a wide range of biological actions, including regulation of cell proliferation, differentiation, motility, vascularisation, and activation of inflammatory cells and platelets (Pyne and Pyne 2000, Biochem J. 349: 385). Five subtypes of S1P responsive receptor have been described, S1P1 (Edg-1), S1P2 (Edg-5), S1P3 (Edg-3), S1P4 (Edg-6), and S1P5 (Edg-8), forming part of the G-protein coupled endothelial differentiation gene family of receptors (Chun et al 2002 Pharmacological Reviews 54:265, Sanchez and Hla 2004 J Cellular Biochemistry, 92:913). These 5 receptors show differential mRNA expression, with S1P1-3 being widely expressed, S1P4 expressed on lymphoid and hematopoietic tissues and S1P5 primarily in brain and to a lower degree in spleen. They signal via different subsets of G proteins to promote a variety of biological responses (Kluk and Hla 2002 Biochem et Biophysica Acta 1582:72, Sanchez and Hla 2004, J Cellular Biochem 92:913).

Proposed roles for the S1P1 receptor include lymphocyte trafficking, cytokine induction/suppression and effects on endothelial cells (Rosen and Goetzl 2005 Nat Rev Immunol. 5:560). Agonists of the S1P1 receptor have been used in a number of autoimmune and transplantation animal models, including Experimental Autoimmune Encephalomelitis (EAE) models of MS, to reduce the severity of the induced disease (Brinkman et al 2003 JBC 277:21453; Fujino et al 2003 J Pharmacol Exp Ther 305:70; Webb et al 2004 J Neuroimmunol 153:108; Rausch et al 2004 J Magn Reson Imaging 20:16). This activity is reported to be mediated by the effect of S1P1 agonists on lymphocyte circulation through the lymph system. Treatment with S1P1 agonists results in the sequestration of lymphocytes within secondary lymphoid organs such as the lymph nodes, inducing a reversible peripheral lymphopoenia in animal models (Chiba et al 1998, J Immunology 160:5037, Forrest et al 2004 J Pharmacol Exp Ther 309:758; Sanna et al 2004 JBC 279:13839). Published data on agonists suggests that compound treatment induces loss of the S1P1 receptor from the cell surface via internalisation (Graler and Goetzl 2004 FASEB J 18:551; Matloubian et al 2004 Nature 427:355; Jo et al 2005 Chem Biol 12:703) and it is this reduction of S1P1 receptor on immune cells which contributes to the reduction of movement of T cells from the lymph nodes back into the blood stream.

S1P1 gene deletion causes embryonic lethality. Experiments to examine the role of the S1P1 receptor in lymphocyte migration and trafficking have included the adoptive transfer of labelled S1P1 deficient T cells into irradiated wild type mice. These cells showed a reduced egress from secondary lymphoid organs (Matloubian et al 2004 Nature 427:355).

S1P1 has also been ascribed a role in endothelial cell junction modulation (Allende et al 2003 102:3665, Blood Singelton et al 2005 FASEB J 19:1646). With respect to this endothelial action, S1P1 agonists have been reported to have an effect on isolated lymph nodes which may be contributing to a role in modulating immune disorders. S1P1 agonists caused a closing of the endothelial stromal 'gates' of lymphatic sinuses which drain the lymph nodes and prevent lymphocyte egress (Wei et al 2005, Nat. Immunology 6:1228).

The immunosuppressive compound FTY720 (JP11080026-A) has been shown to reduce circulating lymphocytes in animals and man, have disease modulating activity in animal models of immune disorders and reduce remission rates in relapsing remitting Multiple Sclerosis (Brinkman et al 2002 JBC 277:21453, Mandala et al 2002 Science 296:346, Fujino et al 2003 J Pharmacology and Experimental Therapeutics 305:45658, Brinkman et al 2004 American J Transplantation 4:1019, Webb et al 2004 J Neuroimmunology 153:108, Morris et al 2005 EurJ Immunol 35:3570, Chiba 2005 Pharmacology and Therapeutics 108: 308, Kahan et al 2003, Transplantation 76:1079, Kappos et al 2006 New Eng J Medicine 335:1124). This compound is a prodrug that is phosphorylated in vivo by sphingosine kinases to give a molecule that has agonist activity at the S1P1, S1P3, S1P4 and S1P5 receptors. Clinical studies have demonstrated that treatment with FTY720 results in bradycardia in the first 24 hours of treatment (Kappos et al 2006 New Eng J Medicine 335:1124). The bradycardia is thought to be due to agonism at the S1P3 receptor, based on a number of cell based and animal experiments. These include the use of S1P3 knock-out animals which, unlike wild type mice, do not demonstrate bradycardia following FTY720 administration and the use of S1P1 selective compounds. (Hale et al 2004 Bioorganic & Medicinal Chemistry Letters 14:3501, Sanna et al 2004 JBC 279: 13839, Koyrakh et al 2005 American J Transplantation 5:529)

Hence, there is a need for S1P1 receptor agonist compounds with selectivity over S1P3 which might be expected to show a reduced tendency to induce bradycardia.

The following patent applications describe oxadiazole derivatives as S1P1 agonists: WO03/105771, WO05/058848, WO06/047195, WO06/100633, WO06/115188, WO06/131336, WO07/024922 and WO07/116866.

The following patent applications describe tetrahydroisoquinolinyl-oxadiazole derivatives as S1P receptor agonists: WO06/064757, WO06/001463, WO04/113330.

WO08/064377 describes benzocycloheptyl analogs having S1P1 receptor activity.

A structurally novel class of compounds has now been found which provides agonists of the S1P1 receptor.

The present invention provides compounds of formula (I) or a pharmaceutically acceptable salt thereof thereof:

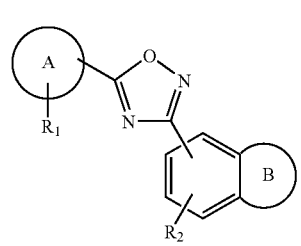

A is phenyl or a 5 or 6-membered heteroaryl ring;

$R_1$ is up to two substituents independently selected from halogen, $C_{(1-3)}$alkoxy, $C_{(1-3)}$fluoroalkyl, cyano, optionally substituted phenyl, $C_{(1-3)}$fluoroalkoxy, $C_{(1-6)}$alkyl and $C_{(3-6)}$cycloalkyl;

$R_2$ is hydrogen, halogen or $C_{(1-4)}$alkyl;

B is a 7-membered saturated ring selected from the following:

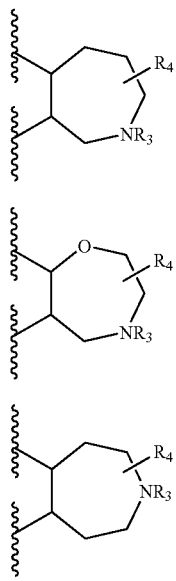

(a)

(b)

(c)

$R_3$ is hydrogen or $(CH_2)_{1-4}CO_2H$;
$R_4$ is hydrogen or $C_{(1-3)}$alkyl optionally interrupted by oxygen;

In one embodiment of the invention,
A is phenyl;
$R_1$ is up to two substituents independently selected from chloro, isopropoxy and cyano;
$R_2$ is hydrogen;
B is (a);
$R_3$ is hydrogen or $(CH_2)_{1-3}CO_2H$;
$R_4$ is hydrogen.

In one embodiment of the invention,
A is phenyl or pyridinyl;
$R_1$ is up to two substituents independently selected from chloro, isopropoxy and cyano;
$R_2$ is hydrogen;
B is (b);
$R_3$ is hydrogen or $(CH_2)_{1-4}CO_2H$;
$R_4$ is hydrogen.

In one embodiment of the invention,
A is phenyl or pyridinyl;
$R_1$ is up to two substituents independently selected from chloro, methoxy, isopropoxy, trifluoromethyl, phenyl and cyano;
$R_2$ is hydrogen;
B is (c);
$R_3$ is hydrogen or $(CH_2)_{1-3}CO_2H$;
$R_4$ is hydrogen.

In one embodiment A is phenyl. In another embodiment A is 3,4-disubstituted phenyl.

In one embodiment $R_1$ is two substituents one of which is $C_{(1-3)}$alkoxy, the other selected from halogen or cyano. In another embodiment $R_1$ is two substituents, one of which is isopropoxy and the other is selected from chloro or cyano. In another embodiment $R_1$ is two substituents selected from chloro, isopropoxy and cyano. In another embodiment $R_1$ is chloro and isopropoxy. In a further embodiment $R_1$ is chloro at the 3-position and isopropoxy at the 4-position when A is phenyl or $R_1$ is chloro at the 5-position and isopropoxy at the 6-position when A is pyridinyl. In another embodiment $R_1$ is isopropoxy and cyano. In a further embodiment $R_1$ is cyano at the 3-position and isopropoxy at the 4-position when A is phenyl or $R_1$ is chloro at the 5-position and isopropoxy at the 6-position when A is pyridinyl.

In one embodiment $R_2$ is hydrogen.

In one embodiment B is (b). In another embodiment B is (c).

In one embodiment $R_3$ is $(CH_2)_{1-3}CO_2H$. In another embodiment $R_3$ is $(CH_2)_3CO_2H$.

In one embodiment $R_4$ is hydrogen.

The present invention therefore provides compounds of formula (IA) or a pharmaceutically acceptable salt thereof:

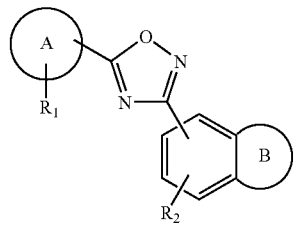

(IA)

A is phenyl or a 5 or 6-membered heteroaryl ring;
$R_1$ is up to two substituents independently selected from halogen, $C_{(1-3)}$alkoxy, $C_{(1-3)}$fluoroalkyl, cyano, optionally substituted phenyl, $C_{(1-3)}$fluoroalkoxy, $C_{(1-6)}$alkyl and $C_{(3-6)}$cycloalkyl;
$R_2$ is hydrogen, halogen or $C_{(1-4)}$alkyl;
B is a 7-membered saturated ring selected from the following:

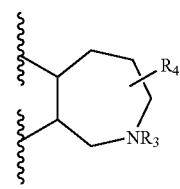

(a)

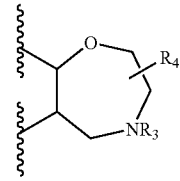

(b)

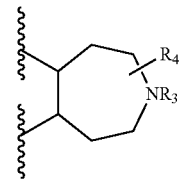

(c)

$R_3$ is hydrogen or $(CH_2)_{1-3}CO_2H$;
$R_4$ is hydrogen or $C_{(1-3)}$alkyl optionally interrupted by oxygen;

In one embodiment of the invention,
A is phenyl; and/or
$R_1$ is up to two substituents independently selected from chloro, isopropoxy and cyano; and/or R₂ is hydrogen; and/or
B is (a); and/or
R₃ is hydrogen or (CH₂)₁₋₃CO₂H; and/or
R₄ is hydrogen.
In one embodiment of the invention,
A is phenyl; and/or
R₁ is up to two substituents independently selected from chloro, isopropoxy and cyano; and/or
R₂ is hydrogen; and/or
B is (b); and/or
R₃ is hydrogen or (CH₂)₁₋₃CO₂H; and/or
R₄ is hydrogen.
In one embodiment of the invention,
A is phenyl; and/or
R₁ is up to two substituents independently selected from chloro, methoxy, isopropoxy, triflouromethyl, phenyl and cyano; and/or
R₂ is hydrogen; and/or
B is (c); and/or
R₃ is hydrogen or (CH₂)₁₋₃CO₂H; and/or
R₄ is hydrogen.

The term "alkyl" as a group or part of a group e.g. alkoxy or hydroxyalkyl refers to a straight or branched alkyl group in all isomeric forms. The term "C$_{(1-6)}$alkyl" refers to an alkyl group, as defined above, containing at least 1, and at most 6 carbon atoms Examples of such alkyl groups include methyl, ethyl, propyl, iso-propyl, n-butyl, iso-butyl, sec-butyl, or tert-butyl. Examples of such alkoxy groups include methoxy, ethoxy, propoxy, iso-propoxy, butoxy, iso-butoxy, sec-butoxy and tert-butoxy.

Suitable C$_{(3-6)}$cycloalkyl groups include cyclopropyl, cyclobutyl, cyclopentyl and cyclohexyl.

As used herein, the term "halogen" refers to fluorine (F), chlorine (Cl), bromine (Br), or iodine (I) and the term "halo" refers to the halogen: fluoro (—F), chloro (—Cl), bromo (—Br) and iodo (—I).

The term "heteroaryl" represents an unsaturated ring which comprises one or more heteroatoms selected from O, N or S. Examples of 5 or 6 membered heteroaryl rings include pyrrolyl, triazolyl, thiadiazolyl, tetrazolyl, imidazolyl, pyrazolyl, isothiazolyl, thiazolyl, isoxazolyl, oxazolyl, oxadiazolyl, furazanyl, furanyl, thienyl, pyridyl, pyrimidinyl, pyrazinyl, pyridazinyl and triazinyl.

In certain of the compounds of formula (I), dependent upon the nature of the substituent there are chiral carbon atoms and therefore compounds of formula (I) may exist as stereoisomers. The invention extends to all optical isomers such as stereoisomeric forms of the compounds of formula (I) including enantiomers, diastereoisomers and mixtures thereof, such as racemates. The different stereoisomeric forms may be separated or resolved one from the other by conventional methods or any given isomer may be obtained by conventional stereoselective or asymmetric syntheses.

Certain of the compounds herein can exist in various tautomeric forms and it is to be understood that the invention encompasses all such tautomeric forms.

It is understood that certain compounds of the invention contain both acidic and basic groups and may therefore exist as zwitterions at certain pH values.

Suitable compounds of the invention are:
7-(5-{3-chloro-4-[(1-methylethyl)oxy]phenyl}-1,2,4-oxadiazol-3-yl)-2,3,4,5-tetrahydro-1H-2-benzazepine
[7-(5-{3-chloro-4-[(1-methylethyl)oxy]phenyl}-1,2,4-oxadiazol-3-yl)-1,3,4,5-tetrahydro-2H-2-benzazepin-2-yl] acetic acid
2-[(1-methylethyl)oxy]-5-[3-(2,3,4,5-tetrahydro-1H-2-benzazepin-7-yl)-1,2,4-oxadiazol-5-yl]benzonitrile
[7-(5-{3-cyano-4-[(1-methylethyl)oxy]phenyl}-1,2,4-oxadiazol-3-yl)-1,3,4,5-tetrahydro-2H-2-benzazepin-2-yl] acetic acid
4-[7-(5-{3-cyano-4-[(1-methylethyl)oxy]phenyl}-1,2,4-oxadiazol-3-yl)-1,3,4,5-tetrahydro-2H-2-benzazepin-2-yl]butanoic acid
3-[7-(5-{3-cyano-4-[(1-methylethyl)oxy]phenyl}-1,2,4-oxadiazol-3-yl)-1,3,4,5-tetrahydro-2H-2-benzazepin-2-yl]propanoic acid
2-[(1-methylethyl)oxy]-5-[3-(2,3,4,5-tetrahydro-1H-3-benzazepin-6-yl)-1,2,4-oxadiazol-5-yl]benzonitrile
6-(5-{3-chloro-4-[(1-methylethyl)oxy]phenyl}-1,2,4-oxadiazol-3-yl)-2,3,4,5-tetrahydro-1H-3-benzazepine
3-[6-(5-{3-chloro-4-[(1-methylethyl)oxy]phenyl}-1,2,4-oxadiazol-3-yl)-1,2,4,5-tetrahydro-3H-3-benzazepin-3-yl]propanoic acid
[6-(5-{3-chloro-4-[(1-methylethyl)oxy]phenyl}-1,2,4-oxadiazol-3-yl)-1,2,4,5-tetrahydro-3H-3-benzazepin-3-yl] acetic acid
6-(5-{3-chloro-4-[(1-methylethyl)oxy]phenyl}-1,2,4-oxadiazol-3-yl)-2,3,4,5-tetrahydro-1H-2-benzazepine
[6-(5-{3-chloro-4-[(1-methylethyl)oxy]phenyl}-1,2,4-oxadiazol-3-yl)-1,3,4,5-tetrahydro-2H-2-benzazepin-2-yl] acetic acid
8-(5-{3-Chloro-4-[(1-methylethyl)oxy]phenyl}-1,2,4-oxadiazol-3-yl)-2,3,4,5-tetrahydro-1,4-benzoxazepine
3-[8-(5-{3-Chloro-4-[(1-methylethyl)oxy]phenyl}-1,2,4-oxadiazol-3-yl)-2,3-dihydro-1,4-benzoxazepin-4(5H)-yl]propanoic acid
4-[8-(5-{3-Chloro-4-[(1-methylethyl)oxy]phenyl}-1,2,4-oxadiazol-3-yl)-2,3-dihydro-1,4-benzoxazepin-4(5H)-yl]butanoic acid
[8-(5-{3-Chloro-4-[(1-methylethyl)oxy]phenyl}-1,2,4-oxadiazol-3-yl)-2,3-dihydro-1,4-benzoxazepin-4(5H)-yl]acetic acid
7-(5-{3-chloro-4-[(1-methylethyl)oxy]phenyl}-1,2,4-oxadiazol-3-yl)-2,3,4,5-tetrahydro-1H-3-benzazepine
2-[(1-methylethyl)oxy]-5-[3-(2,3,4,5-tetrahydro-1H-3-benzazepin-7-yl)-1,2,4-oxadiazol-5-yl]benzonitrile
7-{5-[4-[(1-methylethyl)oxy]-3-(trifluoromethyl)phenyl]-1,2,4-oxadiazol-3-yl}-2,3,4,5-tetrahydro-1H-3-benzazepine
7-{5-[2-(trifluoromethyl)-4-biphenylyl]-1,2,4-oxadiazol-3-yl}-2,3,4,5-tetrahydro-1H-3-benzazepine
3-[7-(5-{3-chloro-4-[(1-methylethyl)oxy]phenyl}-1,2,4-oxadiazol-3-yl)-1,2,4,5-tetrahydro-3H-3-benzazepin-3-yl]propanoic acid
[7-(5-{3-chloro-4-[(1-methylethyl)oxy]phenyl}-1,2,4-oxadiazol-3-yl)-1,2,4,5-tetrahydro-3H-3-benzazepin-3-yl] acetic acid
[7-(5-{3-cyano-4-[(1-methylethyl)oxy]phenyl}-1,2,4-oxadiazol-3-yl)-1,2,4,5-tetrahydro-3H-3-benzazepin-3-yl] acetic acid
(7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)acetic acid
(7-{5-[2-(trifluoromethyl)-4-biphenylyl]-1,2,4-oxadiazol-3-yl}-1,2,4,5-tetrahydro-3H-3-benzazepin-3-yl)acetic acid
4-[7-(5-{3-chloro-4-[(1-methylethyl)oxy]phenyl}-1,2,4-oxadiazol-3-yl)-1,2,4,5-tetrahydro-3H-3-benzazepin-3-yl]butanoic acid
4-[7-(5-{3-cyano-4-[(1-methylethyl)oxy]phenyl}-1,2,4-oxadiazol-3-yl)-1,2,4,5-tetrahydro-3H-3-benzazepin-3-yl]butanoic acid
4-(7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)butanoic acid 4-(7-{5-[2-(trifluoromethyl)-4-biphenylyl]-1,2,4-oxadiazol-3-yl}-1,2,4,5-tetrahydro-3H-3-benzazepin-3-yl)butanoic acid 2-(Methyloxy)-5-[3-(2,3,4,5-tetrahydro-1H-3-benzazepin-7-yl)-1,2,4-oxadiazol-5-yl]benzonitrile 9-(5-{3-chloro-4-[(1-methylethyl)oxy]phenyl}-1,2,4-oxadiazol-3-yl)-2,3,4,5-tetrahydro-1,4-benzoxazepine 2-[(1-methylethyl)oxy]-5-[3-(2,3,4,5-tetrahydro-1,4-benzoxazepin-9-yl)-1,2,4-oxadiazol-5-yl]benzonitrile 4-[9-(5-{3-Chloro-4-[(1-methylethyl)oxy]phenyl}-1,2,4-oxadiazol-3-yl)-2,3-dihydro-1,4-benzoxazepin-4(5H)-yl]butanoic acid 4-[9-(5-{3-cyano-4-[(1-methylethyl)oxy]phenyl}-1,2,4-oxadiazol-3-yl)-2,3-dihydro-1,4-benzoxazepin-4(5H)-yl]butanoic acid 2-[(1-methylethyl)oxy]-5-[3-(2,3,4,5-tetrahydro-1,4-benzoxazepin-7-yl)-1,2,4-oxadiazol-5-yl]benzonitrile 7-(5-{3-chloro-4-[(1-methylethyl)oxy]phenyl}-1,2,4-oxadiazol-3-yl)-2,3,4,5-tetrahydro-1,4-benzoxazepine hydrochloride 3-[7-(5-{3-cyano-4-[(1-methylethyl)oxy]phenyl}-1,2,4-oxadiazol-3-yl)-2,3-dihydro-1,4-benzoxazepin-4(5H)-yl]propanoic acid 3-[7-(5-{3-chloro-4-[(1-methylethyl)oxy]phenyl}-1,2,4-oxadiazol-3-yl)-2,3-dihydro-1,4-benzoxazepin-4(5H)-yl]propanoic acid 4-[7-(5-{3-cyano-4-[(1-methylethyl)oxy]phenyl}-1,2,4-oxadiazol-3-yl)-2,3-dihydro-1,4-benzoxazepin-4(5H)-yl]butanoic acid 4-[7-(5-{3-chloro-4-[(1-methylethyl)oxy]phenyl}-1,2,4-oxadiazol-3-yl)-2,3-dihydro-1,4-benzoxazepin-4(5H)-yl]butanoic acid 2-[(1-methylethyl)oxy]-5-[3-(2,3,4,5-tetrahydro-1,4-benzoxazepin-8-yl)-1,2,4-oxadiazol-5-yl]benzonitrile 4-[8-(5-{3-cyano-4-[(1-methylethyl)oxy]phenyl}-1,2,4-oxadiazol-3-yl)-2,3-dihydro-1,4-benzoxazepin-4(5H)-yl]butanoic acid 5-[9-(5-{3-Cyano-4-[(1-methylethyl)oxy]phenyl}-1,2,4-oxadiazol-3-yl)-2,3-dihydro-1,4-benzoxazepin-4(5H)-yl]pentanoic acid

[9-(5-{3-Cyano-4-[(1-methylethyl)oxy]phenyl}-1,2,4-oxadiazol-3-yl)-2,3-dihydro-1,4-benzoxazepin-4(5H)-yl]acetic acid 3-[9-(5-{5-Chloro-6-[(1-methylethyl)oxy]-3-pyridinyl}-1,2,4-oxadiazol-3-yl)-2,3-dihydro-1,4-benzoxazepin-4(5H)-yl]propanoic acid 3-[9-(5-{3-Cyano-4-[(1-methylethyl)oxy]phenyl}-1,2,4-oxadiazol-3-yl)-2,3-dihydro-1,4-benzoxazepin-4(5H)-yl]propanoic acid 3-[9-(5-{3-Chloro-4-[(1-methylethyl)oxy]phenyl}-1,2,4-oxadiazol-3-yl)-2,3-dihydro-1,4-benzoxazepin-4(5H)-yl]propanoic acid 2-[(1-Methylethyl)oxy]-5-[3-(2,3,4,5-tetrahydro-1H-3-benzazepin-7-yl)-1,2,4-oxadiazol-5-yl]-3-pyridinecarbonitrile formate 7-(5-{5-Chloro-6-[(1-methylethyl)oxy]-3-pyridinyl}-1,2,4-oxadiazol-3-yl)-2,3,4,5-tetrahydro-1H-3-benzazepine hydrochloride 4-[7-(5-{5-Chloro-6-[(1-methylethyl)oxy]-3-pyridinyl}-1,2,4-oxadiazol-3-yl)-1,2,4,5-tetrahydro-3H-3-benzazepin-3-yl]butanoic acid or pharmaceutically acceptable salts thereof.

In one embodiment of the invention a compound of formula (I) is 4-[7-(5-{3-cyano-4-[(1-methylethyl)oxy]phenyl}-1,2,4-oxadiazol-3-yl)-1,2,4,5-tetrahydro-3H-3-benzazepin-3-yl]butanoic acid or a pharmaceutically acceptable salt thereof.

In another embodiment of the invention a compound of formula (I) is 4-[9-(5-{3-Chloro-4-[(1-methylethyl)oxy]phenyl}-1,2,4-oxadiazol-3-yl)-2,3-dihydro-1,4-benzoxazepin-4(5H)-yl]butanoic acid or a pharmaceutically acceptable salt thereof.

Pharmaceutically acceptable derivatives of compounds of formula (I) include any pharmaceutically acceptable salt, ester or salt of such ester of a compound of formula (I) which, upon administration to the recipient is capable of providing (directly or indirectly) a compound of formula (I) or an active metabolite or residue thereof.

The compounds of formula (I) can form salts. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Certain of the compounds of formula (I) may form acid addition salts with one or more equivalents of the acid. The present invention includes within its scope all possible stoichiometric and non-stoichiometric forms. Salts may also be prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like.

Pharmaceutically acceptable acid addition salts may be prepared conventionally by reaction with the appropriate acid or acid derivative. Pharmaceutically acceptable salts with bases may be prepared conventionally by reaction with the appropriate inorganic or organic base.

The compounds of formula (I) may be prepared in crystalline or non-crystalline form, and, if crystalline, may optionally be hydrated or solvated. This invention includes within its scope stoichiometric hydrates or solvates as well as compounds containing variable amounts of water and/or solvent.

Included within the scope of the invention are all salts, solvates, hydrates, complexes, polymorphs, prodrugs, radiolabelled derivatives, stereoisomers and optical isomers of the compounds of formula (I).

The potencies and efficacies of the compounds of this invention for the S1P1 receptor can be determined by GTPγS assay performed on the human cloned receptor as described herein. Compounds of formula (I) have demonstrated agonist activity at the S1P1 receptor, using functional assays described herein.

Compounds of formula (I) and their pharmaceutically acceptable salts are therefore of use in the treatment of conditions or disorders which are mediated via the S1P1 receptor. In particular the compounds of formula (I) and their pharmaceutically acceptable salts are of use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes (herein after referred to as the "Disorders of the Invention").

Compounds of formula (I) and their pharmaceutically acceptable salts are therefore of use in the treatment of lupus erythematosis.

Compounds of formula (I) and their pharmaceutically acceptable salts are therefore of use in the treatment of psoriasis.

Compounds of formula (I) and their pharmaceutically acceptable salts are therefore of use in the treatment of multiple sclerosis.

It is to be understood that "treatment" as used herein includes prophylaxis as well as alleviation of established symptoms.

Thus the invention also provides compounds of formula (I) or pharmaceutically acceptable salts thereof, for use as therapeutic substances, in particular in the treatment of the conditions or disorders mediated via the S1P1 receptor. In particular the invention provides a compound of formula (I) or a pharmaceutically acceptable salt thereof for use as a therapeutic substance in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are of use as therapeutic substances in the treatment of lupus erythematosis.

Compounds of formula (I) and their pharmaceutically acceptable salts are of use as therapeutic substances in the treatment of psoriasis.

Compounds of formula (I) and their pharmaceutically acceptable salts are of use as therapeutic substances in the treatment of multiple sclerosis.

The invention further provides a method of treatment of conditions or disorders in mammals including humans which can be mediated via the S1P1 receptor, which comprises administering to the sufferer a therapeutically safe and effective amount of a compound of formula (I) or a pharmaceutically acceptable salt thereof. In particular the invention provides a method of treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes, which comprises administering to the sufferer a therapeutically safe and effective amount of a compound of formula (I) or a pharmaceutically acceptable salt thereof.

The invention provides a method of treatment of lupus erythematosis, which comprises administering to the sufferer a therapeutically safe and effective amount of a compound of formula (I) or a pharmaceutically acceptable salt thereof.

The invention provides a method of treatment of psoriasis, which comprises administering to the sufferer a therapeutically safe and effective amount of a compound of formula (I) or a pharmaceutically acceptable salt thereof.

The invention provides a method of treatment of multiple sclerosis, which comprises administering to the sufferer a therapeutically safe and effective amount of a compound of formula (I) or a pharmaceutically acceptable salt thereof.

In another aspect, the invention provides for the use of a compound of formula (I) or a pharmaceutically acceptable salt thereof in the manufacture of a medicament for use in the treatment of the conditions or disorders mediated via the S1P1 receptor.

In particular the invention provides a compound of formula (I) or a pharmaceutically acceptable salt thereof for use in the manufacture of a medicament for use in the treatment of multiple sclerosis, autoimmune diseases, chronic inflammatory disorders, asthma, inflammatory neuropathies, arthritis, transplantation, Crohn's disease, ulcerative colitis, lupus erythematosis, psoriasis, ischemia-reperfusion injury, solid tumours, and tumour metastasis, diseases associated with angiogenesis, vascular diseases, pain conditions, acute viral diseases, inflammatory bowel conditions, insulin and non-insulin dependant diabetes.

Compounds of formula (I) and their pharmaceutically acceptable salts are of use in the manufacture of a medicament for use in the treatment of lupus erythematosis.

Compounds of formula (I) and their pharmaceutically acceptable salts are of use in the manufacture of a medicament for use in the treatment of psoriasis.

Compounds of formula (I) and their pharmaceutically acceptable salts are of use in the manufacture of a medicament for use in the treatment of multiple sclerosis.

In order to use the compounds of formula (I) and pharmaceutically acceptable salts thereof in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier or excipient.

In a further aspect, the present invention provides a process for preparing a pharmaceutical composition, the process comprising mixing a compound of formula (I) or a pharmaceutically acceptable salt thereof and a pharmaceutically acceptable carrier or excipient.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents (e.g. pregelatinised maize starch, polyvinylpyrrolidone or hydroxypropyl methylcellulose); fillers (e.g. lactose, microcrystalline cellulose or calcium hydrogen phosphate); tabletting lubricants (e.g. magnesium stearate, talc or silica); disintegrants (e.g. potato starch or sodium starch glycollate); and acceptable wetting agents (e.g. sodium lauryl sulphate). The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents (e.g. sorbitol syrup, cellulose derivatives or hydrogenated edible fats), emulsifying agents (e.g. lecithin or acacia), non-aqueous vehicles (which may include edible oils e.g. almond oil, oily esters, ethyl alcohol or fractionated vegetable oils), preservatives (e.g. methyl or propyl-p-hydroxybenzoates or sorbic acid), and, if desired, conventional flavourings or colorants, buffer salts and sweetening agents as appropriate. Preparations for oral administration may be suitably formulated to give controlled release of the active compound.

For parenteral administration, fluid unit dosage forms are prepared utilising a compound of the invention or pharmaceutically acceptable salts thereof and a sterile vehicle. Formulations for injection may be presented in unit dosage form e.g. in ampoules or in multi-dose, utilising a compound of the invention or pharmaceutically acceptable derivatives thereof and a sterile vehicle, optionally with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of formula (I) or pharmaceutically acceptable salts thereof may also be formulated in rectal compositions such as suppositories or retention enemas, e.g. containing conventional suppository bases such as cocoa butter or other glycerides.

The compounds of formula (I) or pharmaceutically acceptable salts thereof may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of formula (I) or pharmaceutically acceptable salts thereof, may be formulated as solutions for administration via a suitable metered or unitary dose device or alternatively as a powder mix with a suitable carrier for administration using a suitable delivery device. Thus compounds of formula (I) or pharmaceutically acceptable salts thereof may be formulated for oral, buccal, parenteral, topical (including ophthalmic and nasal), depot or rectal administration or in a form suitable for administration by inhalation or insufflation (either through the mouth or nose).

The compounds of formula (I) or pharmaceutically acceptable salts thereof may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

The composition may contain from 0.1% to 99% by weight, preferably from 10 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, 1.0 to 500 mg or 1.0 to 200 mg and such unit doses may be administered more than once a day, for example two or three times a day.

Compounds of formula (I) or pharmaceutically acceptable salts thereof may be used in combination preparations, in combination with other active ingredients. For example, the compounds of the invention may be used in combination with cyclosporin A, methotrexate, steroids, rapamycin, proinflammatory cytokine inhibitors, immunomodulators including biologicals or other therapeutically active compounds.

The subject invention also includes isotopically-labeled compounds, which are identical to those recited in formulas I and following, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3H$, $^{11}C$, $^{14}C$, $^{18}F$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labeled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^8F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula (I) and following of this invention can generally be prepared by carrying out the procedures disclosed in the Schemes and/or in the Examples below, by substituting a readily available isotopically labelled reagent for a non-isotopically labeled reagent.

In a further aspect, this invention provides processes for preparation of a compound of formula (I).

One route which may be used to prepare compounds of formula (I) when B is

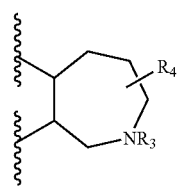

(a)

is illustrated in Scheme 1 wherein $R_1$, $R_2$ $R_4$ and A are as described in formula (I) except that $R_2$ is not chloro, bromo or iodo, R is alkyl (for example, ethyl, t-butyl) and hal is chloro, bromo or iodo.

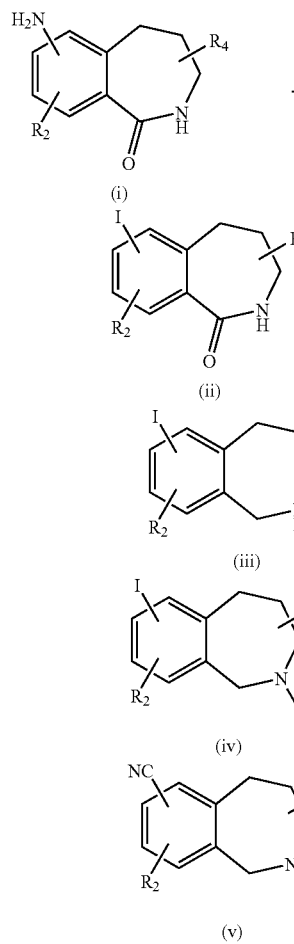

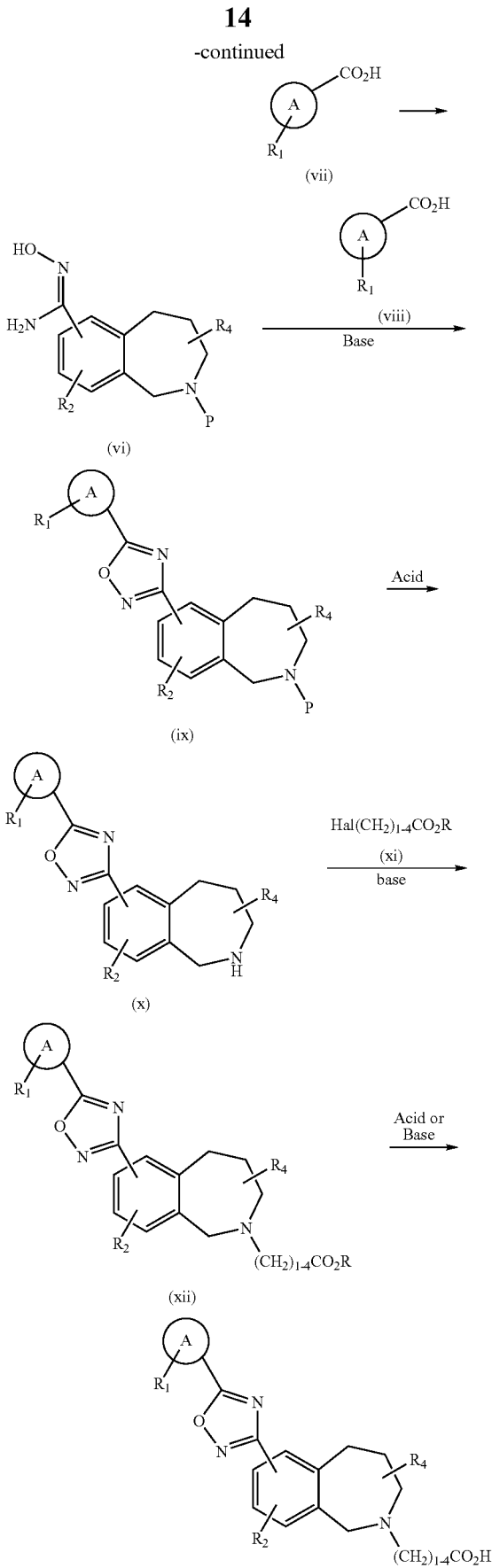

Compounds of formula (i) which are commercially available or may be prepared by a number of routes (e.g Johnson, Paul D.; et al; Bioorganic & Medicinal Chemistry Letters (2003), 13(23), 4197-4200), may be converted into compounds of formula (ii) by treatment with iodoform in the presence of a suitable nitrite such as tert-butyl nitrite in a suitable solvent such as tetrahydrofuran (THF). Compounds of formula (ii) may be converted into compounds of formula (iii) by treatment with an appropriate reducing agent such as diborane or lithium aluminium hydride in a solvent such as THF at an elevated temperature such as 80° C. Compounds of formula (iii) may be converted to a protected derivative (iv), where P represents a suitable protecting group such as t-butyloxy carbonyl (BOC), for example by treatment with bis(1,1-dimethylethyl)dicarbonate in the presence of a base such as triethylamine in a suitable solvent such as dichloromethane (DCM). Compounds of formula (iv) may be converted into compounds of formula (v) by treatment with a suitable cyanide source such as zinc cyanide in the presence of a catalyst such as tetrakistriphenylphosphine palladium (0) in a suitable solvent such as dimethylformamide (DMF) at an elevated temperature such as 80° C. Compounds of formula (v) may be converted into compounds of formula (vi) by treatment with hydroxylamine hydrochloride and an appropriate base, such as sodium bicarbonate, in a solvent such as methanol or ethanol at an elevated temperature such as 60° C. Compounds of formula (vi) may be converted into compounds of formula (ix) by treatment with a carboxylic acid chloride of formula (viii) in the presence of a base such as triethylamine in a suitable solvent such as DMF. Such reactions are typically stirred for a period of time at room temperature, then at elevated temperatures, such as 120° C. Acid chlorides of formula (viii) are either commercially available or may be prepared from the corresponding acid (vii) by conventional means. Alternatively compounds of formula (vi) may be converted into compounds of formula (ix) by treatment with a carboxylic acid of formula (vii) in the presence of a suitable amide coupling agent such as 1-(3-dimethylaminopropyl)-N'-ethylcarbodiimide hydrochloride (EDAC) and 1-hydroxybenzotriazole (HOBT) in a suitable solvent such as DMF. Such reactions are typically carried out at elevated temperature, such as 50-80° C. Typically, the acid (vii), EDAC and HOBt are stirred for a period of time at room temperature prior to addition of the compound of formula (vi). Compounds of formula (ix), where P=BOC, may be converted into compounds of formula (x) by treatment with a suitable acid, typically trifluoroacetic acid or hydrochloric acid in a suitable solvent such as 1,4-dioxane. Compounds of formula (x) may be converted into compounds of formula (xii) by treatment with an alkylating agent (xi) in the presence of a base such as cesium carbonate in a solvent such as DMF or acetonitrile. Such reactions may be carried out at elevated temperature, such as 70° C. The alkylating agents (xi) are typically commercially available or may be prepared using standard methods. Compounds of formula (xii) may be converted into certain compounds of formula (I) wherein B is

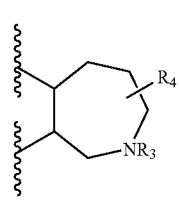

(a)

and $R_3$ represents $(CH_2)_{1-4}CO_2H$ by treatment with a base such as aqueous sodium hydroxide in an alcoholic solvent such as ethanol or methanol. A co-solvent, such as THF, may be added to aid dissolution. The hydrolysis reaction may be carried out at room temperature or at an elevated temperature such as 50-80° C. Alternatively, this transformation may be carried out using solid sodium hydroxide in ethanol in a microwave reactor at a temperature such as 100° C. or where R=t-butyl, with trifluoroacetic acid (TFA) or HCl.

Compounds of formula (I) wherein $R_2$ and $R_4$ are both hydrogen, B is

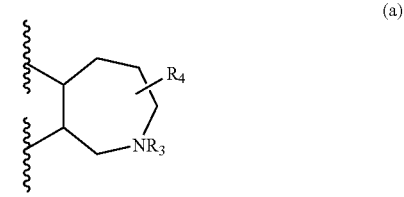

(a)

$R_3$ is $(CH_2)_{1-4}CO_2H$, $R_1$, and A are as defined in formula (I) and the oxadiazole moiety is attached to the benzazepine moiety at position 6 may alternatively be prepared by the route illustrated in Scheme 2.

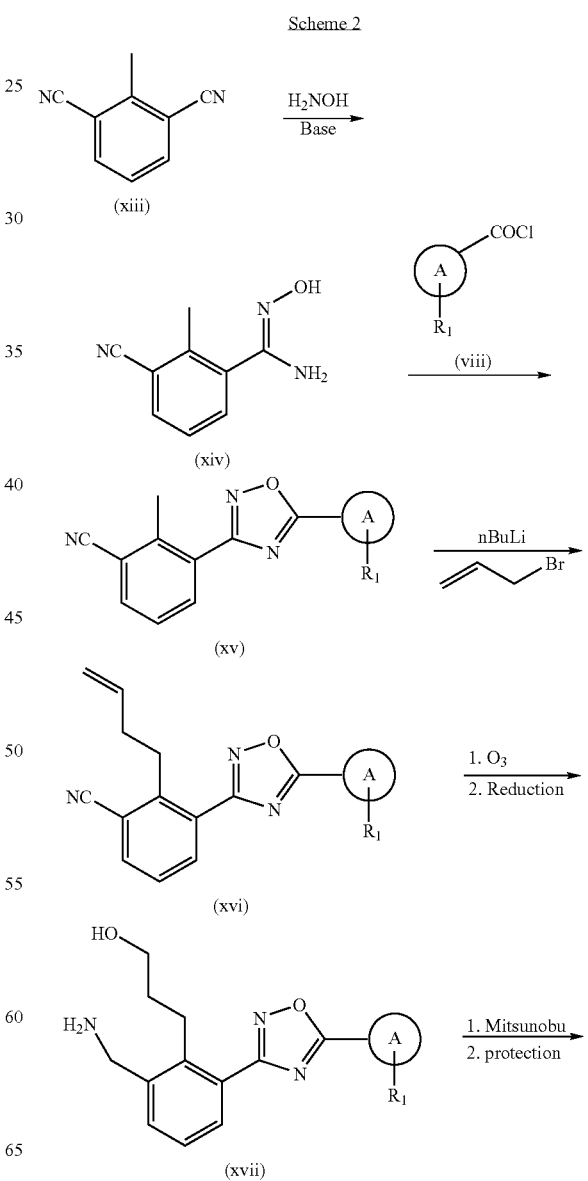

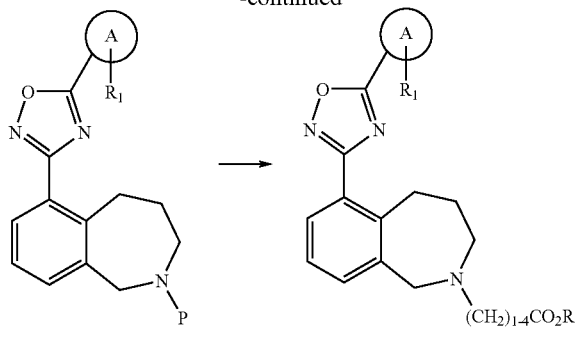

The commercially available compound of formula (xiii) may be converted into the compound of formula (xiv) by treatment with hydroxylamine hydrochloride as described in Scheme 1 for conversion of (v) to (vi). The compounds of formula (xiv) may be converted into compounds of formula (xv) by treatment with a carboxylic acid chloride of formula (viii) in the presence of a base such as triethylamine as described in Scheme 1 for conversion of (vi) to (ix). Compounds of formula (xv) may be converted into compounds of formula (xvi) by treatment with an appropriate base such as n-butyl lithium followed by allyl bromide in a solvent such as THF at reduced temperatures such as −78° C. Compounds of formula (xvi) may be converted to compounds of formula (xvii) by treatment with ozone in a suitable solvent such as DCM, at a reduced temperature such as −78° C. followed by reduction using a suitable reducing agent such as borane—dimethyl sulphide complex in a suitable solvent such as THF. Compounds of formula (xvii) may be converted into compounds of formula (ix), typically by cyclisation under Mitsunobu conditions for example using diisopropyl azodicarboxylate (DIAD) and triphenylphosphine in a suitable solvent such as DCM, followed by encorporation of a suitable protecting group on the benzazepine nitrogen, such as BOC, as described in Scheme 1 for conversion of (iii) to (iv). Compounds of formula (ixa) may be converted to compounds of formula (I) as described in scheme 1 for conversion of (ix) to certain compounds of formula (I)

One route which may be used to prepare compounds of formula (I) wherein B is

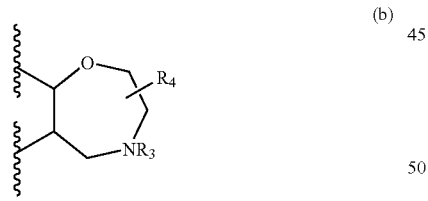

$R_3$ is $(CH_2)_{1-4}CO_2H$, $R_1$, $R_2$, $R_4$ and A are as defined in formula (I) except that $R_2$ is not chloro, bromo or iodo, R is alkyl (for example methyl, t-butyl) and Hal is chloro, bromo or iodo.

Scheme 3

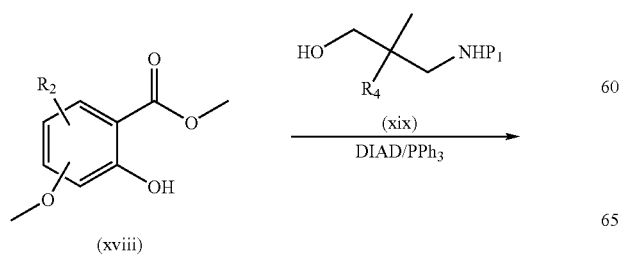

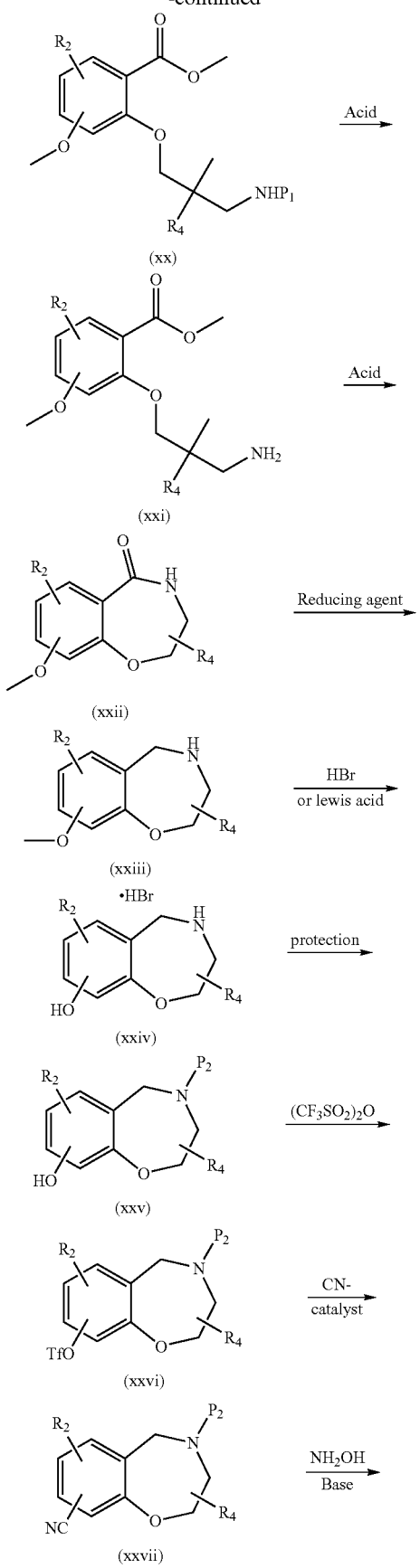

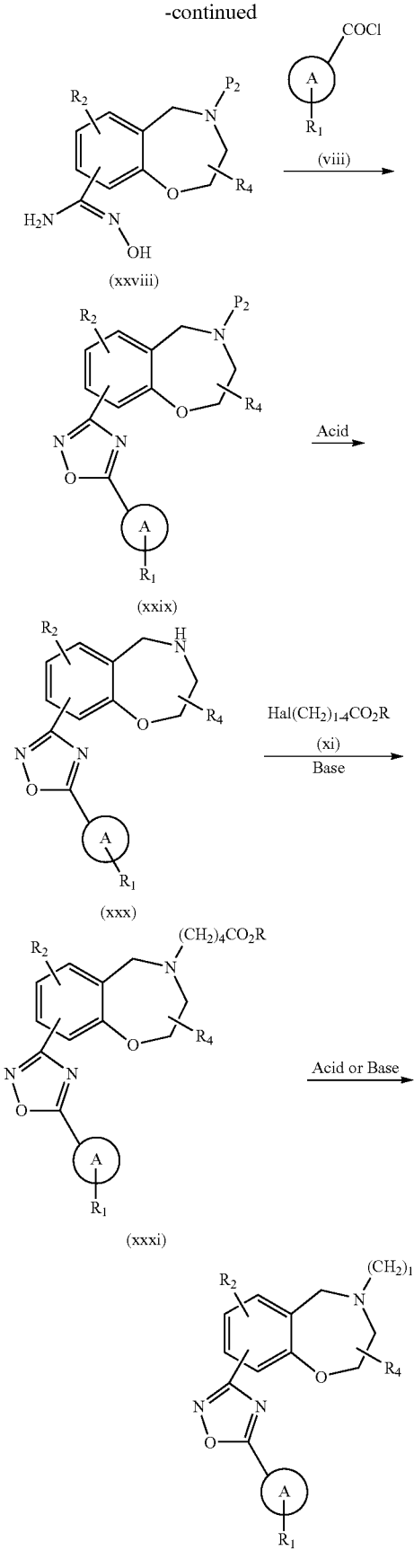

Compounds of formula (xviii) which are either commercially available (e.g. Aldrich) or prepared using standard methods, may be converted into compounds of formula (xx), typically by reaction with a protected ethanolamine (xix) where $P_1$ represents a suitable protecting group such as BOC, under Mitsunobu conditions using, for example DIAD and triphenylphosphine in a suitable solvent such as THF. Compounds of formula (xx) may be converted into compounds of formula (xxi) and/or (xxii) by treatment with acid, typically trifluoroacetic acid or hydrochloric acid. Compounds of formula (xxi) may be also be converted into compounds of formula (xxii) by heating in an appropriate solvent such as toluene at elevated temperatures such as 80° C. Compounds of formula (xxii) may be converted into compounds of formula (xxiii) by treatment with an appropriate reducing agent such as lithium aluminium hydride at a low temperature such as below 15° C., in a solvent such as THF, then elevating the temperature for example to 80° C. Compounds of formula (xxiii) may be converted to compounds of formula (xxiv) by treatment with a Lewis acid such as boron tribromide or a strong acid such as HBr.

Compounds of formula (xxiv) may be converted to a protected derivative (xxv), where $P_2$ represents a suitable protecting group such as t-butyloxy carbonyl (BOC), as described in Scheme 1 for conversion of (iii) to (iv). Compounds of formula (xxv) may be converted into compounds of formula (xxvi) by treatment with trifluoromethanesulphonic anhydride in an appropriate solvent such as pyridine. Compounds of formula (xxvi) may be converted into compounds of formula (xxvii) by treatment with a suitable cyanide such as zinc cyanide in the presence of a catalyst such as tetrakistriphenylphosphine palladium (0) in a suitable solvent such as DMF. Compounds of formula (xxvii) may be converted into compounds of formula (I) using methods analogous to those described for conversion of compounds of formula (v) to certain compounds of formula (I) (Scheme 1)

An alternative route to intermediate (xxvii) where the cyano group is in the 9 position and $P_2$ represents a suitable protecting group such as BOC, and $R_2$ and $R_4$ are hydrogen (represented by formula (xxviia) is illustrated in Scheme 4

Scheme 4

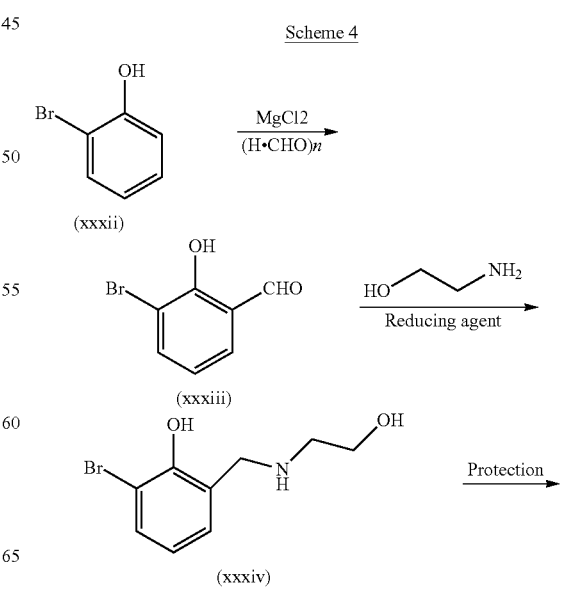

-continued

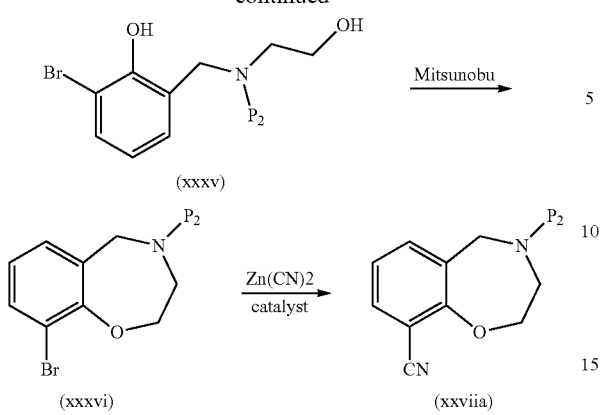

(xxxv)

(xxxvi)

(xxviia)

The compound of formula (xxxii) may be converted into the compound of formula (xxxiii) by treatment with paraformaldehyde and dry magnesium chloride in an appropriate solvent such as THF with heating under reflux. Compounds of formula (xxxiii) may be converted into compounds of formula (xxxiv) by treatment with ethanolamine in the presence of a reducing agent such as sodium triacetoxyborohydride. Compounds of formula (xxxiv) may be converted to a protected derivative (xxxv), where $P_2$ represents a suitable protecting group such as BOC as described in Scheme 1 for conversion (iii) to (iv). Compounds of formula (xxxv) may be converted into compounds of formula (xxxvi), typically by cyclisation under Mitsunobu conditions using, for example diisopropyl azodicarboxylate (DIAD) and triphenylphosphine in a suitable solvent such as THF. Compounds of formula (xxxvi) may be converted into compounds of formula (xxviia) by treatment with a suitable cyanide source such as zinc cyanide as described in Scheme 1 for conversion of (iv) to (v).

One route which may be used to prepare compounds of formula (I), wherein $R_1$, $R_2$, $R_4$ and A are as described in formula (I), $R_3$ represents $(CH_2)_{1-4}CO_2H$ and B is

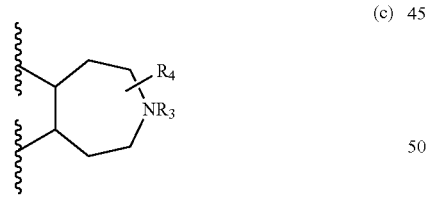

(c)

is illustrated in Scheme 5. R is alkyl (for example ethyl, t-butyl) and Hal is chloro, bromo or iodo.

Scheme 5

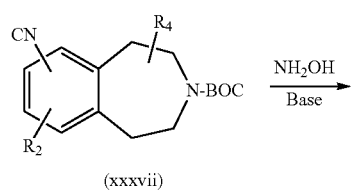

(xxxvii)

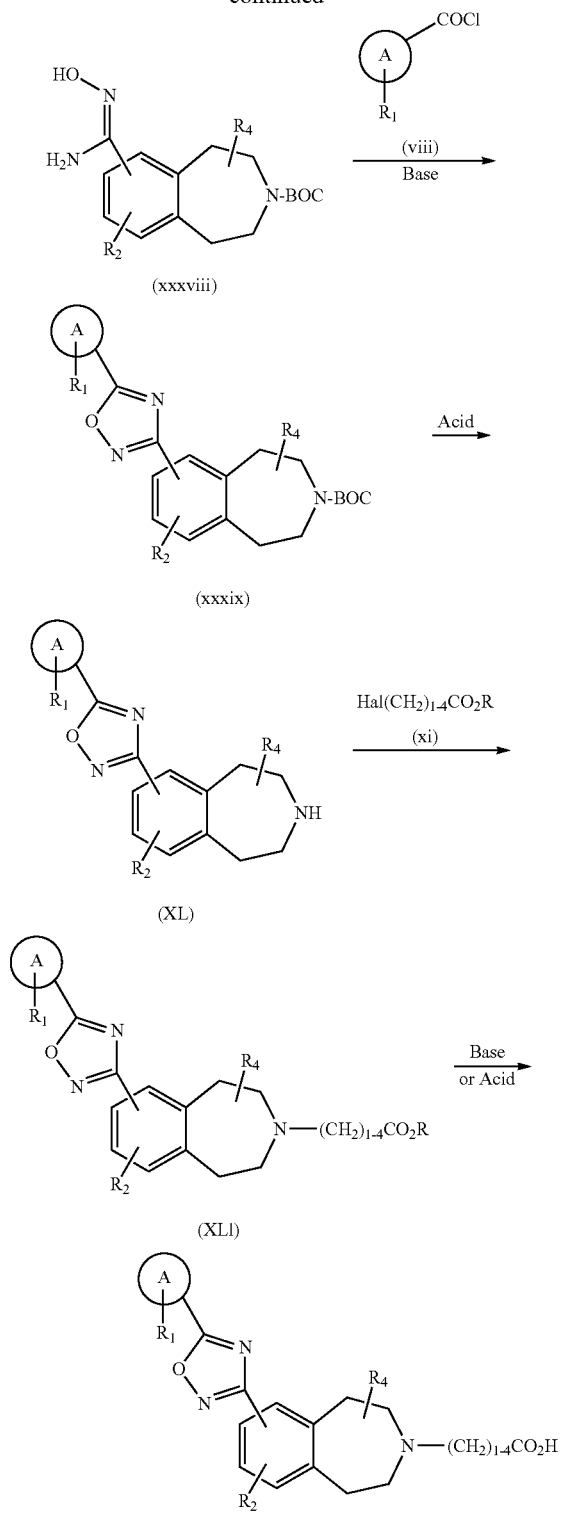

(xxxviii)

(xxxix)

(XL)

(XLl)

Compounds of formula (xxxvii) for example whereby the cyano group is in the 7 position (prepared for example, using the method described in Micheli, F. et al. Journal of Medicinal Chemistry (2007), 50(21), 5076-5089), may be converted into compounds of formula (I) using methods analogous to those described for the conversion of compounds of formula (v) to certain compounds of formula (I) (Scheme 1)

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Abbreviations:
g—grams
mg—milligrams
ml—milliliters
ul—microliters
$BOC_2O$—bis(1,1-dimethylethyl) dicarbonate
MeCN—acetonitrile
MeOH—methanol
EtOH—ethanol
Et2O—diethyl ether
EtOAc—ethyl acetate
DCM—dichloromethane
DIAD—diisopropyl azodicarboxylate
DIPEA—diisopropylethylamine
DME—1,2-bis(methyloxy)ethane
DMF—N,N-dimethylformamide
DMSO—dimethylsulphoxide
$d_6$DMSO—deuterated dimethylsulphoxide
EDAC—N-(3-Dimethylaminopropyl)-N'-ethylcarbodiimide hydrochloride
EDC—N-(3-Dimethylaminopropyl)-N'-ethylcarbodiimide hydrochloride
EDCI—N-(3-Dimethylaminopropyl)-N'-ethylcarbodiimide hydrochloride
HOBT/HOBt—Hydroxybenzotriazole
IPA—isopropylalcohol
MeOD—deuterated methanol
NCS—N-chlorosuccinimide
$PPh_3$—Triphenylphosphine
PyBOP—Benzotriazol-1-yl-oxytripyrrolidinophosphonium hexafluorophosphate
THF—tetrahydrofuran
TFA—trifluoroacetic acid
dba—dibenzylidene acetone
RT—room temperature
° C.—degrees Celsius
M—Molar
H—proton
s—singlet
d—doublet
t—triplet
q—quartet
MHz—megahertz
MeOD—deuterated methanol
LCMS—Liquid Chromatography Mass Spectrometry
LC/MS—Liquid Chromatography Mass Spectrometry
MS—mass spectrometry
ES—Electrospray
MH+—mass ion+H+
MDAP—mass directed automated preparative liquid chromatography.
sat.—saturated
SCX—solid phase cation exchange chromatography General Chemistry Section The methods described below are given for illustrative purposes, intermediates in the preparation of the examples may not necessarily have been prepared from the specific batches described.

Preparation 1

7-Iodo-2,3,4,5-tetrahydro-1H-2-benzazepin-1-one

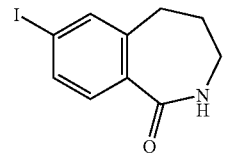

7-Amino-2,3,4,5-tetrahydro-1H-2-benzazepin-1-one (may be prepared as described in: Preparation of benzazepinylpyrrolidonylsulfonamides as Factor Xa inhibitors; WO2007059952) (500 mg, 2.84 mmol) and triiodomethane (2234 mg, 5.67 mmol) were dissolved in THF (100 ml). Then 1,1-dimethylethyl nitrite (0.675 ml, 5.67 mmol) dissolved in THF (20 ml) was added drop-wise over 20 minutes and the resultant solution stirred for 1 hour. The mixture was heated at 50° C. for 30 minutes. Most of the solvent was removed by evaporation and the crude subjected to biotage chromatography (EtOAc/hexane 3:1) to yield the title compound (550 mg) as a pale yellow solid. MS (ES) $C_{10}H_{10}INO$ requires 287: found 287.8 $(M+H)^+$.

Preparation 2

7-Iodo-2,3,4,5-tetrahydro-1H-2-benzazepine

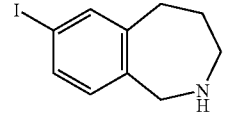

7-Iodo-2,3,4,5-tetrahydro-1H-2-benzazepin-1-one (Preparation 1) (550 mg, 1.916 mmol) was dissolved in dry THF (70 ml) and treated with borane-THF complex (1M) (11.49 ml, 11.49 mmol) and heated at reflux for 4 hours. Then the reaction was left standing overnight. Additional borane-THF complex (1M, 2 ml) was added and the reaction heated at reflux temperature for a further 2 hours and 30 minutes. Methanol was carefully added to the cooled reaction mixture. The reaction was stirred until fizzing stopped. Then 2N HCl (aq) (20 ml) was carefully added portion-wise and, after fizzing had subsided, the solution heated at 75° C. for 30 minutes. LC/MS showed one major product. The reaction mixture was cooled and water was added (20 ml). The mixture was washed with EtOAc (40 ml), basified with 2 N NaOH (aq) and extracted with EtOAc (50 ml). The EtOAc layer was dried over anhydrous $MgSO_4$ and evaporated to yield the title compound (400 mg) as a white solid. MS (ES) $C_{10}H_{12}IN$ requires 273: found 274 $(M+H)^+$.

Preparation 3

1,1-Dimethylethyl 7-iodo-1,3,4,5-tetrahydro-2H-2-benzazepine-2-carboxylate

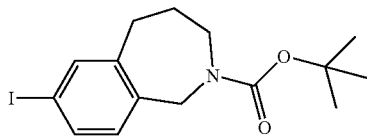

7-Iodo-2,3,4,5-tetrahydro-1H-2-benzazepine (Preparation 2) (450 mg, 1.648 mmol) was dissolved in DCM (30 ml) and treated with BOC$_2$O (0.459 ml, 1.977 mmol) followed by triethylamine (0.459 ml, 3.30 mmol). The reaction mixture was stirred at RT for 30 minutes. LC/MS showed one major product. The reaction was washed with 0.5M HCl (20 ml), sat NaHCO$_3$ (20 ml), dried over anhydrous MgSO$_4$ and evaporated to yield the title compound (650 mg) as a colourless oil. MS (ES) $C_{15}H_{20}INO_2$ requires 373; found 318 (M+H−56)$^+$.

Preparation 4

1,1-Dimethylethyl 7-cyano-1,3,4,5-tetrahydro-2H-2-benzazepine-2-carboxylate

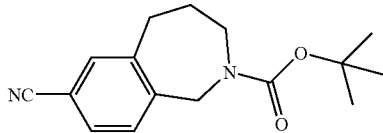

1,1-Dimethylethyl-7-iodo-1,3,4,5-tetrahydro-2H-2-benzazepine-2-carboxylate (Preparation 3) (650 mg, 1.742 mmol), zinc(II)cyanide (123 mg, 1.045 mmol) and tetrakis(triphenylphosphine)palladium(0) (201 mg, 0.174 mmol) were stirred in dry DMF at 80° C. for 45 minutes. EtOAc (100 ml) was added to the cooled reaction before washing with water (2×70 ml) and brine (100 ml). The EtOAc layer was dried over anhydrous MgSO$_4$ and evaporated. TLC (EtOAc/hexane 1:3) showed 2 spots, one with a very high RF. The crude product was subjected to biotage chromatography (EtOAc/hexane 1:3) and the lower RF spot was isolated. On evaporation the title compound was obtained (350 mg) as a colourless oil. MS (ES) $C_{16}H_{20}N_2O_2$ requires 272; found 217(M+H−56)$^+$.

Preparation 5

1,1-Dimethylethyl 7-[(hydroxyamino)(imino)methyl]-1,3,4,5-tetrahydro-2H-2-benzazepine-2-carboxylate

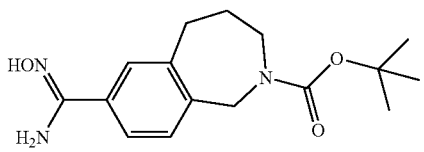

1,1-Dimethylethyl 7-cyano-1,3,4,5-tetrahydro-2H-2-benzazepine-2-carboxylate (Preparation 4) (350 mg, 1.285 mmol), hydroxylamine hydrochloride (223 mg, 3.21 mmol) and sodium bicarbonate (540 mg, 6.43 mmol) were suspended in ethanol (15 ml) and stirred at 55° C. for 5 hours. The reaction mixture was left standing overnight. LC/MS showed a single major product. Inorganics were removed by filtration, washing well with 10% MeOH/DCM to dissolve any precipitated product. Solvent evaporation yielded a white solid. Trituration with ether gave the title compound (320 mg). MS (ES) $C_{16}H_{23}N_3O_3$ requires 305; found 306.2 (M+H)$^+$.

Preparation 6

3-Chloro-4-[(1-methylethyl)oxy]benzoic acid

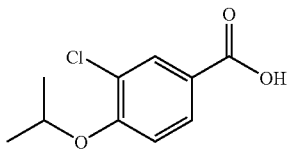

Propan-2-ol (2.45 ml) and PPh$_3$ (1.18 g) were dissolved in THF (30 ml), cooled to 0° C., treated with methyl 3-chloro-4-hydroxybenzoate (6.00 g) followed by the drop-wise addition of DIAD (9.44 ml) and stirred at RT overnight. The reaction mixture was then evaporated and purified on silica cartridges (4×100 g), eluting with a 0 to 40% mixture of EtOAc in pentane to give the crude product (7.00 g) as a colourless oil. This was dissolved in MeOH (30 ml) and 2 M aqueous NaOH (30 ml) and stirred at RT for a weekend. The reaction mixture was then evaporated and re-dissolved in H$_2$O. This solution was washed with Et$_2$O, acidified to pH=1 and extracted with Et$_2$O. These latter extracts were dried over anhydrous MgSO$_4$, filtered and evaporated to give the title compound (4.16 g) as a white solid. δH (MeOD, 400 MHz): 1.37 (6H, d), 4.77 (1H, septet), 7.12 (1H, d), 7.90 (1H, d), 7.98 (1H, s). MS (ES): $C_{10}H_{11}{}^{35}ClO_3$ requires 214; found 215 (M+H)$^+$.

Preparation 7

1,1-Dimethylethyl 7-(5-{3-chloro-4-[(1-methylethyl)oxy]phenyl}-1,2,4-oxadiazol-3-yl)-1,3,4,5-tetrahydro-2H-2-benzazepine-2-carboxylate

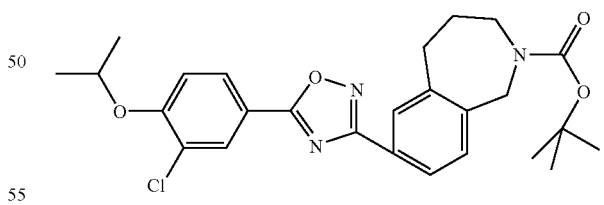

3-Chloro-4-[(1-methylethyl)oxy]benzoic acid (Preparation 6) (105 mg, 0.491 mmol), EDC (113 mg, 0.589 mmol) and HOBT (90 mg, 0.589 mmol) were dissolved in dry DMF (5 ml) and stirred for 5 minutes. 1,1-Dimethylethyl 7-[hydroxyamino)(imino)methyl]-1,3,4,5-tetrahydro-2H-2-benzazepine-2-carboxylate (Preparation 5) (150 mg, 0.491 mmol) was added and the mixture stirred for 1 hour, heated at 90° C. for 2 hours then left standing overnight. The reaction was heated at 90° C. for a further 3 hours. EtOAc (50 ml) was added and the reaction washed with sat. NaHCO$_3$ (aq) (50 ml) and water (2×50 ml) before drying over anhydrous MgSO$_4$ and evaporation of the solvent. The crude oil obtained was subjected to biotage chromatography (EtOAc/hexane 1:4) to give 100 mg of a colourless oil. The oil slowly began to solidify overnight to a white waxy solid. Trituration with ether/hexane yielded the title compound (38 mg) as a white solid after filtration. A further batch (30 mg) precipitated out of the solution slowly. δH (400 MHz, $d_6$DMSO) 1.31 (9H, s), 1.36 (6H, d), 1.69 (2H, m), 3.06 (2H, m), 3.65 (2H, m), 4.44 (2H, s), 4.84-4.94 (1H, m), 7.38-7.46 (2H, m), 7.84-7.91 (2H, m), 8.11 (1H, dd), 8.18 (1H, d).

Preparation 8

1,1-Dimethylethyl [7-(5-{3-chloro-4-[(1-methylethyl)oxy]phenyl}-1,2,4-oxadiazol-3-yl)-1,3,4,5-tetrahydro-2H-2-benzazepin-2-yl]acetate

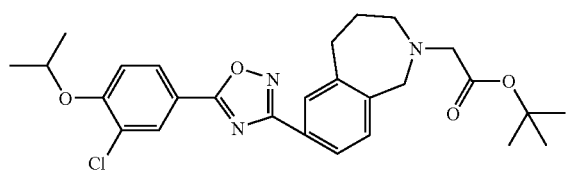

7-(5-{3-chloro-4-[(1-methylethyl)oxy]phenyl}-1,2,4-oxadiazol-3-yl)-2,3,4,5-tetrahydro-1H-2-benzazepine (Example 1) (60 mg, 0.143 mmol) and caesium carbonate (140 mg, 0.428 mmol) were stirred in dry DMF (5 ml) and treated with tert-butyl bromoacetate (0.032 ml, 0.214 mmol). The mixture was stirred at RT for 1.5 hours. EtOAc (50 ml) and ether (20 ml) were added and the mixture washed with water (3×60 ml) and brine (40 ml). Drying over anhydrous $MgSO_4$ and evaporation of solvent yielded a clear, colourless oil (80 mg). The oil was subjected to biotage chromatography (EtOAc/hexane 3:1) to give the title compound (65 mg) as a clear, colourless oil. MS (ES) $C_{27}H_{32}{}^{35}ClN_3O_4$ requires 497; found 498 $(M+H)^+$.

Preparation 9

1,1-Dimethylethyl 7-(5-{3-cyano-4-[(1-methylethyl)oxy]phenyl}-1,2,4-oxadiazol-3-yl)-1,3,4,5-tetrahydro-2H-2-benzazepine-2-carboxylate

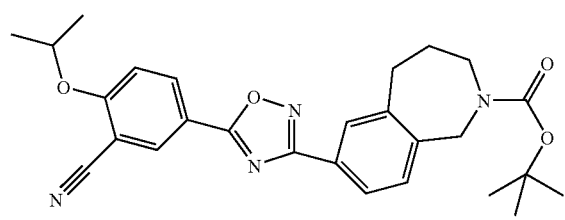

3-Cyano-4-[(1-methylethyl)oxy]benzoic acid (can be prepared as described in WO2005/58848) (302 mg, 1.474 mmol), EDC (339 mg, 1.768 mmol) and HOBT (271 mg, 1.768 mmol) were stirred in DMF (3 ml) for 5 minutes. 1,1-Dimethylethyl 7-[(hydroxyamino)(imino)methyl]-1,3,4,5-tetrahydro-2H-2-benzazepine-2-carboxylate (Preparation 5) (450 mg, 1.474 mmol) was added and the reaction mixture stirred at RT for 1 hour. There was still some 3-cyano-4-[(1-methylethyl)oxy]benzoic acid acid present. Further quantities of EDC (100 mg) and 1,1-Dimethylethyl 7-[(hydroxyamino)(imino)methyl]-1,3,4,5-tetrahydro-2H-2-benzazepine-2-carboxylate (100 mg) were added and the reaction stirred for 1 hour. Then the reaction was heated at 80° C. for 3 hours and left standing overnight. The reaction was then heated at 90° C. for 1 hour. EtOAc (70 ml) was added and the reaction mixture washed with sat. $NaHCO_3$ (50 ml) and water (2×70 ml), dried over anhydrous MgSO4 and evaporated. The crude material obtained was subjected to biotage chromatography (EtOAc/hexane 1:2), yielding a white solid on evaporation. Trituration with ether yielded the title compound (320 mg) as a white solid. NMR (400 MHz, $d_6$DMSO) 1.31 (9H, s), 1.38 (6H, d), 1.69 (2H, br. s), 3.06 (2H, broad s), 3.65 (2H, br. s), 4.44 (2H, s), 4.94-5.03 (1H, m), 7.38-7.43 (1H, m), 7.56 (1H, d), 7.84-7.91 (2H, m), 8.40 (1H, dd), 8.50 (1H, d)

Preparation 10

1,1-Dimethylethyl [7-(5-{3-cyano-4-[(1-methylethyl)oxy]phenyl}-1,2,4-oxadiazol-3-yl)-1,3,4,5-tetrahydro-2H-2-benzazepin-2-yl]acetate

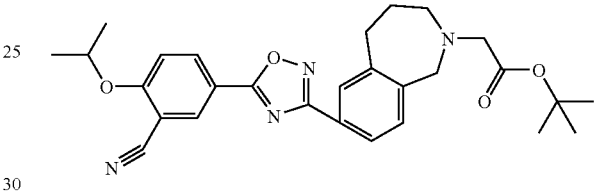

2-[(1-Methylethyl)oxy]-5-[3-(2,3,4,5-tetrahydro-1H-2-benzazepin-7-yl)-1,2,4-oxadiazol-5-yl]benzonitrile hydrochloride (Example 3) (70 mg, 0.170 mmol) and caesium carbonate (167 mg, 0.511 mmol) in dry DMF (5 ml) were treated with tert-butyl bromoacetate (0.038 ml, 0.256 mmol) and stirred at RT for 3 hours to give a single product. EtOAc (40 ml) was added and the mixture washed with water (2×50 ml), dried over anhydrous $MgSO_4$ and evaporated to yield the title compound (85 mg) as a clear, colourless oil. MS (ES) $C_{28}H_{32}N_4O_4$ requires 488; found 489 $(M+H)^+$.

Preparation 11

Ethyl 4-[7-(5-{3-cyano-4-[(1-methylethyl)oxy]phenyl}-1,2,4-oxadiazol-3-yl)-1,3,4,5-tetrahydro-2H-2-benzazepin-2-yl]butanoate

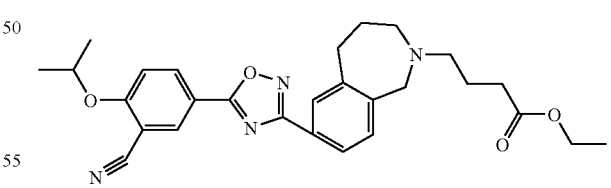

2-[(1-Methylethyl)oxy]-5-[3-(2,3,4,5-tetrahydro-1H-2-benzazepin-7-yl)-1,2,4-oxadiazol-5-yl]benzonitrile hydrochloride (Example 3) (70 mg, 0.170 mmol) and caesium carbonate (167 mg, 0.511 mmol) in dry DMF (5 ml) were treated with ethyl 4-bromobutyrate (0.037 ml, 0.256 mmol) and stirred at 60° C. for 2 hours. Additional quantities of ethyl 4-bromobutyrate (37 ul) were added and the reaction heated at 60° C. for 3 hours. The reaction was left standing overnight. EtOAc (50 ml) was added and the mixture washed with water (2×60 ml), dried over anhydrous $MgSO_4$ and evaporated to yield the title compound (90 mg) as a clear, colourless oil. MS (ES) $C_{28}H_{32}N_4O_4$ requires 488; found 489.0 $(M+H)^+$.

Preparation 12

1,1-Dimethylethyl 3-[7-(5-{3-cyano-4-[(1-methylethyl)oxy]phenyl}-1,2,4-oxadiazol-3-yl)-1,3,4,5-tetrahydro-2H-2-benzazepin-2-yl]propan-oate

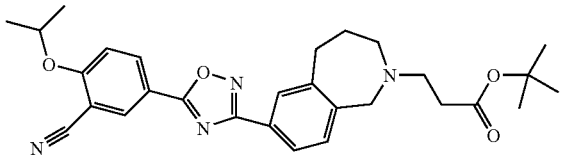

2-[(1-Methylethyl)oxy]-5-[3-(2,3,4,5-tetrahydro-1H-2-benzazepin-7-yl)-1,2,4-oxadiazol-5-yl]benzonitrile hydrochloride (Example 3) (70 mg, 0.170 mmol) and caesium carbonate (167 mg, 0.511 mmol) were stirred in dry DMF (5 ml) and treated with 1,1-dimethylethyl 3-bromopropanoate (0.043 ml, 0.256 mmol) then stirred at 60° C. for 2 hours. Further quantities of 1,1-dimethylethyl 3-bromopropanoate (44 µl) were added and the reaction stirred at 60° C. for 3 hours. The reaction was left standing overnight. 1,1-Dimethylethyl 3-bromopropanoate (43 µl) was added and the reaction mixture stirred at 60° C. for 7 hours then left standing overnight. EtOAc (50 ml) was added and the reaction mixture washed with water (2×50 ml), dried over anhydrous $MgSO_4$ and evaporated to yield a clear, colourless oil (100 mg). The oil slowly solidified. Trituration with ether/hexane to yielded the title compound (70 mg) as a white solid. MS (ES) $C_{29}H_{34}N_4O_4$ requires 502; found 503.0 (M+H).

Preparation 13

1,1-Dimethylethyl 6-{[(trifluoromethyl)sulfonyl]oxy}-1,2,4,5-tetrahydro-3H-3-benzazepine-3-carboxylate

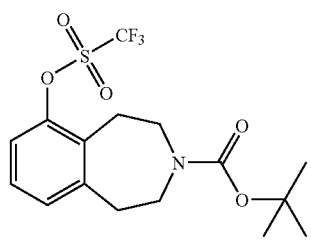

To a stirred solution of 1,1-dimethylethyl 6-hydroxy-1,2,4,5-tetrahydro-3H-3-benzazepine-3-carboxylate (may be prepared as described in WO2006/002928) (6.545 g) in dry DCM (100 ml) under argon at −10° C. was added triethylamine (4 ml). After 10 minutes trifluoromethanesulfonic anhydride (4.7 ml) was added dropwise over 10 minutes. The colourless solution turned amber then red. The reaction was allowed to reach RT over 30 minutes then stirred at RT for 18 hours. Then the reaction was poured onto saturated sodium carbonate solution (100 ml) and the DCM layer collected, dried and evaporated. The title compound (5 g) was obtained by chromatography (eluting with DCM). δH (400 MHz, CDCl$_3$) 7.22-7.12 (3H, m), 3.59-3.57 (4H, m), 3.01-2.99 (4H, m), 1.48 (9H, s); MS (ES) $C_{16}H_{20}F_3NO_5S$ requires 395; found 340 $[M+H-56]^+$.

Preparation 14

1,1-Dimethylethyl 6-cyano-1,2,4,5-tetrahydro-3H-3-benzazepine-3-carboxylate

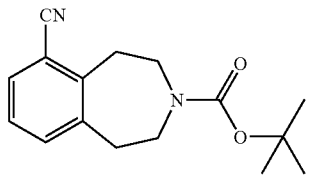

1,1-dimethylethyl 6-{[(trifluoromethyl)sulfonyl]oxy}-1,2,4,5-tetrahydro-3H-3-benzazepine-3-carboxylate (Preparation 13) (5 g), zinc (II) cyanide (1.5 g) and tetrakis(triphenylphoshine)palladium(0) (1.5 g) were heated in dry DMF at 150° C. for 18 hours. The cooled reaction mixture was diluted with EtOAc (200 ml) and filtered. The filtrate was washed with saturated sodium bicarbonate, (200 ml), water (200 ml) and brine (200 ml). The crude reaction mixture was dried in the usual manner and evaporated. Purification by chromatography (eluting with DCM) yielded the title compound (3.4 g). δH (400 MHz, CDCl$_3$) 7.50 (1H, d), 7.35 (1H, d), 7.27-7.21 (1H), m), 3.62-3.56 (4H, m), 3.22-3.20 (2H, m), 2.97-2.94 (2H, m), 1.47 (9H, s); MS (ES) $C_{16}H_{20}N_2O_2$ requires 272; found 217 $[M+H-56]^+$, 273 $[M+H]^+$.

Preparation 15

1,1-Dimethylethyl 6-[(hydroxyamino)(imino)methyl]-1,2,4,5-tetrahydro-3H-3-benzazepine-3-carboxylate

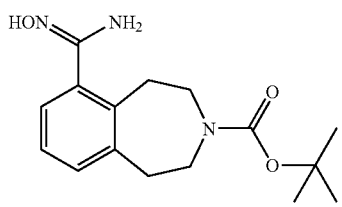

1,1-dimethylethyl 6-cyano-1,2,4,5-tetrahydro-3H-3-benzazepine-3-carboxylate (Preparation 14) (1.15 g), hydroxylamine hydrochloride (1.18 g) and sodium bicarbonate (1.76 g) were heated at 60° C. in ethanol (100 ml) for 18 hours under argon. The cooled reaction was evaporated to dryness, partitioned between DCM (100 ml) and water (100 ml). The DCM layer was collected and the water layer washed with DCM (50 ml). The combined DCM layers were dried and evaporated. The title compound (506 mg) was isolated by chromatography eluting with 5% methanol in DCM. δH (400 MHz, CDCl$_3$) 7.27 (1H, s) 7.16-7.13 (2H, m), 5.38 (1H, br. s), 3.58-3.55 (4H, m), 3.05 (2H, br. s), 2.89 (2H, br. s) 1.46 (2H br. s), 1.12 (9H, br. s); MS (ES) $C_{16}H_{23}N_3O_3$ requires 305; found 306 $[M+H]^+$.

Preparation 16

1,1-Dimethylethyl 6-(5-{3-cyano-4-[(1-methylethyl)oxy]phenyl}-1,2,4-oxadiazol-3-yl)-1,2,4,5-tetrahydro-3H-3-benzazepine-3-carboxylate

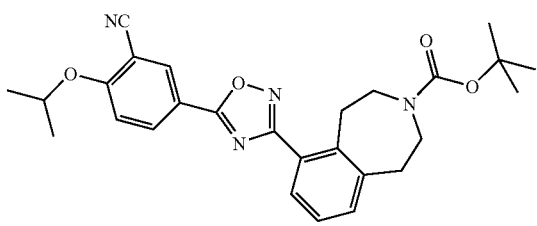

1,1-Dimethylethyl 6-[(hydroxyamino)(imino)methyl]-1,2,4,5-tetrahydro-3H-3-benzazepine-3-carboxylate (Preparation 15) (360 mg, 1.179 mmol) was dissolved in THF (50 ml) and stirred with sodium hydride (60% dispersion in mineral oil, 51.9 mg, 1.297 mmol) under argon at room temperature for 30 minutes. Then methyl 3-cyano-4-[(1-methylethyl)oxy]benzoate (may be prepared as described in WO2005058848) (388 mg, 1.768 mmol) was added as a THF solution (5 ml) and the reaction heated at reflux temperature for 1.5 hours. The cooled reaction was evaporated and partitioned between DCM (100 ml) and water (100 ml). The water layer was washed with DCM (50 ml) and the combined DCM layers dried (hydrophobic frit) and evaporated. The product was isolated by silica chromatography (eluting with DCM) to give 1,1-dimethylethyl 6-(5-{3-cyano-4-[(1-methylethyl)oxy]phenyl}-1,2,4-oxadiazol-3-yl)-1,2,4,5-tetrahydro-3H-3-benzazepine-3-carboxylate (505 mg, 1.011 mmol, 86% yield) as a white foam. δH (400 MHz, CDCl$_3$) 8.41 (1H, s), 8.33 (1H, dd), 7.7 (1H, dd), 7.31-7.25 (2H, m), 7.13 (1H, d), 4.80 (1H, sept), 3.63-3.62 (4H, m), 3.3-3.2 (2H, m), 2.95-3.05 (2H, m), 1.47 (6H, d), 1.43 (9H, br.s); MS (ES) C$_{27}$H$_{30}$N$_4$O$_4$ requires 474; found 475 [M+H]$^+$.

Preparation 17

1,1-Dimethylethyl 6-(5-{3-chloro-4-[(1-methylethyl)oxy]phenyl}-1,2,4-oxadiazol-3-yl)-1,2,4,5-tetrahydro-3H-3-benzazepine-3-carboxylate

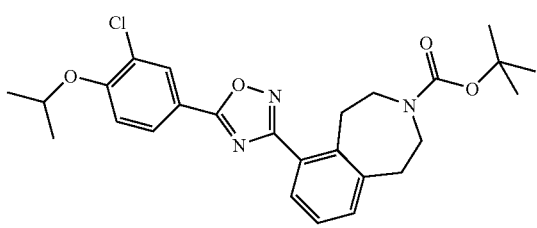

1,1-dimethylethyl 6-[(hydroxyamino)(imino)methyl]-1,2,4,5-tetrahydro-3H-3-benzazepine-3-carboxylate (Preparation 15) (170 mg, 0.557 mmol) was dissolved in THF (30 ml) and stirred with sodium hydride (24.49 mg, 0.612 mmol) under argon at room temperature for 30 minutes. Then methyl 3-chloro-4-[(1-methylethyl)oxy]benzoate (may be prepared as described in WO2005058848) (191 mg, 0.835 mmol) was added and the reaction heated at reflux temperature for 1.5 hours. The cooled reaction was evaporated and partitioned between DCM (100 ml) and water (100 ml). The water layer was washed with DCM (50 ml) and the combined DCM layers dried (hydrophobic frit) and evaporated. The title compound was isolated by silica chromatography (eluting with DCM). 1,1-dimethylethyl 6-(5-{3-chloro-4-[(1-methylethyl)oxy]phenyl}-1,2,4-oxadiazol-3-yl)-1,2,4,5-tetrahydro-3H-3-benzazepine-3-carboxylate (260 mg, 0.537 mmol, 96% yield) was isolated as an off-white foam. δH (400 MHz, CDCl$_3$) 8.22 (1H, s), 8.05 (1H d), 7.68 (1H, d), 7.30-7.24 (2H, m), 7.06 (1H, d), 4.72 (1H, sept), 3.65-3.55 (4H, m), 3.35-3.25 (2H, m), 2.95-3.05 (2H, m); 1.45 (6H, d), 1.43 (9H, s); MS (ES) C$_{26}$H$_{30}$$^{35}$ClN$_3$O$_4$ requires 483; found 484 [M+H]$^+$.

Preparation 18

1,1-Dimethylethyl 3-[6-(5-{3-chloro-4-[(1-methylethyl)oxy]phenyl}-1,2,4-oxadiazol-3-yl)-1,2,4,5-tetrahydro-3H-3-benzazepin-3-yl]propan-oate

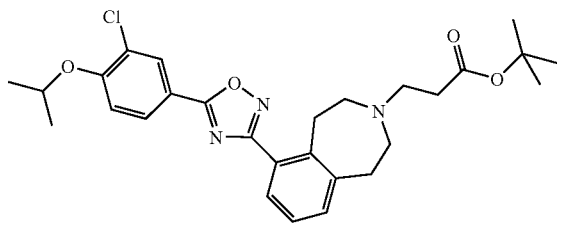

In a 5 ml microwave reaction vessel was added 6-(5-{3-chloro-4-[(1-methyl ethyl)oxy]phenyl}-1,2,4-oxadiazol-3-yl)-2,3,4,5-tetrahydro-1H-3-benzazepine (Free base of Example 8, obtained by standard methods e.g. partitioning between organic and basic aqueous solvents and collecting organic solvent) (70 mg) in DMF (3 ml) to give a brown solution. Then potassium carbonate (101 mg) was added followed by 1,1-dimethylethyl 3-bromopropanoate (38.1 mg, 0.182 mmol). The reaction mixture was heated at 100° C. for 10 minutes. The cooled reaction mixture was diluted with DCM (5 ml) and purified by SCX (washing with methanol and eluting the crude amino ester with methanolic ammonia). Purification by MDAP yielded the amino ester, 1,1-dimethylethyl 3-[6-(5-{3-chloro-4-[(1-methylethyl)oxy]phenyl}-1,2,4-oxadiazol-3-yl)-1,2,4,5-tetrahydro-3H-3-benzazepin-3-yl]propanoate (25 mg, 0.046 mmol, 25.4% yield) isolated as a light yellow oil. MS (ES) C$_{28}$H$_{34}$$^{35}$ClN$_3$O$_4$ requires 511; found 512 [M+H]$^+$.

Preparation 19

1,1-Dimethylethyl [6-(5-{3-chloro-4-[(1-methylethyl)oxy]phenyl}-1,2,4-oxadiazol-3-yl)-1,2,4,5-tetrahydro-3H-3-benzazepin-3-yl]acetate

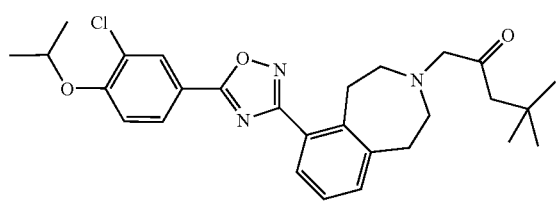

In a 5 ml microwave reaction vessel was added 6-(5-{3-chloro-4-[(1-methylethyl)oxy]phenyl}-1,2,4-oxadiazol-3-yl)-2,3,4,5-tetrahydro-1H-3-benzazepine hydrochloride (Example 8) (110 mg, 0.262 mmol). Then potassium carbonate (101 mg) was added followed by 1,1-dimethylethyl bromoacetate (51.0 mg, 0.262 mmol). The reaction mixture was heated at 100° C. for 10 minutes. The cooled reaction mixture was diluted with DCM (5 ml) and purified by SCX (washing with methanol and eluting the crude amino ester with methanolic ammonia). 1,1-dimethylethyl [6-(5-{3-chloro-4-[(1-methylethyl)oxy]phenyl}-1,2,4-oxadiazol-3-yl)-1,2,4,5-tetrahydro-3H-3-benzazepin-3-yl]acetate (120 mg, 0.241 mmol, 92% yield) was isolated as a pale yellow oil. MS (ES) $C_{27}H_{32}{}^{35}ClN_3O_4$ requires 497; found 498 $[M+H]^+$.

Preparation 20

3-Cyano-N-hydroxy-2-methylbenzenecarboximidamide

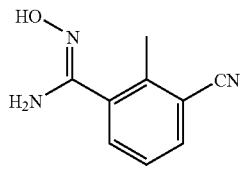

A suspension of 2,6-dicyanotoluene (25.0 g, 176 mmol), hydroxylamine hydrochloride (73.0 g, 1.06 mol) and triethylamine (142 g, 1.41 mol) in chloroform (500 ml) was stirred at 50° C. for 7 h, then allowed to stand at room temperature overnight. The reaction mixture was cooled in ice, treated with 5M HCl to pH1 and extracted three times with chloroform. The aqueous was extracted with THF (×7), cooled in ice, raised to pH4 with 40% NaOH and extracted with THF (×3). The latter THF extracts were combined and evaporated to dryness to give a buff solid consisting of the product and approximately a third of an equivalent of triethylamine (11.0 g). $^1H$ NMR (400 MHz, $d_4$-MeOH) δ (inter alia) 7.70-7.76 (1H, m), 7.57-7.63 (1H, m), 7.35-7.62 (1H, m), 2.58 (3H, s); MS (ES) $C_9H_9N_3O$ requires 175; found 176 $[M+H]^+$. The former seven extracts of THF were combined, evaporated to dryness and dissolved in water. The aqueous solution was extracted twice with chloroform, adjusted to pH4 and extracted with THF (×3). Evaporation of the combined THF extracts gave a further 4.5 g of product.

Preparation 21

3-(5-{3-Chloro-4-[(1-methylethyl)oxy]phenyl}-1,2,4-oxadiazol-3-yl)-2-methylbenzonitrile

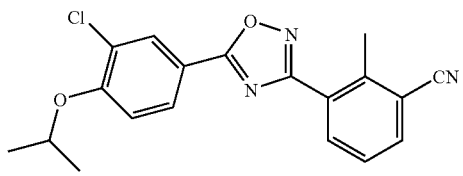

To a solution of 3-cyano-N-hydroxy-2-methylbenzenecarboximidamide (Preparation 20) (1.70 g, 9.70 mmol) in THF (100 ml) was added sodium hydride (0.427 g, 10.67 mmol) under argon at rt and the suspension stirred for 30 min. Then methyl 3-chloro-4-[(1-methylethyl)oxy]benzoate (may be prepared as described in WO2005058848) (3.33 g, 14.56 mmol) was added and reaction heated at reflux for 45 minutes, then cooled to RT and stirred for 3 days.

Separately, to a suspension of 3-cyano-N-hydroxy-2-methylbenzenecarboximidamide (Preparation 20) (10.48 g, 59.8 mmol) in THF (250 ml) under argon at rt was added sodium hydride (2.87 g, 71.8 mmol) portionwise and the resulting suspension stirred at RT for 30 minutes. Methyl 3-chloro-4-[(1-methylethyl)oxy]benzoate (19.9 g, 87 mmol) was added and reaction heated at reflux for 4 h, then stirred at rt for 16 h.

The two reaction mixtures were combined. Water (200 ml) was added then the mixture extracted with DCM (2×250 ml). The organic layers were combined, washed with brine (100 ml) and concentrated in vacuo to give a crude white solid (28.1 g). The solid was redissolved in DCM (200 ml), THF (150 ml) and EtOH (50 ml) and passed through a short plug of silica (1 cm deep). Elution with DCM followed by concentration in vacuo gave a pale yellow solid 3-(5-{3-chloro-4-[(1-methylethyl)oxy]phenyl}-1,2,4-oxadiazol-3-yl)-2-methylbenzonitrile (18.10 g, 51.2 mmol, 80% yield). Elution of the silica with DCM-EtOH (2:1) followed by concentration in vacuo gave a pale yellow solid 3-(5-{3-chloro-4-[(1-methylethyl)oxy]phenyl}-1,2,4-oxadiazol-3-yl)-2-methylbenzonitrile (2.81 g, 6.35 mmol, 10% yield). Both batches were analytically identical. $^1H$ NMR (400 MHz, $CDCl_3$) δ 8.27 (1H, d), 8.22 (1H, d), 8.05 (1H, dd), 7.77 (1H, d), 7.45 (1H, t), 7.07 (1H, d), 4.73 (1H, sept), 2.90 (3H, s), 1.47 (6H, d); MS (ES) $C_{19}H_{16}{}^{35}ClN_3O_2$ requires 353; found 354 $[M+H]^+$.

Preparation 22

2-(3-Buten-1-yl)-3-(5-{3-chloro-4-[(1-methylethyl)oxy]phenyl}-1,2,4-oxadiazol-3-yl)benzonitrile

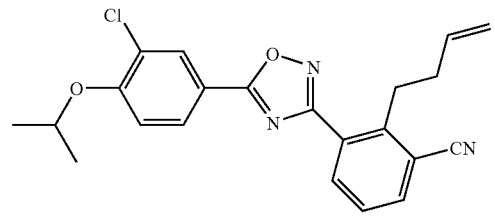

To a solution of diisopropylamine (15.15 ml, 106 mmol) in dry THF (650 m) at −78° C. under Ar was added ″BuLi (44.3 ml, 70.9 mmol) down the side of the flask and the resulting solution stirred for 1 h. A solution of 3-(5-{3-chloro-4-[(1-methylethyl)oxy]phenyl}-1,2,4-oxadiazol-3-yl)-2-methylbenzonitrile Preparation 21) (12.54 g, 35.4 mmol) in dry THF (100 ml) under Ar was added dropwise at ~10 mlmin$^{-1}$, and the resulting dark blue solution stirred at −78° C. for 45 min. Allyl bromide (6.13 ml, 70.9 mmol) was added dropwise at ~3 mlmin$^{-1}$, and the resulting dark red solution stirred for 30 min at −78° C. 1 M HCl (aq) (375 ml) was added, the mixture allowed to warm to RT then the layers separated. The aqueous was extracted with EtOAc (2×125 ml), then the combined organics washed with brine (250 ml), dried ($MgSO_4$), filtered and concentrated in vacuo to give a crude red oil (12.8 g). This was redissolved in DCM (20 ml) and added to a pre-wet (isohexane) column of silica (5 cm×5 cm). Elution with EtOAc-isohexane (1:3) and concentration of the desired fractions gave a pale orange solid 2-(3-buten-1-yl)-3-(5-{3-chloro-4-[(1-methylethyl)oxy]phenyl}-1,2,4-oxadiazol-3-yl)benzonitrile (9.50 g, 20.98 mmol, 59.2% yield). $^1H$ NMR (400 MHz, $CDCl_3$) δ 8.26 (1H, d), 8.24 (1H, d), 8.05 (1H, dd), 7.79 (1H, d), 7.46 (1H, t), 7.07 (1H, d), 5.94 (1H, ddt), 5.07 (1H, dq), 5.01 (1H, dd), 4.73 (1H, sept), 3.40 (2H, t), 2.47 (2H, qd), 1.45 (6H, d); MS (ES) $C_{22}H_{20}{}^{35}ClN_3O_2$ requires 393; found 394 $[M+H]^+$.

Preparation 23

3-[2-(Aminomethyl)-6-(5-{3-chloro-4-[(1-methylethyl)oxy]phenyl}-1,2,4-oxadiazol-3-yl)phenyl]-1-propanol

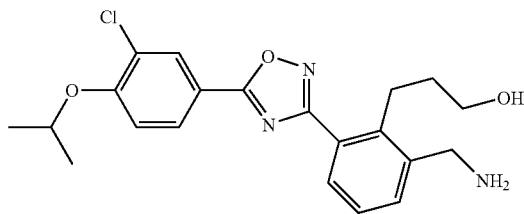

Through a solution of 2-(3-buten-1-yl)-3-(5-{3-chloro-4-[(1-methylethyl)oxy]phenyl}-1,2,4-oxadiazol-3-yl)benzonitrile (Preparation 22) (8.26 g, 20.97 mmol) in DCM (125 ml) under Ar at −78° C. was bubbled Ar then $O_2$ (5 min each). The ozonoliser (model 502; 75 lh$^{-1}$; 0.3 A) was switched on and the orange solution ozonolised until it had turned an opaque green-grey colour (3 hrs). The ozonoliser was switched off, and $O_2$, then Ar bubbled though the solution (10 min each). The solution was allowed to warm to RT under Ar, then concentrated in vacuo to give an opaque yellow oil. This was redissolved in dry THF (200 ml), BH$_3$.DMS (9.96 ml, 105 mmol) added (CARE: gas evolution), and the solution stirred at RT for 18 hrs and then at 40° C. for 3 hrs. The reaction was cooled to 0° C., then 0.1M aqueous HCl (150 ml) was added cautiously (CARE: gas evolution), then allowed to stir at RT for 18 hrs. The solution was passed directly down an SCX-2 column (50 g), washing with MeOH. The product was eluted with 0.5M NH$_3$ in MeOH; concentration in vacuo gave an orange foam 3-[2-(aminomethyl)-6-(5-{3-chloro-4-[(1-methylethyl)oxy]phenyl}-1,2,4-oxadiazol-3-yl)phenyl]-1-propanol (2.73 g, 3.95 mmol, 18.9% yield). $^1$H NMR (400 MHz, CDCl$_3$) δ (inter alia) 8.23 (1H, d), 8.05 (1H, dd), 7.86 (1H, d), 7.46 (1H, d), 7.34 (1H, t), 7.06 (1H, d), 4.72 (1H, sept), 4.03 (2H, s), 3.47 (2H, t), 3.27 (2H, t), 1.78 (2H, quin), 1.45 (6H, d); MS (ES) $C_{21}H_{24}{}^{35}ClN_3O_3$ requires 401; found 402 $[M+H]^+$.

Preparation 24

1,1-Dimethylethyl [6-(5-{3-chloro-4-[(1-methylethyl)oxy]phenyl}-1,2,4-oxadiazol-3-yl)-1,3,4,5-tetrahydro-2H-2-benzazepin-2-yl]acetate

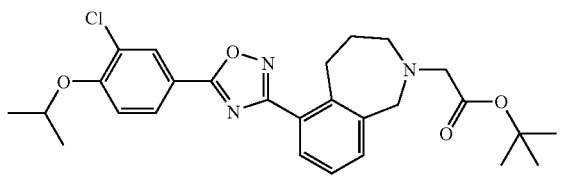

To a solution of 3-[2-(aminomethyl)-6-(5-{3-chloro-4-[(1-methylethyl)oxy]phenyl}-1,2,4-oxadiazol-3-yl)phenyl]-1-propanol (Preparation 23) (424 mg, 1.055 mmol) and triphenylphosphine (1384 mg, 5.28 mmol) in dry DCM (150 ml) at RT under Ar was added DIAD (0.974 ml, 5.01 mmol) dropwise over 2 min and the resulting pale yellow solution stirred at RT for 2 hrs. The solution was concentrated to ~10 ml, then passed down an SCX-2 cartridge (10 g), washing with MeOH. The product was eluted with 0.5M NH$_3$ in MeOH; concentration in vacuo gave a pale orange oil (>900 mg). SCX-2 purification was repeated to remove remaining triphenylphosphine oxide to give a pale yellow oil (314 mg). The oil was redissolved in DCM (40 ml), BOC$_2$O (0.367 ml, 1.583 mmol) and DMAP (6.44 mg, 0.053 mmol) added sequentially and stirred under Ar for 2 hrs. Saturated aqueous NH$_4$Cl (20 ml) was added then the aqueous extracted with DCM (25 ml). The organic layers were combined, passed through a hydrophobic frit and concentrated in vacuo to give a crude pale brown oil (496 mg). Flash chromatography (silica; Flash 25M; linear gradient (0.1-1%) MeOH in DCM) gave a yellow oil 1,1-dimethylethyl 6-(5-{3-chloro-4-[(1-methylethyl)oxy]phenyl}-1,2,4-oxadiazol-3-yl)-1,3,4,5-tetrahydro-2H-2-benzazepine-2-carboxylate (130 mg). This material was redissolved in 4 M HCl in dioxane (5 ml, 20.00 mmol) and stirred at RT for 3 hrs. The solution was added to an SCX-3 column (10 g) and washed with MeOH. The product was eluted with 0.5 M NH$_3$ in MeOH; concentration in vacuo gave a pale white solid (102 mg). The product was redissolved in dry DMF (3 ml); potassium carbonate (74.1 mg, 0.536 mmol) and tert-butyl bromoacetate (0.042 ml, 0.281 mmol) were added, then the suspension irradiated to 100° C. for 10 min in the microwave. The mixture was diluted with DCM (7 ml), then added to an SCX-3 cartridge (10 g) and washed with MeOH. The product was eluted with 0.5 M NH$_3$ in MeOH; concentration in vacuo gave an orange oil (57 mg). Reverse-phase mass-directed auto-purification (MDAP) gave the product in a water-MeCN solution. The desired fractions were added to an SCX-3 cartridge (1 g) and washed with MeOH. The product was eluted with 0.5 M NH$_3$ in MeOH; concentration in vacuo gave a clear film (21.4 mg) a 5:2 ratio mixture of 1,1-dimethylethyl [6-(5-{3-chloro-4-[(1-methylethyl)oxy]phenyl}-1,2,4-oxadiazol-3-yl)-1,3,4,5-tetrahydro-2H-2-benzazepin-2-yl]acetate and [6-(5-{3-chloro-4-[(1-methylethyl)oxy]phenyl}-1,2,4-oxadiazol-3-yl)-1,3,4,5-tetrahydro-2H-2-benzazepin-2-yl]acetic acid. Major component: $^1$H NMR (400 MHz, CDCl$_3$) δ 8.22 (1H, d), 8.05 (1H, dd), 7.68 (1H, d), 7.26 (1H, d), 7.25 (1H, t), 7.06 (1H, d), 4.72 (1H, sept), 4.14 (2H, s), 3.28 (2H, br s), 3.23 (2H, t), 3.16 (2H, s), 1.77 (2H, m), 1.47 (9H, s), 1.43 (6H, d); MS (ES) $C_{27}H_{32}{}^{35}ClN_3O_4$ requires 497; found 498 $[M+H]^+$.

Preparation 25

8-(Methyloxy)-3,4-dihydro-1,4-benzoxazepin-5(2H)-one

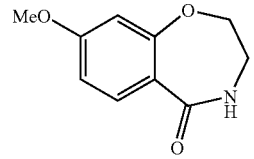

DIAD (32.1 ml, 165 mmol) was added dropwise over 15 mins to a stirred, ice-cooled solution of methyl 2-hydroxy-4-(methyloxy)benzoate (24.18 g, 150 mmol), 1,1-dimethylethyl (2-hydroxyethyl)carbamate (27.3 g, 150 mmol) and triphenylphosphine (43.3 g, 165 mmol) in THF (450 ml) then stirred and allowed to warm to room temperature over 2 hours. The reaction mixture was evaporated to give 129.9 g of a viscous yellow oil. Trifluoroacetic acid (60 ml, 779 mmol) in dichloromethane (DCM) (350 ml) were added and the reaction left at room temperature for 65 hours then evaporated to dryness. The resultant residue was dissolved in 500 ml of ether and extracted with 2M HCl (200 ml and 2×75 ml). Combined acid extracts were washed with 200 ml of ether then 500 g of ice added along with 250 ml of EtOAc and the mixture basified with 50% sodium hydroxide with vigorous stirring. The organics were separated and the aqueous further extracted with 4×75 ml of EtOAc and the combined organics dried (magnesium sulphate) and evaporated to give 21.1 g of a yellow oil. The oil was dissolved in toluene (350 ml) and stirred and refluxed for 24 hours then evaporated and purified by flash chromatography eluting with EtOAc to give the title compound (8.61 g) as a white solid. MS (ES) $C_{10}H_{11}NO_3$ requires 193; found 194 $[M+H]^+$.

Preparation 26

8-Hydroxy-3,4-dihydro-1,4-benzoxazepin-5(2H)-one

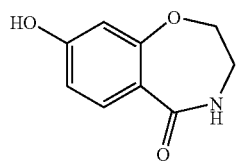

A mixture of 8-(methyloxy)-3,4-dihydro-1,4-benzoxazepin-5(2H)-one (Preparation 25) (7.98 g, 41.3 mmol) and hydrobromic acid (100 ml, 1842 mmol) was stirred and heated at 110° C. for 7 hours. Then the reaction mixture was evaporated and azeotroped twice with 150 ml of ethanol to give the title compound (8.66 g) light brown solid which was used without purification. MS (ES) $C_9H_9NO_3$ requires 179; found 180 $[M+H]^+$.

Preparation 27

8-[(Phenylmethyl)oxy]-3,4-dihydro-1,4-benzoxazepin-5(2H)-one

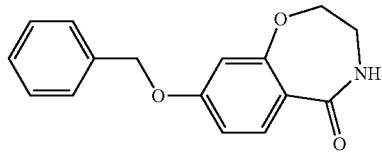

A mixture of 8-hydroxy-3,4-dihydro-1,4-benzoxazepin-5(2H)-one (Preparation 26) (8.66 g, 48.3 mmol), benzyl bromide (6.32 ml, 53.2 mmol) and potassium carbonate (20.04 g, 145 mmol) in DMF (80 ml) was stirred and heated at 60° C. for 2 hours. The cooled reaction was diluted with EtOAc/water (300 ml of each) and the aqueous extracted with EtOAc (2×75 ml). Combined organics were washed with 3×100 ml of water, dried (magnesium sulphate), evaporated, triturated with ether and filtered off to give the title compound (8.39 g) as a white solid. MS (ES) $C_{16}H_{15}NO_3$ requires 269; found 270 $[M+H]^+$.

Preparation 28

8-[(Phenylmethyl)oxy]-2,3,4,5-tetrahydro-1,4-benzoxazepine

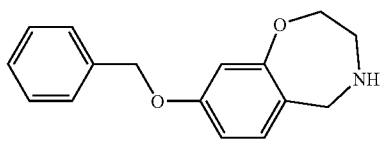

1M Lithium aluminium hydride (62.4 ml, 62.4 mmol) in THF was added under argon to a stirred solution of 8-[(phenylmethyl)oxy]-3,4-dihydro-1,4-benzoxazepin-5(2H)-one (Preparation 27) (8.39 g, 31.2 mmol) in THF (150 ml) with ice bath cooling over 5 minutes. The resulting solution was heated with stirring at 60° C. for 3 hours. The reaction was cooled and carefully quenched by slow addition with ice cooling of 150 ml of 2M sodium hydroxide followed by 150 ml of EtOAc. The organics were separated and aqueous extracted with 100 ml of EtOAc. The combined organic extracts were dried (magnesium sulphate) and evaporated to give the title compound (7.53 g) as a light coloured oil. MS (ES) $C_{16}H_{17}NO_2$ requires 255; found 256 $[M+H]^+$.

Preparation 29

1,1-Dimethylethyl 8-[(phenylmethyl)oxy]-2,3-dihydro-1,4-benzoxazepine-4(5H)-carboxylate

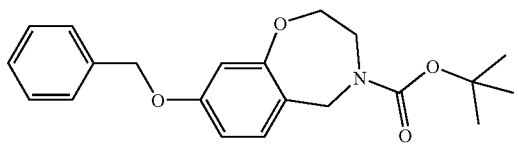

BOC$_2$O (7.52 ml, 32.4 mmol) was added to a solution of 8-[(phenylmethyl)oxy]-2,3,4,5-tetrahydro-1,4-benzoxazepine (Preparation 28) (7.52 g, 29.5 mmol) in DCM (100 ml) and kept at room temperature for 30 minutes. Then the reaction was evaporated to dryness and purified by flash chromatography eluting with 5% EtOAc in iso-hexane changing to 15% EtOAc in iso-hexane to elute product. Triturated with iso-hexane and filtered off to give 7.37 g of white solid. MS (ES) $C_{21}H_{25}NO_4$ requires 355; found 300 $[M+H-56]^+$.

Preparation 30

1,1-Dimethylethyl 8-hydroxy-2,3-dihydro-1,4-benzoxazepine-4(5H)-carboxylate

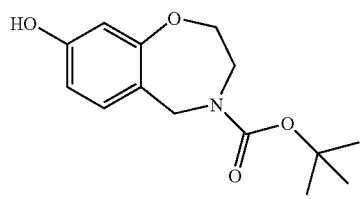

1,1-Dimethylethyl 8-[(phenylmethyl)oxy]-2,3-dihydro-1,4-benzoxazepine-4(5H)-carboxylate (Preparation 29) (7.35 g, 20.68 mmol) in a mixture of THF (40 ml) and EtOH (40 ml) was hydrogenated with 10% palladium on carbon (0.735 g, 6.91 mmol) for 18 hours then filtered and evaporated to give the title compound (5.49 g) as a white solid. MS (ES) $C_{14}H_{19}NO_4$ requires 265; found 166 [M+H−100]$^+$.

Preparation 31

1,1-Dimethylethyl 8-{[(trifluoromethyl)sulfonyl]oxy}-2,3-dihydro-1,4-benzoxazepine-4(5H)-carboxylate

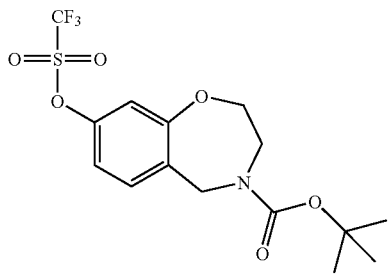

Trifluoromethanesulfonic anhydride (0.253 ml, 1.498 mmol) was added to an ice cooled solution of 1,1-dimethylethyl 8-hydroxy-2,3-dihydro-1,4-benzoxazepine-4(5H)-carboxylate (Preparation 30) (0.265 g, 0.999 mmol) in pyridine (4 ml) and stirred for one hour. The reaction mixture was evaporated, dissolved in 40 ml of EtOAc and washed with 20 ml of 2M HCl and 20 ml of saturated sodium bicarbonate then dried (magnesium sulphate) and evaporated to give the title compound (399 mgs) as a yellow gum. MS (ES) $C_{15}H_{18}F_3NO_6S$ requires 397; found 298 [M+H−100]$^+$.

Preparation 32

1,1-Dimethylethyl 8-cyano-2,3-dihydro-1,4-benzoxazepine-4(5H)-carboxylate

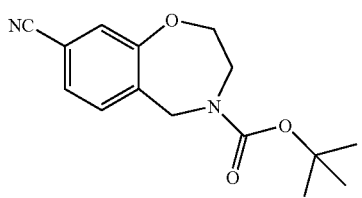

A mixture of 1,1-dimethylethyl 8-{[(trifluoromethyl)sulfonyl]oxy}-2,3-dihydro-1,4-benzoxazepine-4(5H)-carboxylate (Preparation 31) (0.397 g, 0.999 mmol), zinc cyanide (0.176 g, 1.499 mmol) and tetrakis(triphenylphosphine)palladium(0) (0.115 g, 0.100 mmol) in DMF (4 ml) was stirred and heated at 80° C. for 2 hours then cooled and diluted with EtOAc/water (40 ml of each) and the organic washed with 3×20 ml of water, dried (magnesium sulphate), evaporated and purified by flash chromatography eluting with 1:4 EtOAc/iso-hexane to give the title compound (198 mgs) as a gum which crystallised slowly. MS (ES) $C_{15}H_{18}N_2O_3$ requires 274; found 175 [M+H−100]$^+$.

Preparation 33

1,1-Dimethylethyl 8-[(hydroxyamino)(imino)methyl]-2,3-dihydro-1,4-benzoxazepine-4(5H)-carboxylate

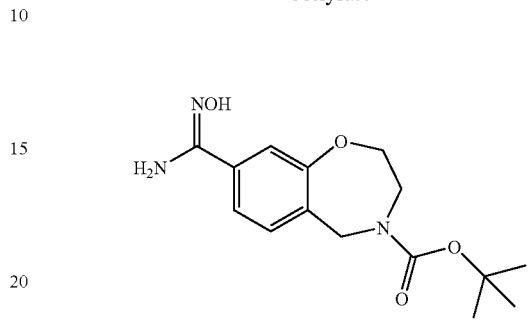

A mixture of 1,1-dimethylethyl 8-cyano-2,3-dihydro-1,4-benzoxazepine-4(5H)-carboxylate (Preparation 32) (0.195 g, 0.711 mmol), hydroxylamine hydrochloride (0.099 g, 1.422 mmol) and sodium bicarbonate (0.299 g, 3.55 mmol) in ethanol (5 ml) was stirred and heated at 60° C. for 3 hours. The reaction mixture was cooled, evaporated and dissolved in EtOAc/water (40 ml of each, some warming needed) and the organics dried (magnesium sulphate) and evaporated to give the title compound (210 mgs) as a white solid. MS (ES) $C_{15}H_{21}N_3O_4$ requires 307; found 308 [M+H]$^+$.

Preparation 34

1,1-Dimethylethyl 8-(5-{3-chloro-4-[(1-methylethyl)oxy]phenyl}-1,2,4-oxadiazol-3-yl)-2,3-dihydro-1,4-benzoxazepine-4(5H)-carboxylate

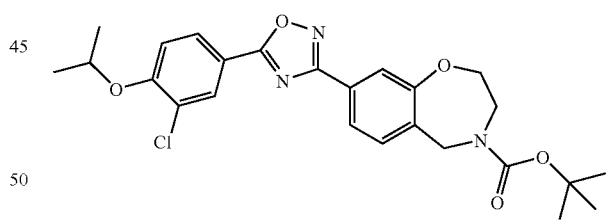

A mixture of 1,1-dimethylethyl 8-[(hydroxyamino)(imino)methyl]-2,3-dihydro-1,4-benzoxazepine-4(5H)-carboxylate (Preparation 33) (0.195 g, 0.634 mmol), 3-chloro-4-[(1-methylethyl)oxy]benzoic acid (Preparation 6) (0.136 g, 0.634 mmol), EDC (0.146 g, 0.761 mmol) and HOBT (0.107 g, 0.698 mmol) DMF (4 ml) was stirred at room temperature for 20 minutes then heated at 100° C. for 17 hours. The cooled reaction mixture was diluted with EtOAc/water (40 ml of each) and the organics collected, dried (magnesium sulphate), evaporated and purified by biotage chromatography in 1:4 EtOAc/iso-hexane to give the title compound (172 mgs) as a white solid. MS (ES) $C_{25}H_{28}{}^{35}ClN_3O_5$ requires 485; found 486 [M+H]$^+$; $C_{25}H_{28}{}^{37}ClN_3O_5$ requires 487; found 488 [M+H]$^+$.

Preparation 35

Ethyl 3-[8-(5-{3-chloro-4-[(1-methylethyl)oxy]phenyl}-1,2,4-oxadiazol-3-yl)-2,3-dihydro-1,4-benzoxazepin-4(5H)-yl]propanoate

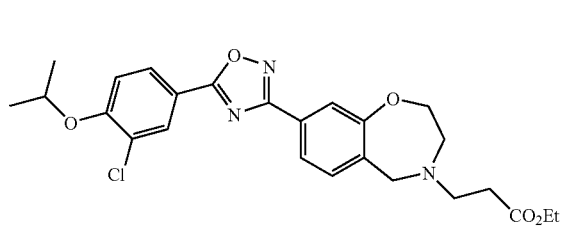

A mixture of 8-(5-{3-chloro-4-[(1-methylethyl)oxy]phenyl}-1,2,4-oxadiazol-3-yl)-2,3,4,5-tetrahydro-1,4-benzoxazepine (Example 13) (0.036 g, 0.199 mmol), ethyl 3-bromopropanoate (0.084 g, 0.199 mmol) and DIPEA (0.097 ml, 0.557 mmol) was stirred and heated at 80° C. for 4 hours when a further portion of ethyl 3-bromopropanoate (0.084 g, 0.199 mmol) and DIPEA (0.097 ml, 0.557 mmol) were added and heated overnight when a further portion of ethyl 3-bromopropanoate (0.084 g, 0.199 mmol) and DIPEA (0.097 ml, 0.557 mmol) were added and heated for 3 more hours when all starting material gone. The cooled reaction mixture was diluted with EtOAc/water (30 ml of each) and the organics dried (magnesium sulphate), evaporated and purified by flash chromatography eluting with 1:1 EtOAc/iso-hexane to give the title compound (90 mgs) as a colourless gum. MS (ES) $C_{25}H_{28}{}^{35}ClN_3O_5$ requires 485; found 486 $[M+H]^+$.

Preparation 36

Ethyl 4-[8-(5-{3-chloro-4-[(1-methylethyl)oxy]phenyl}-1,2,4-oxadiazol-3-yl)-2,3-dihydro-1,4-benzoxazepin-4(5H)-yl]butanoate

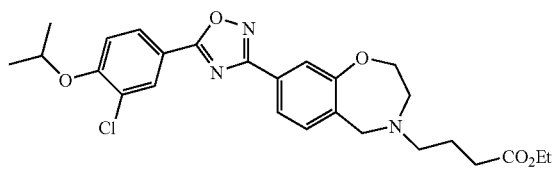

A mixture of 8-(5-{3-chloro-4-[(1-methylethyl)oxy]phenyl}-1,2,4-oxadiazol-3-yl)-2,3,4,5-tetrahydro-1,4-benzoxazepine (Example 13) (0.127 g, 0.3 mmol), DIPEA (0.052 ml, 0.300 mmol) and ethyl 4-bromobutanoate (0.059 g, 0.300 mmol) in acetonitrile (5 ml) was stirred and heated at 70° C. for 15 hours. The cooled reaction mixture was diluted and dissolved in EtOAc/water (30 ml of each) and the organics dried (magnesium sulphate), evaporated and purified by flash chromatography eluting with 1:1 EtOAc/iso-hexane to give the title compound (106 mgs) as a colourless gum. MS (ES) $C_{28}H_{38}{}^{35}ClN_3O_5$ requires 499; found 500 $[M+H]^+$.

Preparation 37

1,1-Dimethylethyl [8-(5-{3-chloro-4-[(1-methylethyl)oxy]phenyl}-1,2,4-oxadiazol-3-yl)-2,3-dihydro-1,4-benzoxazepin-4(5H)-yl]acetate

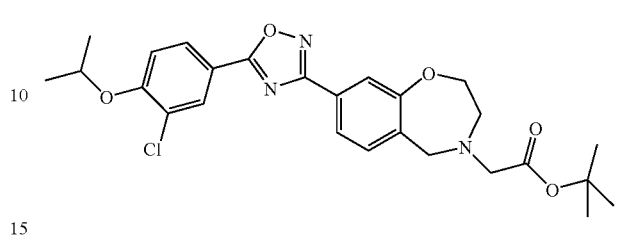

A mixture of 8-(5-{3-chloro-4-[(1-methylethyl)oxy]phenyl}-1,2,4-oxadiazol-3-yl)-2,3,4,5-tetrahydro-1,4-benzoxazepine (Example 13) (0.127 g, 0.301 mmol), 1,1-dimethylethyl bromoacetate (0.117 g, 0.601 mmol) and DIPEA (0.210 ml, 1.203 mmol) in acetonitrile (5 ml) was stirred and heated at 70° C. for one hour. The cooled reaction mixture was diluted with EtOAc/water (30 ml of each) and the organics dried (magnesium sulphate), evaporated and purified by flash chromatography eluting with 1:2 EtOAc/iso-hexane to give the title compound (130 mgs) as a colourless gum. MS (ES) $C_{28}H_{38}{}^{35}ClN_3O_5$ requires 499; found 500 $[M+H]^+$.

Preparation 38

1-Methylethyl 4-[(1-methylethyl)oxy]-3-(trifluoromethyl)benzoate

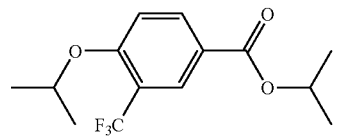

A mixture of 4-hydroxy-3-(trifluoromethyl)benzoic acid (2.5 g, 12.1 mmol), 2-iodopropane (2.42 ml, 24.3 mmol) and potassium carbonate (3.35 g, 24.3 mmol) in N,N'-dimethylformamide (200 ml) was heated at 70° C. for 4 hrs. The reaction mixture was partially concentrated in vacuo and the residue partitioned between EtOAc (150 ml) and water (150 ml) containing some aqueous sodium hydroxide. The aqueous phase was extracted with further EtOAc (2×100 ml) and the combined organic fractions dried (hydrophobic frit phase separator) and concentrated in vacuo to give the crude title compound as a yellow oil (3.6 g, 12.1 mmol). δH (d$_6$DMSO, 400 MHz): 8.16 (1H, dd), 8.08 (1H, d), 7.43 (1H, d), 5.13 (1H, septet), 4.91 (1H, septet), 1.32 (12H, d).

Preparation 39

4-[(1-Methylethyl)oxy]-3-(trifluoromethyl)benzoic acid

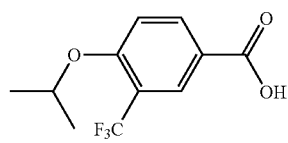

To a mixture of 1-methylethyl 4-[(1-methylethyl)oxy]-3-(trifluoromethyl)benzoate (Preparation 38) (3.63 g, 12.5 mmol) in ethanol (100 ml) was added aqueous sodium hydroxide (12.5 M, 10.0 ml, 125 mmol) and the reaction heated to reflux for 3 hrs. The mixture was concentrated in vacuo and the residue partitioned between EtOAc (100 ml) and water (100 ml) and acidified with aqueous hydrochloric acid. The aqueous layer was extracted further with EtOAc (100 ml) and the combined organic layers dried and concentrated in vacuo to give the title compound as a yellow solid (2.68 g, 10.8 mmol). MS (ES−): $C_{11}H_{11}F_3O_3$ requires 248; found 247 [M−H⁺].

Preparation 40

2-(Trifluoromethyl)-4-biphenylcarboxylic acid

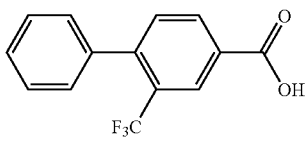

The reaction was split into 4, using a quarter of the reagents shown in each: to a mixture of 4-bromo-3-(trifluoromethyl) benzonitrile (4 g, 16.00 mmol), phenylboronic acid (3.90 g, 32.0 mmol) and potassium carbonate (6.63 g, 48.0 mmol) in DMF (64 ml) was added palladium tetrakistriphenylphosphine(0) (1.849 g, 1.600 mmol). Each reaction was heated in the microwave at 150° C. for 30 minutes. The combined reaction mixtures were filtered through Celite®, washed with EtOAc and the solvent removed in vacuo. The residue was partitioned between EtOAc (100 ml) and water (100 ml) and the organic phase washed with sodium bicarbonate solution (100 ml). The organic phase was dried (MgSO₄), filtered and the solvent removed in vacuo. The brown oil was triturated with DCM and filtered to give a pale yellow solid, 2-(trifluoromethyl)-4-biphenylcarboxamide (2.47 g) which was used without further purification. To 2-(trifluoromethyl)-4-biphenylcarboxamide (2 g, 7.54 mmol) in ethanol (80 ml) was added potassium hydroxide (4.23 g, 75 mmol) and water and the mixture heated to 90° C. for 18 hrs. The reaction mixture was concentrated in vacuo and the residue partitioned between DCM (100 ml) and 2M HCl (100 ml). The organic phase was isolated and dried (hydrophobic frit phase separator) and the solvent removed in vacuo to give the crude product. Chromatographic purification using the Biotage Horizon, reverse phase cartridge, eluting 5-100% MeCN in water to give the title compound as an off-white solid (960 mg). LCMS (ES−): $C_{14}H_9F_3O_2$ requires 266; found 265 [M−H⁺]

Preparation 41

1,1-Dimethylethyl 7-[(hydroxyamino)(imino)methyl]-1,2,4,5-tetrahydro-3H-3-benzazepine-3-carboxylate

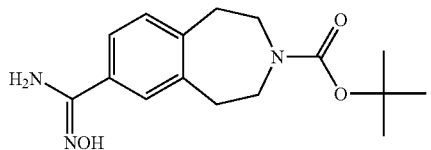

A suspension of 1,1-dimethylethyl 7-cyano-1,2,4,5-tetrahydro-3H-3-benzazepine-3-carboxylate (may be prepared as described in WO2002040471) (5 g, 18.36 mmol), hydroxylamine hydrochloride (2.55 g, 36.7 mmol) and sodium bicarbonate (7.71 g, 92 mmol) in ethanol (250 ml) was heated at 50° C. overnight. Further hydroxylamine hydrochloride (0.638 g, 9.18 mmol) was added to the reaction mixture and heating at 50° C. continued for 5 h. The reaction mixture was allowed to cool and the solid filtered off, the solution was concentrated in vacuo to yield the title compound as a white solid (5.77 g, 17.01 mmol, 93% yield). δH (d₆DMSO, 400 MHz): 9.56 (1H, s), 7.52-7.37 (2H, m), 7.14 (1H, d), 5.77 (2H, br s), 3.50-3.32 (4H, m), 2.91-2.80 (4H, m), 1.41 (9H, s). MS (ES): $C_{16}H_{23}N_3O_3$ requires 305; found 306 [M+H]⁺.

Preparation 42

1,1-Dimethylethyl 7-(5-{3-chloro-4-[(1-methylethyl) oxy]phenyl}-1,2,4-oxadiazol-3-yl)-1,2,4,5-tetrahydro-3H-3-benzazepine-3-carboxylate

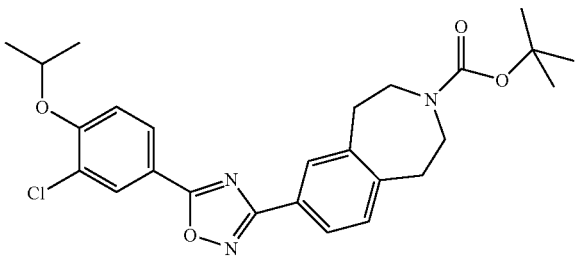

To a solution of 3-chloro-4-[(1-methylethyl)oxy]benzoic acid (Preparation 6) (1.406 g, 6.55 mmol) in DMF was added HOBT (1.103 g, 7.20 mmol) and EDC (1.381 g, 7.20 mmol), the resultant solution was stirred under argon for 10 mins at room temp. 1,1-dimethylethyl 7-[(hydroxyamino)(imino) methyl]-1,2,4,5-tetrahydro-3H-3-benzazepine-3-carboxylate (Preparation 41)(2 g, 6.55 mmol) was then added to the reaction mixture and the solution heated at 80° C. overnight. The solvent was removed in vacuo and the residue dissolved in methanol for purification by Biotage Horizon, reverse phase cartridge, eluting 5-100% acetonitrile in water. The product containing fractions (last 5) were concentrated in vacuo to yield the title compound as a yellow oil (950 mg, 1.87 mmol, 29% yield). δH (d₆DMSO, 400 MHz): 8.19 (1H, d), 8.11 (1H, dd), 7.83-7.89 (2H, m), 7.45 (1H, d), 7.37 (1H, d), 4.89 (1H, sept), 3.50 (4H, br.s), 2.96 (4H, br.s), 1.41 (9H, s), 1.36 (6H, d). MS (ES): $C_{26}H_{30}{}^{35}ClN_3O_4$ requires 483; found 384 [M+H−100]⁺.

Preparation 43

1,1-Dimethylethyl-7-(5-{3-cyano-4-[(1-methylethyl) oxy]phenyl}-1,2,4-oxadiazol-3-yl)-1,2,4,5-tetrahydro-3H-3-benzazepine-3-carboxylate

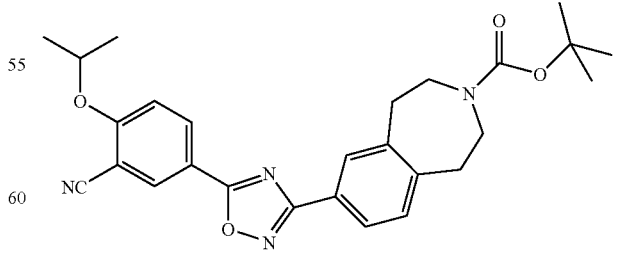

3-Cyano-4-[(1-methylethyl)oxy]benzoic acid (can be prepared as described in WO2005/58848) (687 mg, 3.63 mmol), HOBT (539 mg, 3.99 mmol) and EDC (762 mg, 3.99 mmol) were stirred in DMF (30 ml) under argon for 20 minutes.

1,1-dimethylethyl 7-[(hydroxyamino)(imino)methyl]-1,2,4,5-tetrahydro-3H-3-benzazepine-3-carboxylate (Preparation 41) (1.11 g, 3.63 mmol) was added and the mixture stirred at room temperature for 4 h before it was heated to 80° C. for 20 h. The reaction mixture was partitioned between EtOAc (80 ml) and water (80 ml) and the organic layer washed with aqueous sodium bicarbonate and water before it was dried in the usual manner and evaporated. The residue was triturated with methanol to give the title compound as a white solid (981 mg, 2.07 mmol). δH (d$_6$DMSO, 400 MHz): 8.50 (1H, d), 8.40 (1H, dd), 7.88 (1H, br.s), 7.85 (1H, dd), 7.56 (1H, d), 7.38 (1H, d), 4.98 (1H, septet), 3.53-3.47 (4H, m), 3.00-2.92 (4H, m), 1.41 (9H, s), 1.39 (6H, d).

Preparation 44

1,1-Dimethylethyl 7-{5-[4-[(1-methylethyl)oxy]-3-(trifluoro-methyl)phenyl]-1,2,4-oxadiazol-3-yl}-1,2,4,5-tetrahydro-3H-3-benzazepine-3-carboxylate

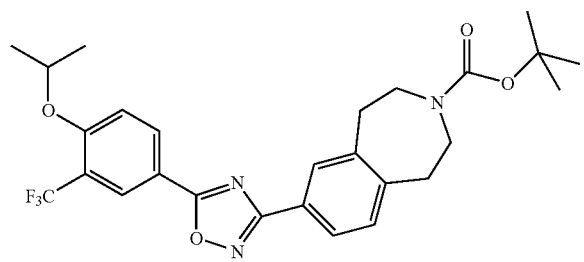

4-[(1-Methylethyl)oxy]-3-(trifluoromethyl)benzoic acid (Preparation 39) (744 mg, 3.00 mmol), HOBT (446 mg, 3.30 mmol) and EDC (630 mg, 3.30 mmol) were stirred in DMF (28 ml) under argon for 20 minutes. 1,1-dimethylethyl 7-[(hydroxyamino)(imino)methyl]-1,2,4,5-tetrahydro-3H-3-benzazepine-3-carboxylate (Preparation 41) (915 mg, 3.00 mmol) was added and the mixture stirred at room temperature for 2 hrs before it was heated to 80° C. for 20 hrs. The reaction mixture was partitioned between EtOAc and water and the organic layer washed with aqueous sodium bicarbonate before it was dried in the usual manner and evaporated. The residue was purified by Biotage Horizon, reverse phase cartridge, eluting with 5-100% acetonitrile in water to give the title compound (749 mg, 1.45 mmol). δH (d$_6$DMSO, 400 MHz): 8.40 (1H, dd), 8.31 (1H, d), 7.89 (1H, br.s), 7.86 (1H, dd), 7.58 (1H, d), 7.37 (1H, d), 4.98 (1H, septet), 3.54-3.46 (4H, m), 3.00-2.92 (4H, m), 1.41 (9H, s), 1.36 (6H, d).

Preparation 45

1,1-Dimethylethyl 7-{5-[2-(trifluoromethyl)-4-biphenylyl]-1,2,4-oxadiazol-3-yl}-1,2,4,5-tetrahydro-3H-3-benzazepine-3-carboxylate

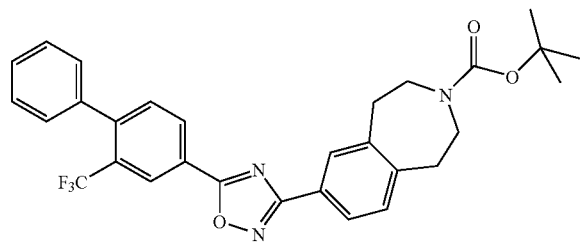

2-(Trifluoromethyl)-4-biphenylcarboxylic acid (Preparation 40) (284 mg, 1.07 mmol), HOBT (159 mg, 1.18 mmol) and EDC (225 mg, 1.18 mmol) were stirred in DMF (10 ml) under argon for 20 minutes. 1,1-Dimethylethyl 7-[(hydroxyamino)(imino)methyl]-1,2,4,5-tetrahydro-3H-3-benzazepine-3-carboxylate (Preparation 41) (326 mg, 1.07 mmol) was added and the mixture stirred at room temperature for 2.5 h before it was heated to 80° C. for 16 h. The reaction mixture was partitioned between EtOAc (30 ml) and water (30 ml) and the organic layer washed with aqueous sodium bicarbonate and water before it was dried (phase separator) and evaporated. The residue was triturated with methanol to give the title compound as a white solid (370 mg, 0.69 mmol). The filtrate was purified by Biotage Horizon, reverse phase cartridge, eluting with 5-100% acetonitrile in water to give further title compound (70 mg, 0.13 mmol). δH (d$_6$DMSO, 400 MHz): 8.52 (1H, s), 8.50 (1H, d), 7.93 (1H, s), 7.90 (1H, dd), 7.74 (1H, d) 7.56-7.48 (3H, m), 7.41-7.38 (3H, m), 3.55-3.47 (4H, m), 3.02-2.93 (4H, m), 1.41 (9H, s).

Preparation 46

Ethyl [7-(5-{3-chloro-4-[(1-methylethyl)oxy]phenyl}-1,2,4-oxadiazol-3-yl)-1,2,4,5-tetrahydro-3H-3-benzazepin-3-yl]acetate

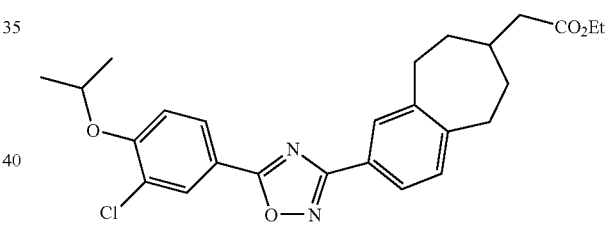

7-(5-{3-Chloro-4-[(1-methylethyl)oxy]phenyl}-1,2,4-oxadiazol-3-yl)-2,3,4,5-tetrahydro-1H-3-benzazepine hydrochloride (Example 17) (100 mg, 0.238 mmol), ethyl bromoacetate (0.043 ml, 0.391 mmol) and cesium carbonate (170 mg, 0.521 mmol) were stirred at room temperature in DMF for 5 hours. The reaction mixture was diluted with diethyl ether (~20 ml) and washed with water (2×~20 ml), the organic layer was passed through a phase separating cartridge to dry and concentrated in vacuo to yield the title compound (77 mg, 0.16 mmol, 60% yield) as a yellow oil. δH (d$_6$DMSO, 400 MHz): 8.19 (1H, s), 8.11 (1H, dd), 7.81-7.85 (2H, m), 7.45 (1H, d), 7.34 (1H, d), 4.89 (1H, sept), 4.07 (2H, q) 3.42 (2H, s), 3.00-291 (4H, m), 2.77-2.72 (4H, m), 1.36 (6H, d), 1.19 (3H, t). MS (ES): $C_{25}H_{28}{}^{35}ClN_3O_4$ requires 469; found 470 [M+H]$^+$.

The following compounds were made by similar methods. Preparation 49 was further purified by MDAP.

| Preparation | Structure | Name | m/z |
|---|---|---|---|
| 47 | 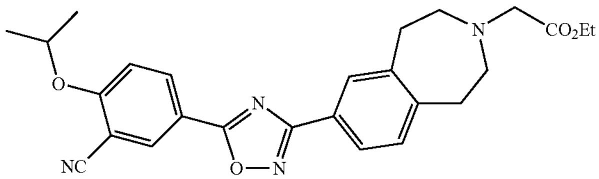 | ethyl [7-(5-{3-cyano-4-[(1-methylethyl)oxy]phenyl}-1,2,4-oxadiazol-3-yl)-1,2,4,5-tetrahydro-3H-3-benzazepin-3-yl]acetate | 461 [M + H]⁺ |
| 48 | 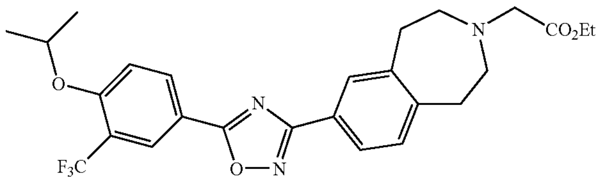 | ethyl (7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)acetate | 504 [M + H]⁺ |
| 49 | 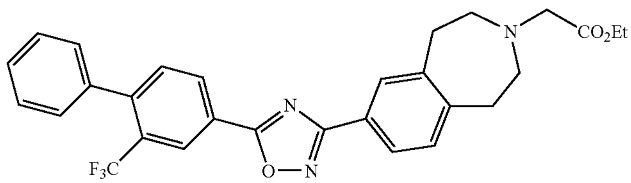 | ethyl (7-{5-[2-(trifluoromethyl)-4-biphenylyl]-1,2,4-oxadiazol-3-yl}-1,2,4,5-tetrahydro-3H-3-benzazepin-3-yl)acetate | 522 [M + H]⁺ |

Preparation 50

Ethyl 4-[7-(5-{3-chloro-4-[(1-methylethyl)oxy]phenyl}-1,2,4-oxadiazol-3-yl)-1,2,4,5-tetrahydro-3H-3-benzazepin-3-yl]butanoate

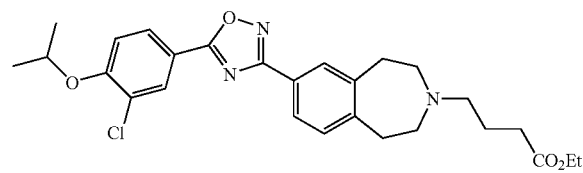

7-(5-{3-Chloro-4-[(1-methylethyl)oxy]phenyl}-1,2,4-oxadiazol-3-yl)-2,3,4,5-tetrahydro-1H-3-benzazepine hydrochloride (Example 17) (65 mg, 0.155 mmol), DIPEA (0.104 ml, 0.593 mmol) and ethyl 4-bromobutanoate (0.048 ml, 0.339 mmol) were stirred at 60° C. in DMF (10 ml) for 24 hours. The reaction mixture was partitioned between EtOAc (~30 ml) and water (~30 ml) and the aqueous layer extracted once more with EtOAc (~40 ml). The combined organics were concentrated in vacuo to yield the crude title compound (100 mg, 0.171 mmol) as an orange solid. MS (ES): $C_{27}H_{32}{}^{35}ClN_3O_4$ requires 497; found 498 [M+H]⁺.

Preparation 51

Ethyl 4-[7-(5-{3-cyano-4-[(1-methylethyl)oxy]phenyl}-1,2,4-oxadiazol-3-yl)-1,2,4,5-tetrahydro-3H-3-benzazepin-3-yl]butanoate

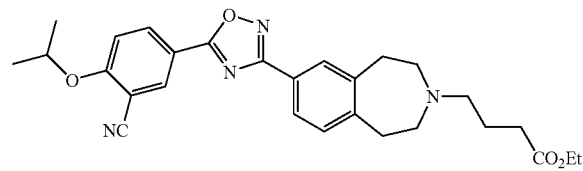

2-[(1-Methylethyl)oxy]-5-[3-(2,3,4,5-tetrahydro-1H-3-benzazepin-7-yl)-1,2,4-oxadiazol-5-yl]benzonitrile hydrochloride (Example 18) (200 mg, 0.534 mmol), DIPEA (0.327 ml, 1.869 mmol) and ethyl 4-bromobutanoate (0.153 ml, 1.068 mmol) were stirred at room temperature in DMF (10 ml) for 5 hours, the reaction mixture then heated to 60° C. for 5 h, the reaction mixture was allowed to stand overnight at room temperature, further ethyl 4-bromobutanoate (0.076 ml, 0.534 mmol) was added and the reaction mixture heated at 60° C. for 6 hours. The reaction mixture was partitioned between ethylacetate (~30 ml) and water (~30 ml) and the aq. layer extracted once more with ethylacetate (~40 ml). The combined organics were concentrated in vacuo to yield the title compound (218 mg, 0.402 mmol) as an orange oil. MS (ES): $C_{28}H_{32}N_4O_4$ requires 488; found 489 [M+H]⁺.

Preparation 52

Ethyl 4-(7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)butanoate

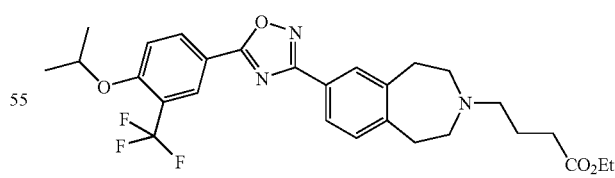

7-{5-[4-[(1-Methylethyl)oxy]-3-(trifluoromethyl)phenyl]-1,2,4-oxadiazol-3-yl}-2,3,4,5-tetrahydro-1H-3-benzazepine hydrochloride (Example 19) (160 mg, 0.353 mmol), DIPEA (0.234 ml, 1.342 mmol) and ethyl 4-bromobutanoate (0.110 ml, 0.767 mmol) were stirred at room temperature in DMF (10 ml) for 5 hours. The reaction mixture was then heated to 60° C. for 5 h, and allowed to stand overnight at room temperature. Further ethyl 4-bromobutanoate (0.055 ml, 0.383 mmol) was added and the reaction mixture heated at 60° C. for 6 hours. The reaction mixture was partitioned between EtOAc (~30 ml) and water (~30 ml) and the aqueous layer extracted once more with EtOAc (~40 ml). The combined organics were concentrated in vacuo to yield the title compound (183 mg, 0.310 mmol) as an orange solid. MS (ES): $C_{28}H_{32}F_3N_3O_4$ requires 531; found 532 $[M+H]^+$.

Preparation 53

Ethyl 4-(7-{5-[2-(trifluoromethyl)-4-biphenylyl]-1,2,4-oxadiazol-3-yl}-1,2,4,5-tetrahydro-3H-3-benzazepin-3-yl)butanoate

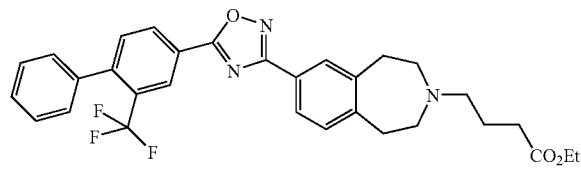

7-{5-[2-(Trifluoromethyl)-4-biphenylyl]-1,2,4-oxadiazol-3-yl}-2,3,4,5-tetrahydro-1H-3-benzazepine hydrochloride (Example 20) (200 mg, 0.424 mmol), DIPEA (0.281 ml, 1.608 mmol) and ethyl 4-bromobutanoate (0.131 ml, 0.919 mmol) were stirred at RT in DMF (10 ml) for 5 hours. The reaction mixture was then heated to 60° C. for 5 hrs, and then allowed to stand overnight at room temperature. Further ethyl 4-bromobutanoate (0.066 ml, 0.459 mmol) was added and the reaction mixture heated at 60° C. for 6 hours. The reaction mixture was partitioned between EtOAc (~30 ml) and water (~30 ml) and the aqueous layer extracted once more with EtOAc (~40 ml). The combined organics were concentrated in vacuo to yield the title compound (277 mg, 0.454 mmol) as an orange solid. MS (ES): $C_{31}H_{30}F_3N_3O_3$ requires 549; found 550 $[M+H]^+$.

Preparation 54

1,1-Dimethylethyl 7-{5-[3-cyano-4-(methyloxy)phenyl]-1,2,4-oxadiazol-3-yl}-1,2,4,5-tetrahydro-3H-3-benzazepine-3-carboxylate

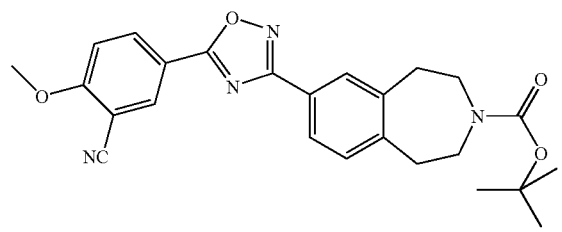

1,1-Dimethylethyl 7-[(hydroxyamino)(imino)methyl]-1,2,4,5-tetrahydro-3H-3-benzazepine-3-carboxylate (Preparation 41) (240 mg, 0.785 mmol) was added to a suspension of sodium hydride (60% dispersion in mineral oil) (23.01 mg, 0.575 mmol) in THF (5 ml) at room temperature (note slight effervescence). The resultant mixture was stirred at room temperature for 30 mins, methyl 3-cyano-4-(methyloxy)benzoate (100 mg, 0.523 mmol) was then added and the reaction mixture was heated to reflux (75° C.) for 45 mins. The reaction mixture was diluted with water and ethylacetate and the layers partitioned, solid was present in the bi-phasic mixture so this was transferred to a conical flask and stirred at room temperature for 2 h at room temperature. The mixture was then partitioned and the organic layer concentrated in vacuo. to yield the title compound (280 mg, 0.502 mmol, 96% yield) as a yellow oil. MS (ES): $C_{25}H_{26}N_4O_4$ requires 447; no mass ion present. $^1$H NMR (400 MHz, CDCl$_3$) δ 1H, d (8.44), 1H, dd (8.38), 2H, m (7.89-7.95), 1H, m (7.35-7.42), 1H, m (7.13-7.17), 3H, s (4.06), 4H, m (3.50-3.66), 4H, m (2.87-3.06), 9H, s (1.50).

Preparation 55

Methyl 2-{[2-({[(1,1-dimethylethyl)oxy]carbonyl}amino)ethyl]oxy}-3-(methyloxy)benzoate

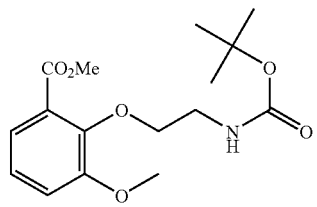

DIAD (23.95 ml, 123 mmol) was added dropwise to a stirred solution of 1,1-dimethylethyl (2-hydroxyethyl)carbamate (18.05 g, 112 mmol), methyl 2-hydroxy-3-(methyloxy)benzoate (20.4 g, 112 mmol) and triphenylphosphine (32.3 g, 123 mmol) in THF (400 ml) with cooling in an ice/water bath. Stirred for 30 mins then evaporated and used without any purification. LC/MS showed essentially just product and triphenylphosphine oxide. Yield 98.9 g of crude material. MS (ES): $C_{16}H_{23}NO_6$ requires 325; found 326 $[M+H]^+$.

Preparation 56

Methyl 2-[(2-aminoethyl)oxy]-3-(methyloxy)benzoate

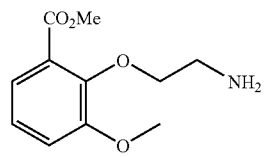

Methyl 2-{[2-({[(1,1-dimethylethyl)oxy]carbonyl}amino)ethyl]oxy}-3-(methyloxy)benzoate (Preparation 55) (98.9 g, 304 mmol) (crude material, in reality only contained a maximum of 0.112 mols or 36.4 g) was dissolved in a mixture of TFA (60 ml, 779 mmol) and DCM (60 ml) and left at room temperature for 1.5 hrs. Evaporated and dissolved in EtOAc/2M HCl (250 ml of each) and the organic extracted with a further 2×100 ml of EtOAc. 250 ml of EtOAc added to aqueous and 500 g of ice added and solution basified with 50% sodium hydroxide. Organic separated and aqueous extracted with a further 5×75 ml of EtOAc. Combined organics dried (magnesium sulphate) and evaporated to give 11.9 g of colourless oil. LC/MS showed 13% product and 87% of material already cyclised to the benzoxazepine. MS (ES): $C_{11}H_{15}NO_4$ requires 225; found 226 $[M+H]^+$.

Preparation 57

9-(Methyloxy)-3,4-dihydro-1,4-benzoxazepin-5(2H)-one

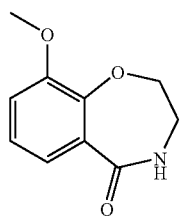

A solution of methyl 2-[(2-aminoethyl)oxy]-3-(methyloxy)benzoate (Preparation 56) (11.9 g, 52.8 mmol) in toluene (200 ml) was stirred and heated at 110° C. for 1 hour then cooled and evaporated to give the title compound (10.3 g) as a sandy coloured solid. MS (ES): $C_{10}H_{11}NO_3$ requires 193; found 194 [M+H]$^+$.

Preparation 58

9-Hydroxy-3,4-dihydro-1,4-benzoxazepin-5(2H)-one

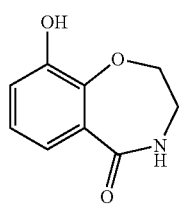

9-(Methyloxy)-3,4-dihydro-1,4-benzoxazepin-5(2H)-one (Preparation 57) (9.3 g, 48.1 mmol) in hydrobromic acid (120 ml, 2210 mmol) was stirred and heated at 105° C. for 5 hours. Evaporated to dryness, azeotroped with 200 ml of ethanol and biotage chromatographed twice in 3% methanol in EtOAc. Triturated with EtOAc and filtered off to give 6.61 g of white solid. MS (ES): $C_9H_9NO_3$ requires 179; found 180 [M+H]$^+$.

Preparation 59

9-[(Phenylmethyl)oxy]-3,4-dihydro-1,4-benzoxazepin-5(2H)-one

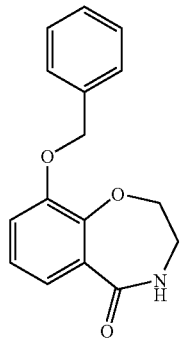

A mixture of 9-hydroxy-3,4-dihydro-1,4-benzoxazepin-5(2H)-one (7.46 g, 41.6 mmol), benzyl bromide (Preparation 58) (5.45 ml, 45.8 mmol) and potassium carbonate (17.26 g, 125 mmol) was stirred and heated at 60° C. in DMF (75 ml) for 2 hours. Cooled, diluted with water (300 ml) and extracted with EtOAc (200 ml and 4×75 ml) and the combined organics washed with 3×100 ml of water. Dried (magnesium sulphate), evaporated, triturated with ether and filtered off to give 7.55 g of white solid. MS (ES): $C_{16}H_{15}NO_3$ requires 269; found 270 [M+H]$^+$.

Preparation 60

9-[(Phenylmethyl)oxy]-2,3,4,5-tetrahydro-1,4-benzoxazepine

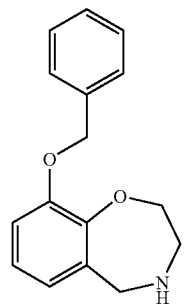

1M Lithium aluminum hydride (60 ml, 60.0 mmol) in THF was added to a stirred solution of 9-[(phenylmethyl)oxy]-3,4-dihydro-1,4-benzoxazepin-5(2H)-one (Preparation 59) (7.4 g, 27.5 mmol) in THF (150 ml) under argon and heated at 60° C. for 2 hours then cooled and quenched by careful addition of 100 ml of 2M sodium hydroxide with ice bath cooling and the resulting suspension filtered, the solids washed with water and EtOAc and the organic dried (magnesium sulphate) and evaporated to give 7.01 g of white solid. MS (ES): $C_{16}H_{17}NO_2$ requires 255; found 256 [M+H]$^+$.

Preparation 61

1,1-Dimethylethyl 9-[(phenylmethyl)oxy]-2,3-dihydro-1,4-benzoxazepine-4(5H)-carboxylate

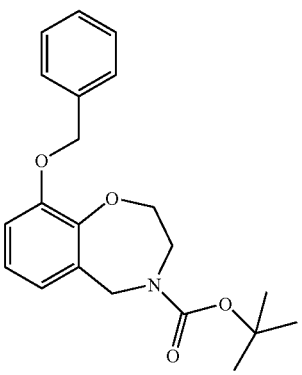

9-[(Phenylmethyl)oxy]-2,3,4,5-tetrahydro-1,4-benzoxazepine (Preparation 60) (7.01 g, 27.5 mmol) and BOC$_2$O (7.01 ml, 30.2 mmol) were dissolved in DCM (100 ml) and left at room temperature for one hour then evaporated and biotage chromatographed in 5% EtOAc in hexane to remove excess BOC$_2$O and changing to 15% EtOAc in iso-hexane to elute the title compound (8.25 g) as a white solid. MS (ES): $C_{21}H_{25}NO_4$ requires 355; found 256 $[M+H-100]^+$.

Preparation 62

1,1-Dimethylethyl 9-hydroxy-2,3-dihydro-1,4-benzoxazepine-4(5H)-carboxylate

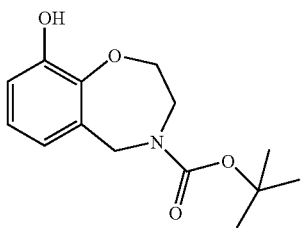

A solution of 1,1-dimethylethyl 9-[(phenylmethyl)oxy]-2,3-dihydro-1,4-benzoxazepine-4(5H)-carboxylate (Preparation 61) (8.25 g, 23.21 mmol) in ethanol (100 ml) was hydrogenated with 10% palladium on carbon (0.825 g, 7.75 mmol) for 18 hours, filtered and evaporated to give 6.16 g of white solid. MS (ES-): $C_{21}H_{25}NO_4$ requires 265; found 264 $[M-H^+]$.

Preparation 62 (Alternative Preparation)

1,1-Dimethylethyl 9-hydroxy-2,3-dihydro-1,4-benzoxazepine-4(5H)-carboxylate

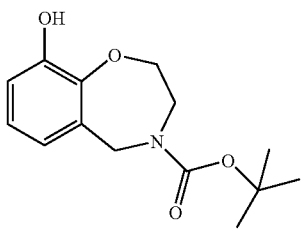

A suspension of 2,3,4,5-tetrahydro-1,4-benzoxazepin-9-ol. hydrobromide (Preparation 85) (55.7 g, 226 mmol) in dichloromethane (DCM) (550 ml) was treated with triethylamine (47.3 ml, 339 mmol) and stirred for 20 minutes. This mixture was cooled in ice/water to ca 5° C. and treated slowly with a solution of $BOC_2O$ (59.6 ml, 249 mmol) in dichloromethane (DCM) (200 ml) at such a rate as to keep the internal temperature below 10° C. When the addition was complete, the mixture was allowed to warm to room temperature, stirred for 2 hours and allowed to stand at room temperature overnight. The mixture was washed with 0.5M hydrochloric acid (2×250 ml) and water (250 ml), dried (sodium sulphate) and evaporated to give the title compound as a pale brown solid (60.5 g)

MS (ES-): $C_{21}H_{25}NO_4$ requires 265; found 264 $[M-H]^+$.

Preparation 63

1,1-Dimethylethyl 9-{[(trifluoromethyl)sulfonyl]oxy}-2,3-dihydro-1,4-benzoxazepine-4(5H)-carboxylate

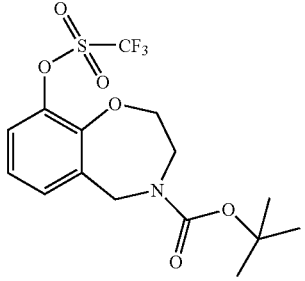

Trifluoromethanesulfonic anhydride (6.04 ml, 35.7 mmol) was added to an ice cooled solution of 1,1-dimethylethyl 9-hydroxy-2,3-dihydro-1,4-benzoxazepine-4(5H)-carboxylate (Preparation 62) (6.32 g, 23.82 mmol) in pyridine (100 ml) and stirred at 0° C. for 2 hrs. The pyridine was evaporated and the residue dissolved in EtOAc. Washed with 2M HCl, sat sodium bicarbonate solution, dried over magnesium sulphate and evaporated to give the title compound (9 g) as a yellow oil. MS (ES): $C_{15}H_{18}F_3NO_6S$ requires 397; found 298 $[M+H-100]^+$.

Preparation 64

1,1-Dimethylethyl 9-cyano-2,3-dihydro-1,4-benzoxazepine-4(5H)-carboxylate

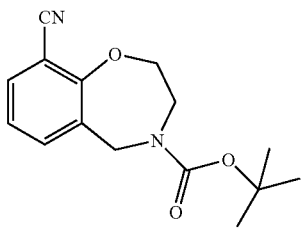

A solution of 1,1-dimethylethyl 9-{[(trifluoromethyl)sulfonyl]oxy}-2,3-dihydro-1,4-benzoxazepine-4(5H)-carboxylate (Preparation 63) (9 g, 22.65 mmol), zinc cyanide (3.99 g, 34.0 mmol) and tetrakis(triphenylphosphine)palladium(0) (2.62 g, 2.265 mmol) in DMF (90 ml) was heated at 80° C. for 24 hrs. The reaction was cooled, diluted with EtOAc (400 ml) and water (400 ml) and filtered to remove insoluble material. The filtrate was separated and the organic layer washed with water, dried over magnesium sulphate and evaporated. Purified by flash chromatography eluting with EtOAc/iso-hexane 1:9 then 1:3 to give the title compound (5.1 g) as a colourless oil. MS (ES): $C_{15}H_{18}N_2O_3$ requires 274; found 174 $[M+H-100]^+$.

Preparation 64 (Alternative Preparation)

1,1-Dimethylethyl 9-cyano-2,3-dihydro-1,4-benzoxazepine-4(5H)-carboxylate

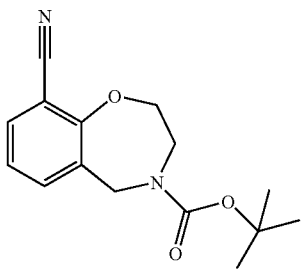

A solution of 1,1-dimethylethyl 9-bromo-2,3-dihydro-1,4-benzoxazepine-4(5H)-carboxylate (Preparation 101) (1.34 g, 4.08 mmol) in N,N-dimethylformamide (11 ml) was degassed under vacuum (3 mm Hg) for 15 min then stirred under nitrogen. Zinc cyanide (575 mg, 4.90 mmol) then tetrakis(triphenylphosphine) palladium(0) (472 mg, 0.41 mmol) were added and the resulting mixture was stirred at 100° C. under nitrogen overnight then diluted with ethyl acetate. The insoluble residues were filtered off and washed with ethyl acetate, bleached for two days washed twice with brine, dried over magnesium sulphate and concentrated in vacuo. Purification of the residue by flash chromatography on silica gel, eluting with 15-45% ethyl acetate in cyclohexane gave the title compound as a colourless solid (980 mg). MS (ES) $C_{15}H_{18}N_2O_3$ requires 274 found 275 [M+H]$^+$.

Preparation 65

1,1-Dimethylethyl 9-[(hydroxyamino)(imino)methyl]-2,3-dihydro-1,4-benzoxazepine-4(5H)-carboxylate

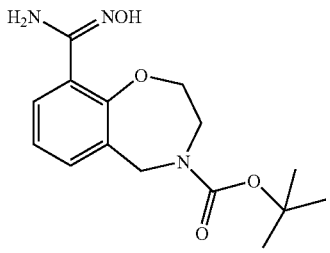

A suspension of 1,1-dimethylethyl 9-cyano-2,3-dihydro-1,4-benzoxazepine-4(5H)-carboxylate (Preparation 64) (5.1 g, 18.59 mmol), hydroxylamine hydrochloride (2.58 g, 37.2 mmol) and sodium bicarbonate (7.81 g, 93 mmol) in ethanol (50 ml) was heated at 60° C. overnight. A further portion of hydroxylamine hydrochloride (1 g) was added and the reaction was heated at 60° C. overnight. The solid was filtered from the reaction mixture and the filtrate evaporated. The residue from the evaporation was dissolved in EtOAc, washed with water, dried over magnesium sulphate and evaporated. Trituration with ether to gave the title compound (3.94 g) as a white solid. MS (ES): $C_{15}H_{21}N_3O_4$ requires 307; found 308 [M+H]$^+$.

Preparation 66

1,1-Dimethylethyl 9-(5-{3-chloro-4-[(1-methylethyl)oxy]phenyl}-1,2,4-oxadiazol-3-yl)-2,3-dihydro-1,4-benzoxazepine-4(5H)-carboxylate

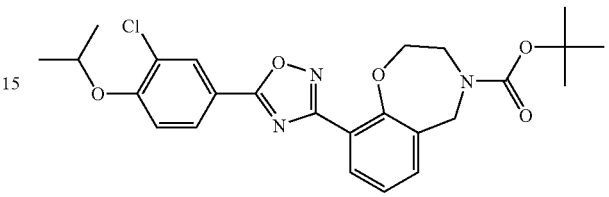

A solution of 1,1-dimethylethyl 9-[(hydroxyamino)(imino)methyl]-2,3-dihydro-1,4-benzoxazepine-4(5H)-carboxylate (Preparation 65) (500 mg, 1.627 mmol), 3-chloro-4-[(1-methylethyl)oxy]benzoic acid (384 mg, 1.790 mmol), EDC (468 mg, 2.440 mmol) and HOBT (299 mg, 1.952 mmol) in DMF (5 ml) was stirred at RT overnight then heated at 120° C. for 3 hrs. The reaction mixture was cooled, diluted with EtOAc/water and the organics dried over magnesium sulfate and evaporated. Purified by flash chromatography eluting with EtOAc/iso-hexane 1:3 to give the title compound (320 mg) as a white solid. MS (ES): $C_{25}H_{28}{}^{35}ClN_3O_5$ requires 485; found 486 [M+H]$^+$.

Preparation 66 Alternative Preparation 1,1-Dimethylethyl 9-(5-{3-chloro-4-[(1-methylethyl)oxy]phenyl}-1,2,4-oxadiazol-3-yl)-2,3-dihydro-1,4-benzoxazepine-4(5H)-carboxylate

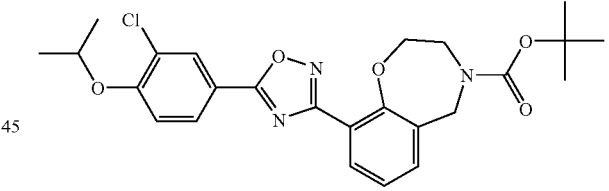

A mixture of 1,1-dimethylethyl 9-[(hydroxyamino)(imino)methyl]-2,3-dihydro-1,4-benzoxazepine-4(5H)-carboxylate (Preparation 65) (32.9 g, 107 mmol) and triethylamine (17.9 ml, 128 mmol) in dry N,N-dimethylformamide (DMF) (200 ml) was cooled in ice/water under nitrogen. A solution of 3-chloro-4-[(1-methylethyl)oxy]benzoyl chloride (Preparation 102) (28.7 g, 123 mmol) in DMF (100 ml) was added over ca 20 minutes. When the addition was complete the mixture was allowed to warm to room temperature and stirred for 1 hour at room temperature, then at 120° C. for 3 hours. The mixture was allowed to cool and was poured into water (1 liter). The resulting solid was extracted into ethyl acetate (3×300 ml) and the extracts combined, washed with 1M hydrochloric acid (2×250 ml), then 1M sodium carbonate solution (3×250 ml), brine (250 ml), dried (sodium sulphate) and evaporated. The residue was purified by chromatography on silica. Eluting with a 10-40% gradient of ethyl acetate in isohexane to give the title compound as a crystalline solid (42.7 g) MS (ES): $C_{25}H_{28}{}^{35}ClN_3O_5$ requires 485; found 486 [M+H]$^+$.

Preparation 67

1,1-Dimethylethyl 9-(5-{3-cyano-4-[(1-methylethyl)oxy]phenyl}-1,2,4-oxadiazol-3-yl)-2,3-dihydro-1,4-benzoxazepine-4(5H)-carboxylate

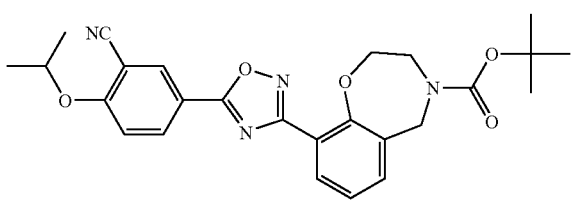

Prepared in a similar way to Preparation 66 from Preparation 65. MS (ES): $C_{26}H_{28}N_4O_5$ requires 476; found 477 $[M+H]^+$.

Preparation 68

Ethyl 4-[9-(5-{3-chloro-4-[(1-methylethyl)oxy]phenyl}-1,2,4-oxadiazol-3-yl)-2,3-dihydro-1,4-benzoxazepin-4(5H)-yl]butanoate

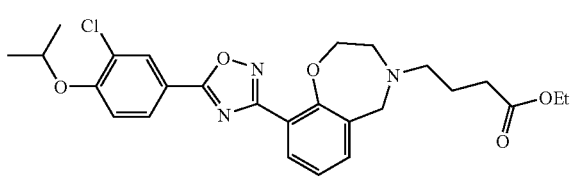

A solution of 9-(5-{3-chloro-4-[(1-methylethyl)oxy]phenyl}-1,2,4-oxadiazol-3-yl)-2,3,4,5-tetrahydro-1,4-benzoxazepine hydrochloride (Example 31) (179 mg, 0.424 mmol), ethyl 4-bromobutanoate (0.061 ml, 0.424 mmol) and DIPEA (0.074 ml, 0.424 mmol) in Acetonitrile (5 ml) was heated at 70° C. overnight. Additional ethyl 4-bromobutanoate (0.061 ml, 0.424 mmol) and DIPEA (0.074 ml, 0.424 mmol) were added and the reaction heated for a further 5 hrs. The cooled reaction was diluted with EtOAc/water, separated, the organics dried over magnesium sulphate and evaporated. Purified by flash chromatography eluting with EtOAc/iso-hexane 1:2 to give the title compound (135 mg) as a colourless oil. MS (ES): $C_{26}H_{30}{}^{35}ClN_3O_5$ requires 499; found 500 $[M+H]^+$.

Preparation 68 Alternative Preparation

Ethyl 4-[9-(5-{3-chloro-4-[(1-methylethyl)oxy]phenyl}-1,2,4-oxadiazol-3-yl)-2,3-dihydro-1,4-benzoxazepin-4(5H)-yl]butanoate

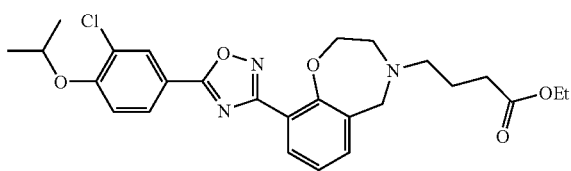

A mixture of 9-(5-{3-chloro-4-[(1-methylethyl)oxy]phenyl}-1,2,4-oxadiazol-3-yl)-2,3,4,5-tetrahydro-1,4-benzoxazepine hydrochloride (Example 31) (20 g, 47.4 mmol), potassium carbonate (16.4 g, 118 mmol) and potassium iodide (7.86 g, 47.4 mmol) in N,N-dimethylformamide (DMF) (250 ml) was treated with ethyl 4-bromobutanoate (7.46 ml, 52.1 mmol) and the resulting mixture stirred at 80° C. under nitrogen for 180 minutes. The mixture was allowed to cool and poured into water (1000 ml). The resulting precipitate was extracted into ethyl acetate (3×250 ml) and the extracts combined, washed with water (2×250 ml), then brine (150 ml), dried (sodium sulphate) and evaporated to give a colourless viscous oil. The crude material was purified by chromatography on silica, eluting with a 20-100% gradient of ethyl acetate in isohexane to give the title compound as a colourless, viscous oil which crystallised on standing (18.3 g).

MS (ES): $C_{26}H_{30}{}^{35}ClN_3O_5$ requires 499; found 500 $[M+H]^+$.

Preparation 69

Ethyl 4-[9-(5-{3-cyano-4-[(1-methylethyl)oxy]phenyl}-1,2,4-oxadiazol-3-yl)-2,3-dihydro-1,4-benzoxazepin-4(5H)-yl]butanoate

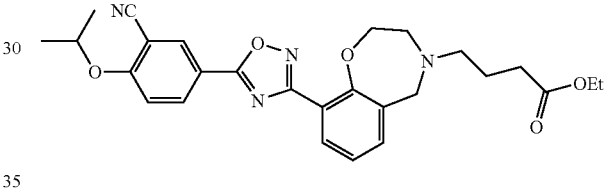

Prepared in a similar way to Preparation 68 from Example 32. MS (ES): $C_{27}H_{30}N_4O_5$ requires 490; found 491 $[M+H]^+$.

Preparation 70

Methyl 5-bromo-2-{[2-({[(1,1-dimethylethyl)oxy]carbonyl}amino)ethyl]oxy}benzoate

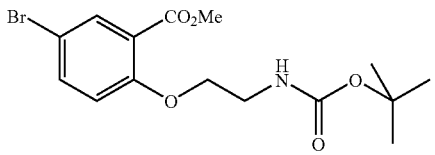

DIAD (9.62 g, 47.6 mmol) was added to a mixture of methyl 5-bromo-2-hydroxybenzoate (10 g, 43.3 mmol), 1,1-dimethylethyl (2-hydroxyethyl)carbamate (6.98 g, 43.3 mmol) and triphenylphosphine (12.47 g, 47.6 mmol) in THF (250 ml) and stirred at RT for 2.5 hr. Additional triphenylphosphine (2.5 g) was added followed by DIAD (4 ml) and the mixture left standing overnight. Evaporation and purification by flash chromatography eluting with 25% EtOAc/hexane gave the title compound as a yellow oil (8.92 g). MS (ES): $C_{15}H_{20}{}^{81}BrNO_5$ requires 375; found 276 $[M+H-100]^+$.

Preparation 71

7-Bromo-3,4-dihydro-1,4-benzoxazepin-5(2H)-one

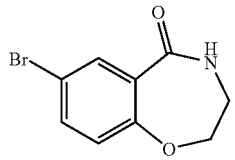

A solution of methyl 5-bromo-2-{[2-({[(1,1-dimethylethyl)oxy]carbonyl}amino)ethyl]oxy}benzoate (Preparation 70) (8.92 g, 23.8 mmmol) in DCM (18 ml) was treated with TFA (7 ml) and stirred for 5 hrs. Additional (2 ml) TFA was added and the reaction left overnight. The solvent was evaporated, re-evaporated with toluene (5×) and dissolved in toluene (50 ml). The resulting residue was treated with triethylamine (4 equiv) and heated at 100° C. overnight then evaporated. The residue was purified by flash chromatography twice eluting with 50% EtOAc/hexane then 40-45% EtOAc/hexane. The fractions were evaporated to give the title compound (3.4 g) as a white solid. MS (ES): $C_9H_8{}^{81}BrNO_2$ requires 243; found 244 $[M+H]^+$.

Preparation 72

7-Bromo-2,3,4,5-tetrahydro-1,4-benzoxazepine

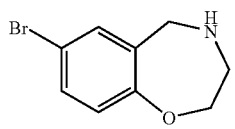

A solution of 7-bromo-3,4-dihydro-1,4-benzoxazepin-5(2H)-one (Preparation 71) (3.28 g, 13.55 mmol) in tetrahydrofuran (THF) (30 ml) was stirred under argon. Borane tetrahydrofuran complex (81 ml, 81 mmol) was added slowly and the solution stirred at RT for 1.5 hrs. The solution was heated at 65° C. overnight. The reaction was cooled and MeOH (20 ml) added dropwise until fizzing ceased. Then 2M HCl (100 ml) was added and the reaction heated at reflux for 1 hour before being cooling and solvent removal by evaporation. The reaction mixture was partitioned between EtOAc/Water and separated. The aqueous layer was basified with 2M NaOH, extracted with EtOAc, dried over magnesium sulphate and evaporated to give a colourless oil (1 g). Precipitated solid from the initial EtOAc layer was filtered and dried. This solid was dissolved in EtOAc/2M NaOH, separated and the organic layer dried over magnesium sulphate and evaporated to give a colourless oil (1.6 g). The 2 products were combined to give the title compound (2.6 g) as a colourless oil. MS (ES): $C_9H_{10}{}^{81}BrNO$ requires 229; found 230 $[M+H]^+$.

Preparation 73

1,1-Dimethylethyl 7-bromo-2,3-dihydro-1,4-benzoxazepine-4(5H)-carboxylate

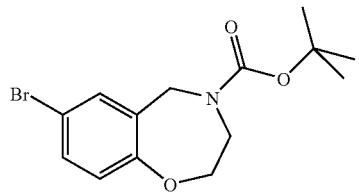

7-Bromo-2,3,4,5-tetrahydro-1,4-benzoxazepine (Preparation 72) (2.15 g, 9.43 mmol) was dissolved in dichloromethane (20 ml). Added triethylamine (1.445 ml, 10.37 mmol) and bis(1,1-dimethylethyl) dicarbonate (2.263 g, 10.37 mmol). Stirred for 4 hours then added dichloromethane and washed with water (3×20 ml). Dried the mixture (MgSO$_4$) and evaporated. Separated on biotage column eluting with (EtOAc/Hexane 1:9) and evaporated to give the title compound (2.76 g). MS (ES): $C_{14}H_{18}{}^{81}BrNO_3$ requires 329; found 230 $[M+H-100]^+$.

Preparation 74

1,1-Dimethylethyl 7-cyano-2,3-dihydro-1,4-benzoxazepine-4(5H)-carboxylate

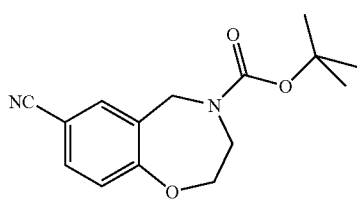

A mixture of 1,1-dimethylethyl 7-bromo-2,3-dihydro-1,4-benzoxazepine-4(5H)-carboxylate (Preparation 73) (2.67 g, 8.14 mmol), zinc cyanide (1.715 g, 16.27 mmol) and tetakis(triphenylphosphine)palladium(0) (1.410 g, 1.220 mmol) in DMF (30 ml) was heated at 80° C. overnight. Additional tetakis(triphenylphosphine)palladium(0) (700 mg) was added and the yellow suspension heated at 80° C. for a further 5 hrs. The cooled reaction mixture was diluted with EtOAc/water, separated, and organics dried over anhydrous magnesium sulphate and evaporated. The crude was purified by flash chromatography eluting with EtOAc/iso-hexane 1:9. The combined fractions were evaporated to give the title compound (2.01 g) as a yellow solid. 6H (CDCl$_3$, 400 MHz): 1.42 (9H, br.s), 3.81 (2H, t), 4.09 (2H, m), 4.43 (1H, s), 4.51 (1H, s), 7.09 (1H, m), 7.47-7.59 (2H, m).

Preparation 75

1,1-Dimethylethyl 7-[(hydroxyamino)(imino)methyl]-2,3-dihydro-1,4-benzoxazepine-4(5H)-carboxylate

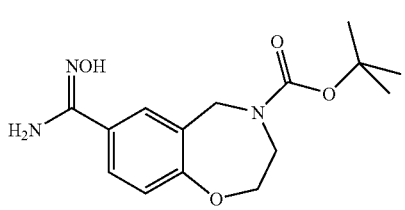

A suspension of 1,1-dimethylethyl 7-cyano-2,3-dihydro-1,4-benzoxazepine-4(5H)-carboxylate (Preparation 74) (2.016 g, 7.35 mmol), hydroxylamine hydrochloride (1.021 g, 14.70 mmol) and sodium bicarbonate (3.09 g, 36.7 mmol) in ethanol (30 ml) was heated at 60° C. overnight. The grey solid was removed by filtration and the filtrate evaporated. The resulting residue was dissolved in EtOAc, washed with water (3×20 ml), dried (MgSO$_4$) and evaporated to give the title compound (1.77 g) as a white solid. MS (ES): $C_{15}H_{21}N_3O_4$ requires 307; found 308 [M+H]$^+$.

Preparation 76

1,1-Dimethylethyl 7-(5-{3-cyano-4-[(1-methylethyl)oxy]phenyl}-1,2,4-oxadiazol-3-yl)-2,3-dihydro-1,4-benzoxazepine-4(5H)-carboxylate

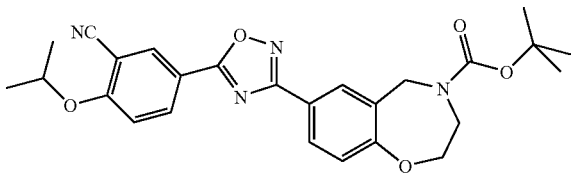

A solution of 1,1-dimethylethyl 7-[(hydroxyamino)(imino)methyl]-2,3-dihydro-1,4-benzoxazepine-4(5H)-carboxylate (Preparation 75) (0.84 g, 2.73 mmol), 3-cyano-4-[(1-methylethyl)oxy]benzoic acid (can be prepared as described in WO2005/58848) (0.617 g, 3.01 mmol), EDC (0.786 g, 4.10 mmol) and HOBT (0.502 g, 3.28 mmol) in DMF (10 ml) was stirred at RT overnight. Additional EDC (0.4 g) was added and the reaction stirred for 3 hours. Then additional 3-cyano-4-[(1-methylethyl)oxy]benzoic acid (0.3 g) was added, the reaction heated at 120° C. for 1 hour and left standing overnight. The reaction mixture was partitioned between EtOAc/water, and the organic layer collected, dried (MgSO$_4$) and evaporated. The resulting crude was purified by flash chromatography eluting with EtOAc/iso-hexane 20-30%. Analysis of the puried fractions by LCMS showed some 3-cyano-4-[(1-methylethyl)oxy]benzoic acid present so sodium bicarbonate and EtOAc was added. The EtOAc layer was separated, dried (MgSO$_4$) and evaporated to give the title compound (410 mg) as a white solid. MS (ES): $C_{26}H_{28}N_4O_5$ requires 476; found 421 [M+H−56]$^+$.

Preparation 77

1,1-Dimethylethyl 7-(5-{3-chloro-4-[(1-methylethyl)oxy]phenyl}-1,2,4-oxadiazol-3-yl)-2,3-dihydro-1,4-benzoxazepine-4(5H)-carboxylate

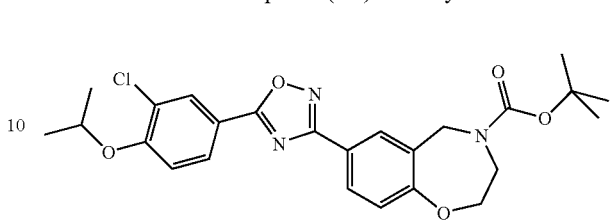

The title compound was prepared by a similar method to Preparation 76 using Preparation 75 and the appropriate acid. MS (ES): $C_{25}H_{28}{}^{35}ClN_3O_5$ requires 485; found 430 [M+H−56]$^+$.

Preparation 78

Ethyl 3-[7-(5-{3-cyano-4-[(1-methylethyl)oxy]phenyl}-1,2,4-oxadiazol-3-yl)-2,3-dihydro-1,4-benzoxazepin-4(5H)-yl]propanoate

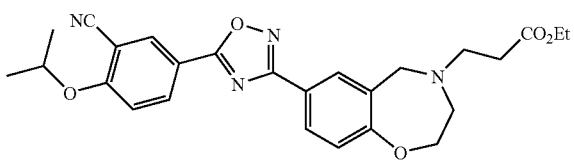

To a solution of 2-[(1-methylethyl)oxy]-5-[3-(2,3,4,5-tetrahydro-1,4-benzoxazepin-7-yl)-1,2,4-oxadiazol-5-yl]benzonitrile hydrochloride (Example 35) (0.101 g, 0.268 mmol) in acetonitrile (2 ml) was added DIPEA (0.094 ml, 0.537 mmol) and ethyl 3-bromopropanoate (0.051 ml, 0.402 mmol). The reaction mixture was stirred and heated at 80° C. under Argon for 6 hours. DIPEA (0.094 ml, 0.537 mmol) and ethyl 3-bromopropanoate (0.051 ml, 0.402 mmol) were added and the reaction stirred and heated at 80° C. under Argon overnight. Additional quantities of DIPEA (0.094 ml, 0.537 mmol) and ethyl 3-bromopropanoate (0.051 ml, 0.402 mmol) were added and the reaction heated again. The reaction mixture was dissolved in EtOAc, washed with saturated NaHCO$_3$ solution (3×15 ml) and water (15 ml), dried (MgSO$_4$) and evaporated. The resulting crude was purified by flash chromatography, eluting with EtOAc/iso-Hexane 10-20% (Biotage Column) to give the title compound (92 mg). MS (ES): $C_{26}H_{28}N_4O_5$ requires 476; found 477 [M+H]$^+$.

Preparation 79

Ethyl 3-[7-(5-{3-chloro-4-[(1-methylethyl)oxy]phenyl}-1,2,4-oxadiazol-3-yl)-2,3-dihydro-1,4-benzoxazepin-4(5H)-yl]propanoate

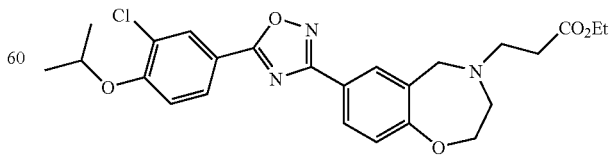

Prepared by a similar method to Preparation 78 from Example 36. MS (ES): $C_{25}H_{28}{}^{35}ClN_3O_5$ requires 485; found 486 [M+H]$^+$.

Preparation 80

Ethyl 4-[7-(5-{3-cyano-4-[(1-methylethyl)oxy]phenyl}-1,2,4-oxadiazol-3-yl)-2,3-dihydro-1,4-benzoxazepin-4(5H)-yl]butanoate

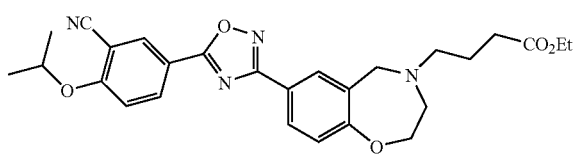

A solution of 2-[(1-methylethyl)oxy]-5-[3-(2,3,4,5-tetrahydro-1,4-benzoxazepin-7-yl)-1,2,4-oxadiazol-5-yl]benzonitrile hydrochloride (Example 35) (0.104 g, 0.276 mmol) was stirred in acetonitrile (2 ml). DIPEA (0.097 ml, 0.553 mmol) and ethyl 4-bromobutanoate (0.059 ml, 0.414 mmol) were added and the reaction mixture stirred and heated at 80° C. under Argon for 6 hours. Additional ethyl 4-bromobutanoate (0.059 ml, 0.414 mmol) and DIPEA (0.097 ml, 0.553 mmol) were added and the reaction mixture stirred and heated at 80° C. under argon overnight. Then the reaction mixture was dissolved in EtOAc, washed with saturated NaHCO$_3$ solution (3×15 ml) and water (15 ml) and the organics dried (MgSO$_4$) and evaporated. The crude was purified by flash chromatography, eluting with EtOAc/iso-Hexane 10-20% (Biotage Column) and evaporated to give the title compound (84 mg) as an oil. MS (ES): $C_{27}H_{30}N_4O_5$ requires 490; found 491 [M+H]$^+$.

Preparation 81

Ethyl 4-[7-(5-{3-chloro-4-[(1-methylethyl)oxy]phenyl}-1,2,4-oxadiazol-3-yl)-2,3-dihydro-1,4-benzoxazepin-4(5H)-yl]butanoate

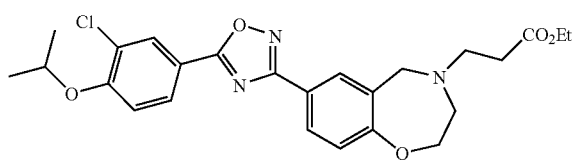

7-(5-{3-Chloro-4-[(1-methylethyl)oxy]phenyl}-1,2,4-oxadiazol-3-yl)-2,3,4,5-tetrahydro-1,4-benzoxazepine (0.105 g, 0.272 mmol) was stirred in acetonitrile (2 ml). DIPEA (0.095 ml, 0.544 mmol) and ethyl 4-bromobutanoate (0.058 ml, 0.408 mmol) were added and the reaction mixture heated at 80° C. under Argon for 5 hours. Additional DIPEA (0.095 ml, 0.544 mmol) and ethyl 4-bromobutanoate (0.058 ml, 0.408 mmol) were added and the reaction mixture heated at 80° C. overnight. Then the reaction mixture was dissolved in EtOAc (20 ml), washed with NaHCO$_3$ (aq) (15 ml×3) and with water (15 ml×3) and the organics dried (MgSO$_4$) and evaporated. The crude was purified by flash chromatography eluting with EtOAc/iso-Hexane 20/30% (Biotage column), and evaporated to give the title compounds as an oil (80 mg). MS (ES): $C_{26}H_{30}{}^{35}ClN_3O_5$ requires 499; found 500 [M+H]$^+$.

Preparation 82

1,1-Dimethylethyl 8-(5-{3-cyano-4-[(1-methylethyl)oxy]phenyl}-1,2,4-oxadiazol-3-yl)-2,3-dihydro-1,4-benzoxazepine-4(5H)-carboxylate

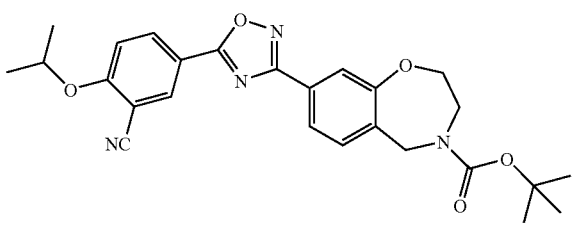

Prepared from Preparation 33 using the appropriate acid using the method described in Preparation 34. MS (ES): $C_{26}H_{28}N_4O_5$ requires 476; found 477 [M+H]$^+$.

Preparation 83

Ethyl 4-[8-(5-{3-cyano-4-[(1-methylethyl)oxy]phenyl}-1,2,4-oxadiazol-3-yl)-2,3-dihydro-1,4-benzoxazepin-4(5H)-yl]butanoate

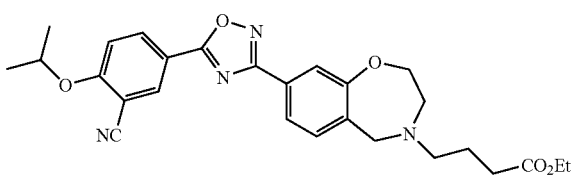

Prepared from Example 41 using the method described in Preparation 36. MS (ES): $C_{27}H_{30}N_4O_5$ requires 490; found 491 [M+H]$^+$.

Preparation 84

9-(Methyloxy)-2,3,4,5-tetrahydro-1,4-benzoxazepine

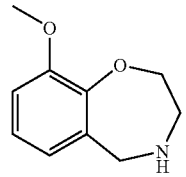

A solution of 9-(methyloxy)-3,4-dihydro-1,4-benzoxazepin-5(2H)-one (Preparation 57) (50 g, 259 mmol) in dry tetrahydrofuran (THF) (500 ml) was cooled to ca 5° C. and treated slowly over ca 20 mins with 1M lithium aluminium hydride in THF (259 ml, 259 mmol), keeping internal temperature below 15° C. When the addition was complete, the mixture was allowed to warm to room temperature and stirred for 2 hours, then heated at reflux for 2 hours. The mixture was allowed to cool to room temperature and was then cooled to ca −15° C. in a dry ice/acetone bath and treated cautiously with a 2:1 mixture of THF-water (100 ml). When the addition was complete the mixture was treated with more water (220 ml) and then with 2M sodium hydroxide until a filterable solid was formed. This was removed by filtration and washed with ethyl acetate (500 ml). The filtrate was washed with brine (500 ml) and the aqueous phase extracted with ethyl acetate (2×250 ml). The organic extracts were combined, dried (sodium sulphate) and evaporated to give the title compound as an off white crystalline solid. (42.9 g)

MS (ES): $C_{10}H_{13}NO_2$ requires 179; found 180 $[M+H]^+$.

Preparation 85

2,3,4,5-tetrahydro-1,4-benzoxazepin-9-ol hydrobromide

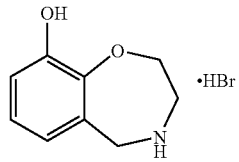

A suspension of 9-(methyloxy)-2,3,4,5-tetrahydro-1,4-benzoxazepine (Preparation 84) (43.4 g, 242 mmol) in 33% HBr in acetic acid (300 ml, 1823 mmol) was heated at 80° C. overnight. The mixture was allowed to cool to room temperature then treated with diethyl ether (300 ml) and stirred for 30 minutes. The resulting solid was collected by filtration, washed with diethyl ether (300 ml) and dried under vacuum at 40° C. to give the title compound as a pale brown powder (55.1 g)

MS (ES): $C_9H_{11}NO_2$ requires 165; found 166 $[M+H]^+$.

Preparation 86

Ethyl [9-(5-{3-cyano-4-[(1-methylethyl)oxy]phenyl}-1,2,4-oxadiazol-3-yl)-2,3-dihydro-1,4-benzoxazepin-4(5H)-yl]acetate

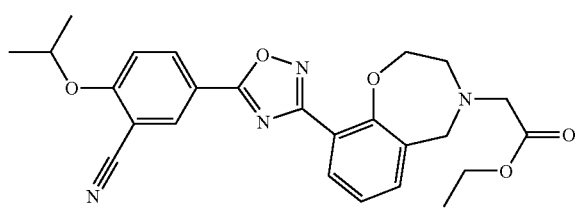

To a solution of 2-[(1-methylethyl)oxy]-5-[3-(2,3,4,5-tetrahydro-1,4-benzoxazepin-9-yl)-1,2,4-oxadiazol-5-yl]benzonitrile (Example 32) (110 mg, 0.224 mmol) in acetonitrile (10 mL) was added N,N-diisopropylethylamine (0.08 mL, 0.449 mmol) and ethyl bromoacetate (0.05 mL, 0.449 mmol). The reaction mixture was heated to 80° C. for 2 hours. The mixture was allowed to cool to room temperature. The solvent was evaporated to give the title compound as a brown solid (100 mg).

MS (ES) $C_{25}H_{26}N_4O_5$ requires 462 Found 463 $[M+H]^+$.

Preparation 87

Ethyl 5-[9-(5-{3-cyano-4-[(1-methylethyl)oxy]phenyl}-1,2,4-oxadiazol-3-yl)-2,3-dihydro-1,4-benzoxazepin-4(5H)-yl]pentanoate

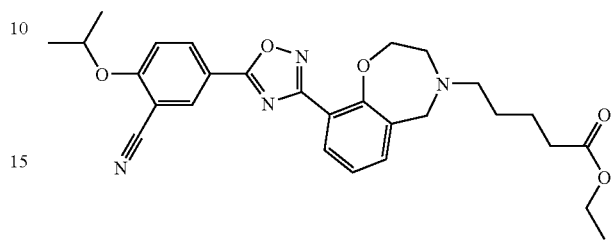

To a solution of 2-[(1-methylethyl)oxy]-5-[3-(2,3,4,5-tetrahydro-1,4-benzoxazepin-9-yl)-1,2,4-oxadiazol-5-yl]benzonitrile (Example 32) (100 mg, 0.204 mmol) in acetonitrile (10 ml) was added N,N-diisopropylethylamine (0.07 ml, 0.408 mmol) and ethyl 5-bromopentanoate (0.06 mL, 0.408 mmol). The reaction mixture was heated to 80° C. overnight then was allowed to cool and the solvent evaporated. Purification of the residue by flash chromatography, eluting with (40-100% ethyl acetate in cyclohexane) gave the title compound as an off white solid (70 mg).

MS (ES) $C_{28}H_{32}N_4O_5$ requires 504 Found 505 $[M+H]^+$.

Preparation 88

Ethyl 3-[9-(5-{3-chloro-4-[(1-methylethyl)oxy]phenyl}-1,2,4-oxadiazol-3-yl)-2,3-dihydro-1,4-benzoxazepin-4(5H)-yl]propanoate

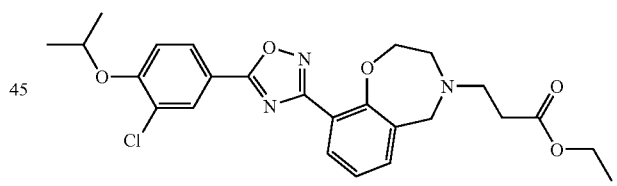

To a solution of 9-(5-{3-chloro-4-[(1-methylethyl)oxy]phenyl}-1,2,4-oxadiazol-3-yl)-2,3,4,5-tetrahydro-1,4-benzoxazepine hydrochloride (Example 31) (260 mg, 0.62 mmol) in acetonitrile (15 ml) was added N,N-diisopropylethylamine (0.214 ml, 1.23 mmol) followed by ethyl 3-bromopropanoate (0.158 ml, 1.231 mmol). The reaction mixture was heated at 80° C. overnight. A further 1 equiv. of N,N-diisopropylethylamine and ethyl 3-bromopropanoate were added and heating continued overnight. The reaction mixture was cooled and evaporated. Purification of the residue by column chromatography, eluting with 50-65% ethyl acetate in cyclohexane to give the title compound as a yellow oil (80 mg).

MS (ES) $C_{25}H_{28}{}^{35}ClN_3O_5$ requires 485 Found 486 $[M+H]^+$.

Preparation 89

1,1-Dimethylethyl 9-(5-{5-chloro-6-[(1-methylethyl)oxy]-3-pyridinyl}-1,2,4-oxadiazol-3-yl)-2,3-dihydro-1,4-benzoxazepine-4(5H)-carboxylate

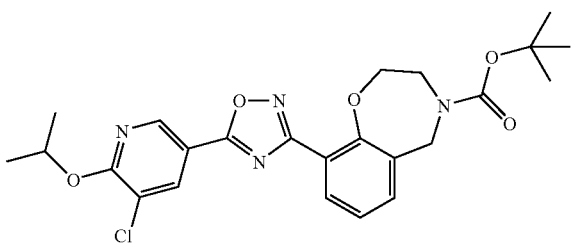

Triethylamine (0.281 ml, 2.02 mmol) was added to a stirred solution of 5-chloro-6-[(1-methylethyl)oxy]-3-pyridinecarboxylic acid (may be prepared as described in WO9702244; 217 mg, 1.01 mmol) in N,N-dimethylformamide (20 ml) followed by hydroxybenzotriazole hydrate (185 mg, 1.21 mmol) then 1-(3-dimethylaminopropyl)-3-ethylcarbodiimide hydrochloride (232 mg, 1.21 mmol) and lastly 1,1-dimethylethyl 9-[(hydroxyamino)(imino)methyl]-2,3-dihydro-1,4-benzoxazepine-4(5H)-carboxylate (Preparation 65) (310 mg, 1.009 mmol). The reaction mixture was heated to 60° C. for 48 hours, then allowed to cool before diluting with ethyl acetate and washing with water. The organic phase was dried and evaporated. Purification of the residue by column chromatography, eluting with 15-25% ethyl acetate in cyclohexane to give the title compound as an amber coloured gum (280 mg).

MS (ES) $C_{24}H_{27}{}^{35}ClN_4O_5$ requires 486 found 487 [M+H]$^+$.

Preparation 90

9-(5-{5-Chloro-6-[(1-methylethyl)oxy]-3-pyridinyl}-1,2,4-oxadiazol-3-yl)-2,3,4,5-tetrahydro-1,4-benzoxazepine hydrochloride

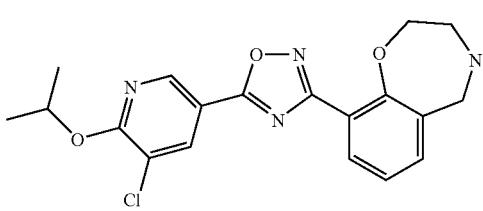

A mixture of 1,1-dimethylethyl 9-(5-{5-chloro-6-[(1-methylethyl)oxy]-3-pyridinyl}-1,2,4-oxadiazol-3-yl)-2,3-dihydro-1,4-benzoxazepine-4(5H)-carboxylate (Preparation 89) (190 mg, 0.390 mmol), 4M hydrogen chloride in dioxane (1 ml, 4.00 mmol) and 1,4-dioxane (10 ml) was stirred at 60° C. overnight. The reaction mixture was cooled and a white precipitate formed. The solid was filtered off to give the product as a white solid (170 mg). MS (ES) $C_{19}H_{19}{}^{35}ClN_4O_3$ requires 386 Found 387 [M+H]$^+$.

Preparation 91

Ethyl 3-[9-(5-{5-chloro-6-[(1-methylethyl)oxy]-3-pyridinyl}-1,2,4-oxadiazol-3-yl)-2,3-dihydro-1,4-benzoxazepin-4(5H)-yl]propanoate

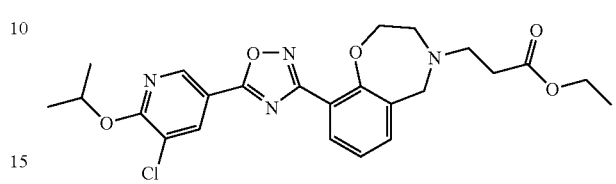

To a solution of 9-(5-{5-chloro-6-[(1-methylethyl)oxy]-3-pyridinyl}-1,2,4-oxadiazol-3-yl)-2,3,4,5-tetrahydro-1,4-benzoxazepine hydrochloride (Preparation 90) (80 mg, 0.189 mmol) in acetonitrile (10 ml) was added N,N-diisopropylethylamine (0.066 ml, 0.378 mmol) followed by ethyl 3-bromopropanoate (0.048 ml, 0.378 mmol). The reaction mixture was heated at 80° C. overnight. A further 1 equivalent of N,N-diisopropylethylamine and ethyl 3-bromopropanoate were added and heating continued overnight. The reaction mixture was cooled and evaporated. The residue was purified by column chromatography on silica. Elution with 40-60% ethyl acetate in cyclohexane to give the title compound as an olive green coloured oil (28 mg).

MS (ES) $C_{24}H_{27}{}^{35}ClN_4O_5$ requires 486 Found 487 [M+H]$^+$.

Preparation 92

Ethyl 3-[9-(5-{3-cyano-4-[(1-methylethyl)oxy]phenyl}-1,2,4-oxadiazol-3-yl)-2,3-dihydro-1,4-benzoxazepin-4(5H)-yl]propanoate

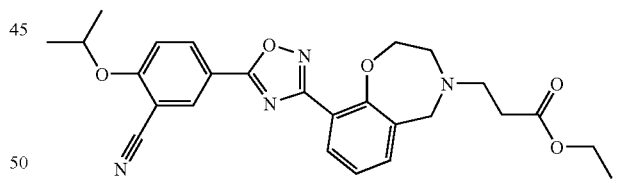

To a solution of 2-[(1-methylethyl)oxy]-5-[3-(2,3,4,5-tetrahydro-1,4-benzoxazepin-9-yl)-1,2,4-oxadiazol-5-yl]benzonitrile hydrochloride (Example 32) (90 mg, 0.218 mmol) in acetonitrile (10 ml) was added N,N-diisopropylethylamine (0.076 ml, 0.436 mmol) followed by ethyl 3-bromopropanoate (0.056 ml, 0.436 mmol). The reaction mixture was heated at 80° C. overnight. A further 1 equivalent of N,N-diisopropylethylamine and ethyl 3-bromopropanoate were added and heating continued overnight. The reaction mixture was cooled and evaporated. Purification of the residue by column chromatography on silica, eluting with 60-70% ethyl acetate in cyclohexane to give the title compound as a brown oil (40 mg).

MS (ES) $C_{10}H_{13}NO_2$ requires 476 Found 477 [M+H]$^+$.

Preparation 93

1-Methylethyl 5-cyano-6-[(1-methylethyl)oxy]-3-pyridinecarboxylate

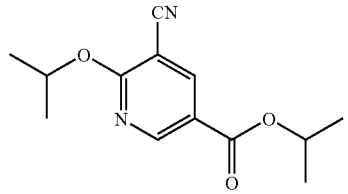

A mixture of 1-methylethyl 5-chloro-6-[(1-methylethyl)oxy]-3-pyridinecarboxylate (may be prepared as described in WO9702244; 7.73 g, 30.0 mmol) in dry N,N-dimethylformamide (DMF) (60 ml) and zinc cyanide (4.23 g, 36.0 mmol) at room temperature was de-gassed and flushed with nitrogen several times. Tetrakis(triphenylphosphine)palladium(0) (3.47 g, 3.00 mmol) was added and the degassing procedure repeated. The reaction mixture was then heated to 100° C. for 24 hrs. The reaction mixture was allowed to cool to room temperature, then filtered to remove solid residues, washing with a little DMF. A further quantity of zinc cyanide (4.23 g, 36.0 mmol) and a different batch of tetrakis(triphenylphosphine)palladium(0) (3.47 g, 3.00 mmol) were added, with the same de-gassing and nitrogen flush. Heating was then continued at 100° C. for 2 hr.

The reaction mixture was allowed to cool to room temperature again, diluted with ethyl acetate and filtered to remove the solid residues. The solution was concentrated to an oil. On standing, more solid separated. The mixture was extracted with ethyl acetate, then the organic phase washed with water (2×), brine, dried and concentrated to an orange oil. The crude material was loaded onto a silica gel column and chromatographed, eluting with a gradient of 0-10% ethyl acetate in cyclohexane to give 3.87 g of product still contaminated with triphenylphosphine. Further purification by chromatography, eluting with a gradient of 0-5% ethyl acetate in cyclohexane gave the title compound (1.32 g), MS (ES) $C_{13}H_{16}N_2O_3$ requires 248; found 248 $[M+H]^+$.

Preparation 94

5-Cyano-6-[(1-methylethyl)oxy]-3-pyridinecarboxylic acid

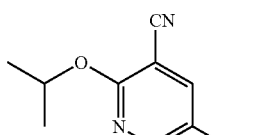

1-Methylethyl 5-cyano-6-[(1-methylethyl)oxy]-3-pyridinecarboxylate (Preparation 93) (1.28 g, 5.15 mmol) in ethanol (20 ml) was treated with sodium hydroxide (5.15 ml, 10.30 mmol) and the mixture stirred at room temperature to give a homogeneous solution, until LC/MS showed no starting material. The mixture was concentrated to remove ethanol. The residue was diluted with water, then acidfied with 2M HCl to give a thick white precipitate. The solid was filtered off, washed with water and dried overnight in vacuo at 60° C., to give the title compound (1.07 g), MS (ES) $C_{10}H_{10}N_2O_3$ requires 206; found 205 $[M-H]^+$.

Preparation 95

1,1-Dimethylethyl 7-(5-{5-cyano-6-[(1-methylethyl)oxy]-3-pyridinyl}-1,2,4-oxadiazol-3-yl)-1,2,4,5-tetrahydro-3H-3-benzazepine-3-carboxylate

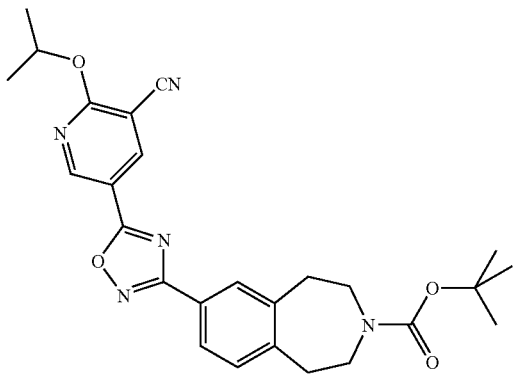

A solution of 5-cyano-6-[(1-methylethyl)oxy]-3-pyridinecarboxylic acid (Preparation 94) (206 mg, 0.999 mmol) in dichloromethane (5 ml) at room temperature was treated with oxalyl chloride (0.262 ml, 3.00 mmol) and 1 drop of N,N-dimethylformamide (DMF). After 1 hr, the solution was concentrated to give the crude acid chloride as a yellow gum.

1,1-Dimethylethyl 7-[(hydroxyamino)(imino)methyl]-1,2,4,5-tetrahydro-3H-3-benzazepine-3-carboxylate (Preparation 41) (305 mg, 0.999 mmol) in DMF (5.00 ml) was treated with triethylamine (0.17 ml, 1.20 mmol) followed by the crude acid chloride (described above) in DMF (1 ml). After 10 mins the mixture was heated to 120° C. After 2 hrs the reaction mixture was allowed to cool to room temperature and concentrated. The residue was partitioned between ethyl acetate and dilute sodium hydroxide. The organic layer was washed with brine, dried and concentrated to give a yellow gum, which crystallised on standing. The crude material was loaded onto a silca gel column and chromatographed eluting with a gradient of 0-20% ethyl acetate in cyclohexane to give the title compound as a colourless crystalline solid (224 mgs), MS (ES) $C_{26}H_{29}N_5O_4$ requires 475; found 420 $[M+-tBu]^+$.

Preparation 96

1,1-Dimethylethyl 7-(5-{5-chloro-6-[(1-methylethyl)oxy]-3-pyridinyl}-1,2,4-oxadiazol-3-yl)-1,2,4,5-tetrahydro-3H-3-benzazepine-3-carboxylate

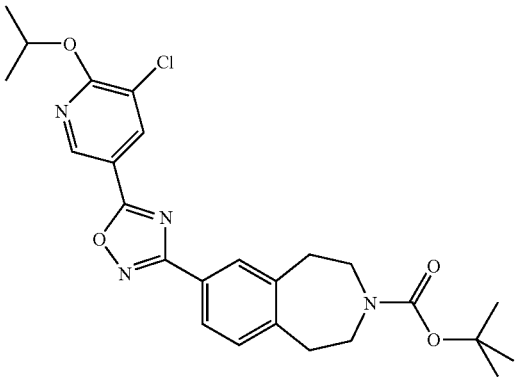

A suspension of 5-chloro-6-[(1-methylethyl)oxy]-3-pyridinecarboxylic acid (may be prepared as described in WO9702244; 215 mg, 0.999 mmol) in dichloromethane (3 ml) at room temperature was treated with oxalyl chloride (0.26 ml, 3.00 mmol) and 1 drop of N,N-dimethylformamide (DMF). After 2 hrs the solution was concentrated to give the crude acid chloride as a yellow oil.

1,1-Dimethylethyl 7-[(hydroxyamino)(imino)methyl]-1,2,4,5-tetrahydro-3H-3-benzazepine-3-carboxylate (Preparation 41) (305 mg, 0.999 mmol) was dissolved in dry DMF (2 ml), treated with triethylamine (0.17 ml, 1.20 mmol) and stirred at room temperature. A solution of the crude acid chloride (described above) in dry DMF (2 ml) was added to give a pale yellow, turbid solution. The mixture was stirred for 1.5 hr at room temperature, then heated to 120° C. for 2 hrs. The reaction mixture was allowed to cool to room temperature, and concentrated. The residue was partitioned between ethyl acetate and water. The organic layer was washed with water then brine, dried and concentrated to a cream foam. The crude material was loaded onto a silica gel column and chromatographed eluting with a gradient of 0-15% ethyl acetate in cyclohexane to give title compound was obtained as a colourless foam/solid, (305 mgs), MS (ES) $C_{25}H_{29}{}^{35}ClN_4O_4$ requires 484; found 429 [M+–tBu]$^+$.

Preparation 97

Ethyl 4-[7-(5-{5-chloro-6-[(1-methylethyl)oxy]-3-pyridinyl}-1,2,4-oxadiazol-3-yl)-1,2,4,5-tetrahydro-3H-3-benzazepin-3-yl]butanoate

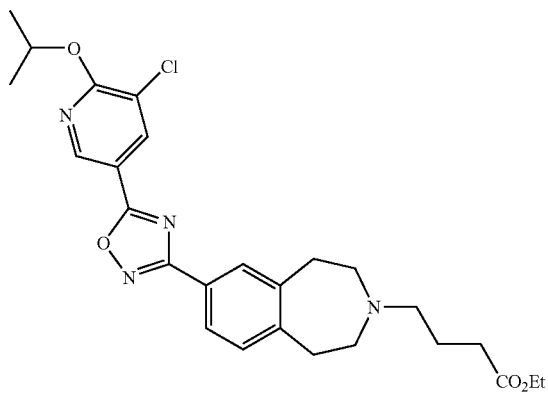

7-(5-{5-Chloro-6-[(1-methylethyl)oxy]-3-pyridinyl}-1,2,4-oxadiazol-3-yl)-2,3,4,5-tetrahydro-1H-3-benzazepine hydrochloride (Example 50) (192 mg, 0.499 mmol) in N,N-dimethylformamide (2 ml) at room temperature was treated with potassium carbonate (103 mg, 0.748 mmol) and ethyl 4-bromobutanoate (0.09 ml, 0.60 mmol). The mixture was heated to 100° C. After ca. 2 hrs, the mixture was cooled and concentrated. The residue was partitioned between ethyl acetate and water. The ethyl acetate layer was washed with brine, dried and concentrated to a colourless gum. The crude material was loaded onto a silica gel column and chromatographed, eluting with a gradient of 80-100% ethyl acetate in cyclohexane gave the title compound as a colourless gum, which slowly crystallized on standing (185 mgs).

MS (ES) $C_{26}H_{31}{}^{35}ClN_4O_4$ requires 498; found 499 [M+H]$^+$.

Preparation 98

3-Bromo-2-hydroxybenzaldehyde

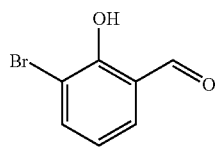

Triethylamine (72 ml, 520 mmol) was added over 10 minutes to a suspension of paraformaldehyde (23.4 g, 780 mmol) and dry magnesium dichloride (49.5 g, 520 mmol, Aldrich; CAS 7786-30-3) in THF (1 liter) under nitrogen at room temperature. The resulting mixture was stirred for 20 min, then 2-bromophenol (45 g, 260 mmol) was added over 5 minutes via syringe. The resulting mixture was stirred under gentle reflux for 6 h then cooled to room temperature. The solution was left over the weekend and then diluted with diethylether (500 ml). The organic phase was washed with a 2N hydrochloric acid (500 ml) and the two phases were separated. The insoluble material was filtered off and the organic phase was washed twice with 2N hydrochloric acid (500 ml) then five times with water (100 ml), dried over magnesium sulphate and concentrated in vacuo to give the title compound as a colourless solid (46.5 g). MS (ES) $C_7H_5{}^{79}BrO_2$ requires 200 found 199 [M−H]$^+$.

Preparation 99

2-Bromo-6-{[(2-hydroxyethyl)amino]methyl}phenol

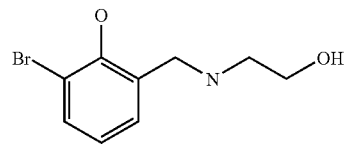

To a solution of 3-bromo-2-hydroxybenzaldehyde (Preparation 98) (9.6 g, 47.8 mmol) in tetrahydrofuran (250 ml) at 0° C. under nitrogen was added 2-aminoethanol (3.02 ml, 50.1 mmol) then finely powdered sodium triacetoxyborohydride (10.6 g, 50.1 mmol) and the resulting mixture was stirred at 0° C. for 1 h, then stirred overnight and concentrated in vacuo. The residue was triturated under dichloromethane (~200 mL) and insoluble material was filtered off. The organic phase was concentrated in vacuo and the residue purified using an SCX column to give the title compound as a white solid (10.1 g). MS (ES) $C_9H_{10}{}^{79}BrNO_2$ requires 243 found 244 [M+H]$^+$.

Preparation 100

1,1-Dimethylethyl [(3-bromo-2-hydroxyphenyl)methyl](2-hydroxyethyl)carbamate

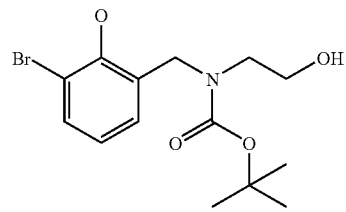

2-Bromo-6-{[(2-hydroxyethyl)amino]methyl}phenol (Preparation 99) (2.3 g, 9.35 mmol) was dissolved in methanol (10 ml) and tetrahydrofuran (40 ml) and the resulting mixture was cooled at 0° C. Triethylamine (1.95 ml, 14.0 mmol), then bis(1,1-dimethylethyl) dicarbonate (2.39 ml, 10.3 mmol) were added and the resulting mixture stirred at this temperature for 2.5 h. Further triethylamine (195 ml, 1.40 mmol) and bis(1,1-dimethylethyl) dicarbonate (239 ml, 1.03 mmol) were added and the resulting mixture was allowed to warm to room temperature and left to stand over the weekend then concentrated in vacuo. The residue was dissolved in ethyl acetate and the organic phase was washed twice with a 2N hydrochloric acid then brine and dried (magnesium sulphate) and concentrated in vacuo. Purification of the residue by flash chromatography on silica gel, eluting with 15-45% ethyl acetate in cyclohexane gave the title compound as a pale yellow oil (3.4 g). MS (ES) $C_{14}H_{20}{}^{79}BrNa_4$ requires 345 found 246 $[M+H—COOC(CH_3)_3]^+$.

Preparation 101

1,1-Dimethylethyl 9-bromo-2,3-dihydro-1,4-benzoxazepine-4(5H)-carboxylate

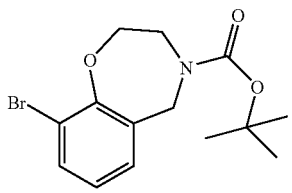

A mixture of 1,1-dimethylethyl [(3-bromo-2-hydroxyphenyl)methyl](2-hydroxyethyl)carbamate (Preparation 100) (2.35 g, 6.79 mmol) and triphenylphosphine (1.96 g, 7.47 mmol) in tetrahydrofuran (40 ml) under nitrogen was cooled to 0° C. Diisopropyl azodicarboxylate (DIAD) (1.47 ml, 7.47 mmol) was added dropwise and the resulting mixture stirred for 1 h then concentrated in vacuo. The solvent was removed and the material washed twice with brine, dried (magnesium sulphate) then concentrated in vacuo. Purification of the residue by flash chromatography on silica gel, eluting with 5-25% ethyl acetate in cyclohexane gave the title compound (1.35 g). MS (ES) $C_{14}H_{18}{}^{79}BrNO_2$ requires 327 found 228 $[M+H—COOC(CH_3)_3]^+$.

Alternative Procedure (from 3-bromo-2-hydroxybenzaldehyde)

3-Bromo-2-hydroxybenzaldehyde (Aldrich; 5.0 g, 24.9 mmol) in ethanol (100 ml) at room temperature was treated with ethanolamine (1.65 ml, 27.4 mmol) and the resulting mixture was stirred for about 1 h. Sodium borohydride (1.129 g, 29.8 mmol) was then added and the resulting mixture heated under reflux for about 2 h then cooled to room temperature and then placed in ice-water, treated with triethylamine (5.2 ml, 37.3 mmol) followed by the portionwise addition of bis(1,1-dimethylethyl)dicarbonate (8.14 g, 37.3 mmol). Once the addition was complete, the resulting mixture was removed from the ice bath and the mixture stirred at room temperature for 30 mins–1 h. The resulting mixture was treated with 2M sodium hydroxide (49.7 ml, 99 mmol) and stirred at 50° C. for 1.5 h, at room temperature overnight, then at 60° C. for 5 h. 2M Sodium hydroxide (49.7 ml, 99 mmol) was added and the resulting mixture stirred at 60° C. for 2 h then at room temperature over the weekend. Most of the ethanol was removed in vacuo and the resulting aqueous phase acidified to pH 5 with 2N hydrochloric acid. The aqueous phase was extracted three times with dichloromethane and the organic phase washed with brine, dried (magnesium sulphate) and concentrated in vacuo. The residue was dissolved in tetrahydrofuran (100 ml) and treated at room temperature with triphenylphosphine (10.44 g, 39.8 mmol) followed by the dropwise addition of diisopropyl azodicarboxylate (DIAD) (7.74 ml, 39.8 mmol). The resulting mixture was briefly cooled using ice-water and then stirred for 1-2 h at room temperature then concentrated in vacuo. The crude material in DCM was loaded onto fine silica in a sinter funnel, washed through with cyclohexane (200 mLs), followed by 3×500 mL portions of 10% EtOAc/cyclohexane. Each portion was concentrated separately. Purification of the residue by flash chromatography on silica gel, eluting with 0-10% ethyl acetate in cyclohexane gave the title compound (6.62 g). MS (ES) $C_{14}H_{18}{}^{79}BrNO_2$ requires 327 found 228 $[M+H—COOC(CH_3)_3]^+$.

Preparation 102

3-Chloro-4-[(1-methylethyl)oxy]benzoyl chloride

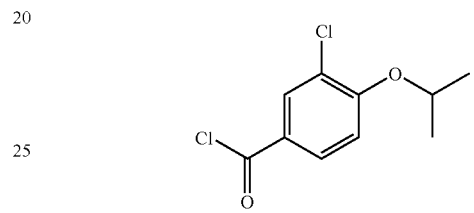

A round bottom flask was charged with 3-chloro-4-[(1-methylethyl)oxy]benzoic acid (available from Paragos Product List, 10.2 g, 47.5 mmol), dichloromethane (158 ml) and oxalyl chloride (8.29 ml, 95 mmol). The reaction mixture was cooled to 0° C. in an ice/water bath prior to the addition of N,N-dimethylformamide (0.158 ml). The solution was allowed to warm to ambient temperature overnight. The solvent was evaporated to yield the title compound as a cream solid (11.4 g). δH (CDCl3, 400 MHz): 1.44 (6H, d), 4.73 (1H, septet), 6.98 (1H, d), 8.0 (1H, dd), 7.98 (1H, d).

EXAMPLE 1

7-(5-{3-Chloro-4-[(1-methylethyl)oxy]phenyl}-1,2,4-oxadiazol-3-yl)-2,3,4,5-tetrahydro-1H-2-benzazepine hydrochloride

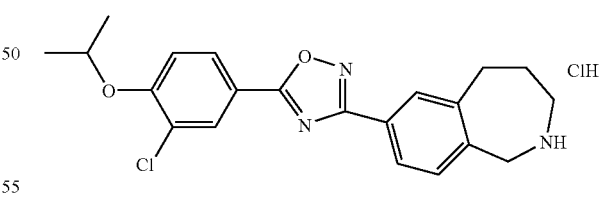

1,1-Dimethylethyl 7-(5-{3-chloro-4-[(1-methylethyl)oxy]phenyl}-1,2,4-oxadiazol-3-yl)-1,3,4,5-tetrahydro-2H-2-benzazepine-2-carboxylate (Preparation 7) (75 mg, 0.155 mmol) was treated with 4N HCl in dioxan (1162 μl, 4.65 mmol) and the clear solution left standing for 1.5 hours. A white precipitate formed. Ether (1 ml) was added and the white solid was filtered off, washing with ether. The title compound was obtained on drying of the solid (45 mg). δH (400 MHz, d_6DMSO) 1.36 (6H, d), 1.91-1.98 (2H, m), 3.11-3.14 (2H, m), 3.36-3.39 (2H, m), 4.41 (2H, s), 4.85-4.94 (1H, m), 7.46 (1H, d), 7.64 (1H, d), 7.95-7.80 (2H, m), 8.11 (1H, dd), 8.19 (1H, d), 9.04 (2H, broad s); MS (ES) $C_{21}H_{22}{}^{35}ClN_3O_2$ requires 383; found 384.0 $[M+H]^+$.

EXAMPLE 2

[7-(5-{3-Chloro-4-[(1-methylethyl)oxy]phenyl}-1,2,4-oxadiazol-3-yl)-1,3,4,5-tetrahydro-2H-2-benzazepin-2-yl]acetic acid

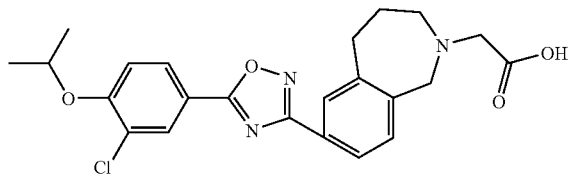

1,1-Dimethylethyl [7-(5-{3-chloro-4-[(1-methylethyl)oxy]phenyl}-1,2,4-oxadiazol-3-yl)-1,3,4,5-tetrahydro-2H-2-benzazepin-2-yl]acetate (Preparation 8) (65 mg, 0.131 mmol) was treated with HCl (1305 µl, 5.22 mmol) (4N in dioxan) and left standing for 2 hours. The reaction mixture was then warmed at 50° C. for 1 hour then heated at 60° C. for a further 1.25 hours before solvent removal by evaporation. Trituration with ether/EtOAc failed and the material obtained was purified by MDAP. A white solid (20 mg) was obtained freeze drying appropriate MDAP fractions. Further drying under vacuum at 70° C. for 16 hours yielded the title compound (16 mg) as a solid. δH (400 MHz, d$_6$DMSO) 1.36 (6H, d), 1.51-1.53 (2H, m), 2.98-3.00 (2H, m), 3.4 (2H, br.s), 4.10 (2H, s), 4.86-4.92 (1H, m), 7.32 (1H, d), 7.44 (1H, d), 7.83-7.88 (2H, m), 8.11 (1H, dd), 8.18 (1H, d); MS (ES) $C_{23}H_{24}{}^{35}ClN_3O_4$ requires 441; found 442 $[M+H]^+$.

EXAMPLE 3

2-[(1-Methylethyl)oxy]-5-[3-(2,3,4,5-tetrahydro-1H-2-benzazepin-7-yl)-1,2,4-oxadiazol-5-yl]benzonitrile hydrochloride

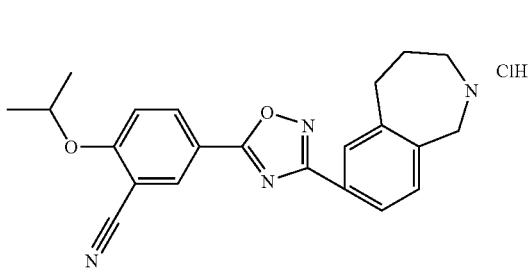

1,1-Dimethylethyl 7-(5-{3-cyano-4-[(1-methylethyl)oxy]phenyl}-1,2,4-oxadiazol-3-yl)-1,3,4,5-tetrahydro-2H-2-benzazepine-2-carboxylate (Preparation 9) (310 mg, 0.653 mmol) was treated with HCl (3266 µl, 13.06 mmol) (4N in dioxan) and stirred. After 30 minutes a white precipitate had formed. After 1 hour ether (2 ml) was added and the precipitate filtered off and washed with ether. The title compound (230 mg) was obtained on drying. δH (400 MHz, d$_6$DMSO) 1.39 (6H, d), 1.91 (2H, m), 3.11-3.13 (2H, m), 3.37-3.40 (2H, m), 4.42 (2H, s), 4.94-5.02 (1H, m), 7.57 (1H, d), 7.64 (1H, d), 7.96-8.00 (2H, m), 8.41 (1H, dd), 8.52 (1H, d), 9.04 (2H, broad s); MS (ES) $C_{22}H_{22}N_4O_2$ requires 374; found 375.0 $[M+H]^+$.

EXAMPLE 4

[7-(5-{3-Cyano-4-[(1-methylethyl)oxy]phenyl}-1,2,4-oxadiazol-3-yl)-1,3,4,5-tetrahydro-2H-2-benzazepin-2-yl]acetic acid

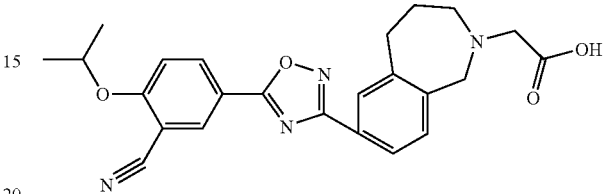

1,1-Dimethylethyl [7-(5-{3-cyano-4-[(1-methylethyl)oxy]phenyl}-1,2,4-oxadiazol-3-yl)-1,3,4,5-tetrahydro-2H-2-benzazepin-2-yl]acetate (Preparation 10) (85 mg, 0.174 mmol) was treated with HCl (1305 µl, 5.22 mmol) (4N soln in dioxan) and warmed at 50° C. for 2 hours. A white crystalline product formed. The reaction was cooled to RT and the solid filtered off and washed with ether. On drying the title compound was obtained (65 mg) as a white solid. δH (400 MHz, d$_6$DMSO) 1.39 (6H, d), 1.91-2.00 (2H, m), 3.11-3.12 (2H, m), 3.59 (2H, m), 4.00 (2H, s), 4.60 (2H, s), 4.94-5.02 (1H, m), 7.53-7.59 (2H, m), 7.99-8.06 (2H, m), 8.41 (1H, dd), 8.52 (1H, d); MS (ES) $C_{24}H_{24}N_4O_4$ requires 432; found 433 $[M+H]^+$.

EXAMPLE 5

4-[7-(5-{3-Cyano-4-[(1-methylethyl)oxy]phenyl}-1,2,4-oxadiazol-3-yl)-1,3,4,5-tetrahydro-2H-2-benzazepin-2-yl]butanoic acid acetate

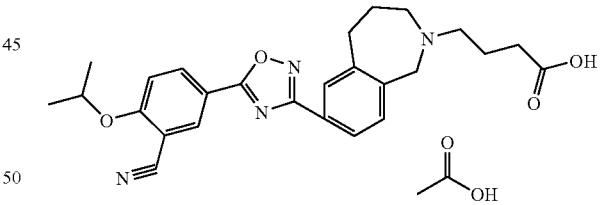

Ethyl 4-[7-(5-{3-cyano-4-[(1-methylethyl)oxy]phenyl}-1,2,4-oxadiazol-3-yl)-1,3,4,5-tetrahydro-2H-2-benzazepin-2-yl]butanoate (preparation 11) (90 mg, 0.184 mmol) dissolved in ethanol (20 ml) was treated with sodium hydroxide (0.184 ml, 0.368 mmol) (2N (aq)) solution followed by water (5.00 ml). This mixture was stirred at RT for 3 hours and left standing overnight. 2N NaOH (aq) (150 pl) was added and the reaction mixture stirred for 3 hours. Then ethanol was removed by evaporation and the aqueous layer acidified using AcOH. The product was extracted into EtOAc (50 ml) and dried over MgSO$_4$. Solvent removal by evaporation yielded a white precipitate. Ether was added and the solid filtered off and washed with ether to yield the title compound (44 mg) on drying. δH (400 MHz, d$_6$DMSO) 1.39 (6H, d), 1.91-1.95 (4H, m), 2.30 (2H, t), 2.96 (2H, m), 3.13 (2H, m), 3.53 (2H, m), 4.60 (2H, s), 4.94-5.03 (1H, m), 7.57 (1H, d), 7.68 (1H, d), 7.97-8.00 (2H, m), 8.41 (1H, dd), 8.52 (1H, d) 10.6 (1H, v. broad s), 12.3 (1H, v. broad s); MS (ES) $C_{26}H_{28}N_4O_4$ requires 460; found 461.0 $[M+H]^+$.

EXAMPLE 6

3-[7-(5-{3-Cyano-4-[(1-methylethyl)oxy]phenyl}-1,2,4-oxadiazol-3-yl)-1,3,4,5-tetrahydro-2H-2-benzazepin-2-yl]propanoic acid hydrochloride

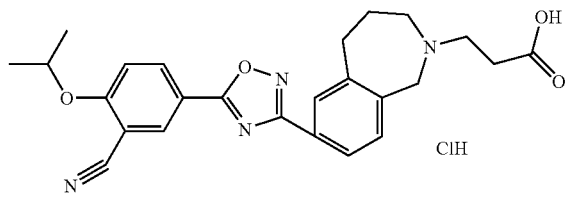

1,1-Dimethylethyl 3-[7-(5-{3-cyano-4-[(1-methylethyl)oxy]phenyl}-1,2,4-oxadiazol-3-yl)-1,3,4,5-tetrahydro-2H-2-benzazepin-2-yl]propanoate (Preparation 12) (70 mg, 0.139 mmol) was treated with HCl (1045 µl, 4.18 mmol) (4N in dioxan) and warmed at 50° C. for 1.5 hours. A white precipitate started to form. Ether (0.5 ml) was added and the white solid filtered off and washed with ether to give the title compound (57 mg) on drying. δH (400 MHz, d$_6$DMSO) 1.39 (6H, d), 1.91-1.96 (2H, m), 2.82 (2H, m), 3.12-3.21 (4H, m), 3.56 (2H, m), 4.62 (2H, s), 4.96-5.02 (1H, m), 7.57 (1H, d), 7.71 (1H, d), 7.99-8.01 (2H, m), 8.41 (1H, dd), 8.52 (1H, d), 10.3 (1H, v. broad s), 12.8 (1H, v. broad s); MS (ES) $C_{25}H_{26}N_4O_4$ requires 446; found 447.0 $[M+H]^+$.

EXAMPLE 7

2-[(1-Methylethyl)oxy]-5-[3-(2,3,4,5-tetrahydro-1H-3-benzazepin-6-yl)-1,2,4-oxadiazol-5-yl]benzonitrile hydrochloride

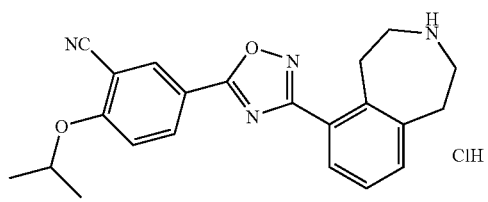

1,1-Dimethylethyl 6-(5-{3-cyano-4-[(1-methylethyl)oxy]phenyl}-1,2,4-oxadiazol-3-yl)-1,2,4,5-tetrahydro-3H-3-benzazepine-3-carboxylate (Preparation 16) (505 mg, 1.064 mmol) was dissolved in DCM (40 ml) and treated with trifluoroacetic acid (4 ml, 51.9 mmol). The resulting mixture was heated at reflux for 1 hour then evaporated. The resulting residue was partitioned between DCM (20 ml) and 2N NaOH (20 ml). The DCM layer was collected, dried (hydrophobic frit) and evaporated. The free-base was dissolved in 4M HCl in dioxane and evaporated to give the HCl salt, 2-[(1-methylethyl)oxy]-5-[3-(2,3,4,5-tetrahydro-1H-3-benzazepin-6-yl)-1,2,4-oxadiazol-5-yl]benzonitrile hydrochloride (438 mg, 1.066 mmol, 100% yield) as an off-white powder. δH (400 MHz, CDCl$_3$) 10.15 (1H, br.s), 8.39 (1H, s), 8.33-8.31 (1H, m), 7.75-7.85 (1H, m), 7.45-7.3 (2H, m), 7.14 (1H, d), 4.84-4.76 (1H, m), 3.90-3.30 (8H, m) 1.48 (6H, d); MS (ES) $C_{22}H_{22}N_4O_2$ requires 374; found 375 $[M+H]^+$.

EXAMPLE 8

6-(5-{3-Chloro-4-[(1-methylethyl)oxy]phenyl}-1,2,4-oxadiazol-3-yl)-2,3,4,5-tetrahydro-1H-3-benzazepine hydrochloride

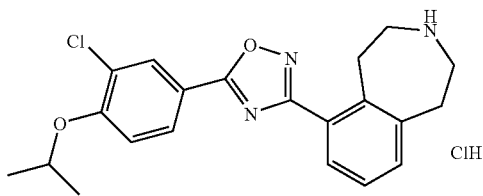

1,1-Dimethylethyl 6-(5-{3-chloro-4-[(1-methylethyl)oxy]phenyl}-1,2,4-oxadiazol-3-yl)-1,2,4,5-tetrahydro-3H-3-benzazepine-3-carboxylate (Preparation 17) (260 mg, 0.537 mmol) was dissolved in DCM (20 ml) and treated with trifluoroacetic acid (2 ml, 26.0 mmol). The resulting mixture was heated at reflux for 1 hour then evaporated. The resulting residue was partitioned between DCM (10 ml) and 2N NaOH (10 ml). The DCM layer was collected, dried (hydrophobic frit) and evaporated. The free-base was dissolved in 4M HCl in dioxane and evaporated to give the HCl salt, 6-(5-{3-chloro-4-[(1-methylethyl)oxy]phenyl}-1,2,4-oxadiazol-3-yl)-2,3,4,5-tetrahydro-1H-3-benzazepine hydrochloride (225 mg, 0.535 mmol, 100% yield) as an off-white powder. δH (400 MHz, CDCl$_3$) 10.10 (2H, br.s), 8.18 (1H, s), 8.02 (1H, d), 7.82-7.80 (1H, m), 7.33-7.22 (2H, m), 7.05 (1H, d), 5.30 (2H, s), 4.76-4.64 (1H, m), 3.8-3.65 (2H, m), 3.48-3.3 (4H, m), 1.45 (6H, d); MS (ES) $C_{21}H_{22}{}^{35}ClN_3O_2$ requires 383; found 384 $[M+H]^+$.

EXAMPLE 9

3-[6-(5-{3-Chloro-4-[(1-methylethyl)oxy]phenyl}-1,2,4-oxadiazol-3-yl)-1,2,4,5-tetrahydro-3H-3-benzazepin-3-yl]propanoic acid hydrochloride

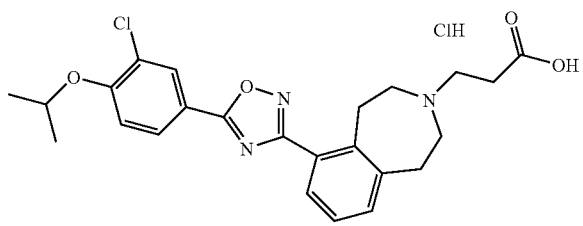

1,1-Dimethylethyl 3-[6-(5-{3-chloro-4-[(1-methylethyl)oxy]phenyl}-1,2,4-oxadiazol-3-yl)-1,2,4,5-tetrahydro-3H-3-benzazepin-3-yl]propanoate (Preparation 18) (25 mg, 0.049 mmol) was stirred at room temperature for 18 hours in 4M HCl in 1,4-dioxane (10 ml). Evaporation and trituration with diethylether yielded the title compound 3-[6-(5-{3-chloro-4-[(1-methylethyl)oxy]phenyl}-1,2,4-oxadiazol-3-yl)-1,2,4,5-tetrahydro-3H-3-benzazepin-3-yl]propanoic acid hydrochloride (13 mg, 0.026 mmol, 54.1% yield) as a yellow gum. MS (ES) $C_{24}H_{26}{}^{35}ClN_3O_4$ requires 455; found 456 $[M+H]^+$.

EXAMPLE 10

[6-(5-{3-Chloro-4-[(1-methylethyl)oxy]phenyl}-1,2,4-oxadiazol-3-yl)-1,2,4,5-tetrahydro-3H-3-benzazepin-3-yl]acetic acid hydrochloride

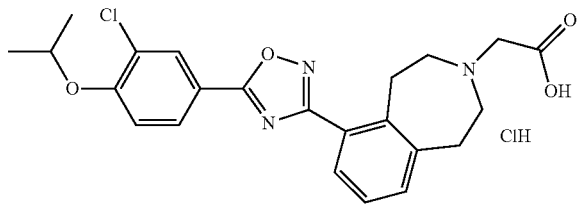

1,1-Dimethylethyl [6-(5-{3-chloro-4-[(1-methylethyl)oxy]phenyl}-1,2,4-oxadiazol-3-yl)-1,2,4,5-tetrahydro-3H-3-benzazepin-3-yl]acetate (Preparation 19) (120 mg, 0.241 mmol) was stirred at room temperature for 18 hours in 4M HCl in 1,4-dioxane (20 ml). Evaporation and trituration with diethylether yielded the HCl salt [6-(5-{3-chloro-4-[(1-methylethyl)oxy]phenyl}-1,2,4-oxadiazol-3-yl)-1,2,4,5-tetrahydro-3H-3-benzazepin-3-yl]acetic acid hydrochloride (110 mg, 0.216 mmol, 90% yield) as a cream powder. MS (ES) $C_{23}H_{24}{}^{35}ClN_3O_4$ requires 441; found 442 $[M+H]^+$.

EXAMPLE 11

6-(5-{3-Chloro-4-[(1-methylethyl)oxy]phenyl}-1,2,4-oxadiazol-3-yl)-2,3,4,5-tetrahydro-1H-2-benzazepine

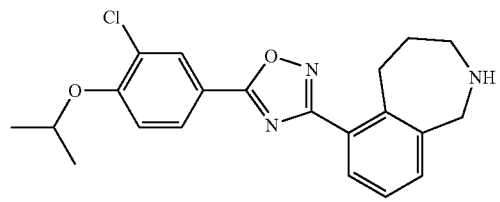

To a solution of 3-[2-(aminomethyl)-6-(5-{3-chloro-4-[(1-methylethyl)oxy]phenyl}-1,2,4-oxadiazol-3-yl)phenyl]-1-propanol (Preparation 23) (105.2 mg, 0.262 mmol) and triphenylphosphine (343 mg, 1.309 mmol) in dry DCM (40 ml) at RT under Ar was added DIAD (0.242 ml, 1.243 mmol) dropwise and the resulting pale yellow solution stirred at RT for 18 hrs. The solution was concentrated to ~5 ml, then passed down an SCX-3 cartridge (1 g), washing with MeOH. The product was eluted with 0.5M $NH_3$ in MeOH; concentration in vacuo gave a pale yellow oil (95.7 mg). Reverse-phase mass-directed auto-purification gave two fractions containing the desired product, one of which was contaminated with O=PPh$_3$. Both were added directly to an SCX-2 cartridge (10 g), washing with MeOH. The product was eluted with 0.5M $NH_3$ in MeOH; concentration in vacuo gave a pale yellow film 6-(5-{3-chloro-4-[(1-methylethyl)oxy]phenyl}-1,2,4-oxadiazol-3-yl)-2,3,4,5-tetrahydro-1H-2-benzazepine (15.3 mg, 0.034 mmol, 12.94% yield). δH (400 MHz, CDCl$_3$) 8.20 (1H, d), 8.04 (1H, dd), 7.69 (1H, d), 7.31 (1H, d), 7.24 (1H, t), 7.05 (1H, d), 4.71 (1H, sept), 4.09 (2H, s), 3.30-3.24 (4H, m), 1.80 (2H, m), 1.44 (6H, d); MS (ES) $C_{21}H_{22}{}^{35}ClN_3O_2$ requires 383; found 384 $[M+H]^+$.

EXAMPLE 12

[6-(5-{3-Chloro-4-[(1-methylethyl)oxy]phenyl}-1,2,4-oxadiazol-3-yl)-1,3,4,5-tetrahydro-2H-2-benzazepin-2-yl]acetic acid hydrochloride

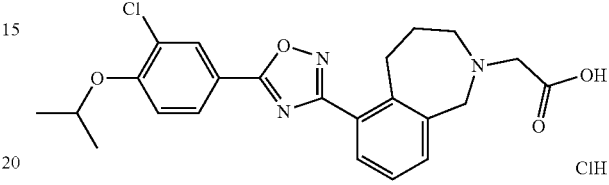

A 5:2 mixture of 1,1-dimethylethyl [6-(5-{3-chloro-4-[(1-methylethyl)oxy]phenyl}-1,2,4-oxadiazol-3-yl)-1,3,4,5-tetrahydro-2H-2-benzazepin-2-yl]acetate and [6-(5-{3-chloro-4-[(1-methylethyl)oxy]phenyl}-1,2,4-oxadiazol-3-yl)-1,3,4,5-tetrahydro-2H-2-benzazepin-2-yl]acetic acid (Preparation 24) (21.4 mg) in 4M HCl in dioxane (3 ml) was stirred at RT for 21 hours. The reaction mixture was concentrated in vacuo, then redissolved in 4M HCl in dioxane (3 ml), and the solution stirred for an additional 24 hours. Concentration in vacuo gave a yellow oil (41 mg), that was triturated with ether (2×3 ml) to leave a white solid [6-(5-{3-chloro-4-[(1-methylethyl)oxy]phenyl}-1,2,4-oxadiazol-3-yl)-1,3,4,5-tetrahydro-2H-2-benzazepin-2-yl]acetic acid hydrochloride (16.1 mg, 0.031 mmol, 90% yield). δH (400 MHz, d$_6$DMSO) 8.17 (1H, d), 8.10 (1H, dd), 7.87 (1H, dd), 7.58 (1H, d), 7.49 (1H, t), 7.46 (1H, d), 4.89 (1H, sept), 4.69 (2H, s), 4.06 (2H, s), 3.58 (2H, br t), 3.35 (2H, m), 2.00 (2H, br s), 1.36 (6H, d); MS (ES) $C_{23}H_{24}{}^{35}ClN_3O_4$ requires 441; found 442 $[M+H]^+$.

EXAMPLE 13

8-(5-{3-Chloro-4-[(1-methylethyl)oxy]phenyl}-1,2,4-oxadiazol-3-yl)-2,3,4,5-tetrahydro-1,4-benzoxazepine hydrochloride

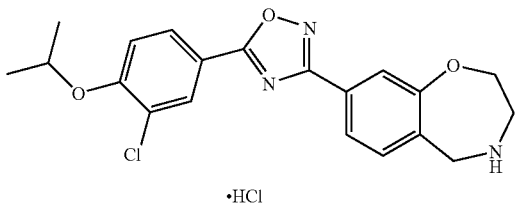

1,1-Dimethylethyl 8-(5-{3-chloro-4-[(1-methylethyl)oxy]phenyl}-1,2,4-oxadiazol-3-yl)-2,3-dihydro-1,4-benzoxazepine-4(5H)-carboxylate (Preparation 34) (0.171 g, 0.352 mmol) was dissolved in 1,4-dioxane (1 ml) and 4M HCl (4 ml, 16.00 mmol) in dioxane was added. The reaction mixture was left at room temperature for 3 hours. The resulting precipitated solid was filtered off and washed with dioxane and ether to give the title compound (116 mgs) as a white solid hydrochloride salt. δH (400 MHz, MeOD) 1.42 (6H, d), 3.64

(2H, m), 4.34 (2H, m), 4.48 (2H, s), 4.86 (1H, m), 7.31 (1H, d), 7.59 (1H, d), 7.87 (1H, d), 7.94 (1H, dd), 8.11 (1H, dd), 8.21 (1H, dd); MS (ES) $C_{20}H_{20}{}^{35}ClN_3O_3$ requires 385; found 486 [M+H]$^+$.

EXAMPLE 14

3-[8-(5-{3-Chloro-4-[(1-methylethyl)oxy]phenyl}-1,2,4-oxadiazol-3-yl)-2,3-dihydro-1,4-benzoxazepin-4(5H)-yl]propanoic acid hydrochloride

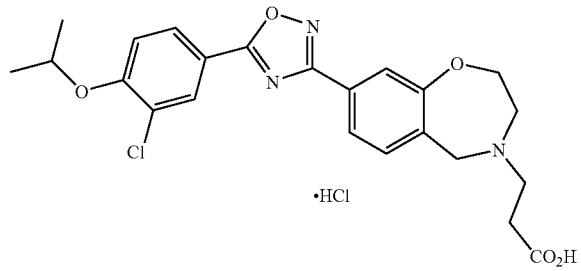

2M Sodium hydroxide solution (aq) (0.5 ml, 1.000 mmol) was added to a solution of ethyl 3-[8-(5-{3-chloro-4-[(1-methylethyl)oxy]phenyl}-1,2,4-oxadiazol-3-yl)-2,3-dihydro-1,4-benzoxazepin-4(5H)-yl]propanoate (Preparation 35) (0.09 g, 0.185 mmol) in ethanol (4 ml) and left at room temperature for 2 hours. The reaction was then evaporated and the resulting crude dissolved in EtOAc/water (30 ml of each) and acidified with acetic acid. The organic layer was dried (magnesium sulphate) and evaporated. The resulting crude was azeotroped with 20 ml of toluene and the residue dissolved in 10 ml of DCM. 1M HCl (1 ml) in ether was added, the reaction mixture evaporated then triturated with ether. The title compound (56 mg) was filtered off as an off-white solid hydrochloride salt. δH (400 MHz, MeOD) 1.42 (6H, d), 2.92 (2H, t), 3.55 (2H, t), 3.78 (2H, m), 4.40 (2H, m), 4.65 (2H, s), 4.87 (1H, m), 7.31 (1H, d), 7.61 (1H, d), 7.87 (1H, d), 7.96 (1H, dd), 8.11 (1H, dd), 8.21 (1H, d); MS (ES) $C_{23}H_{24}{}^{35}ClN_3O_6$ requires 457; found 458 [M+H]$^+$.

EXAMPLE 15

4-[8-(5-{3-Chloro-4-[(1-methylethyl)oxy]phenyl}-1,2,4-oxadiazol-3-yl)-2,3-dihydro-1,4-benzoxazepin-4(5H)-yl]butanoic acid

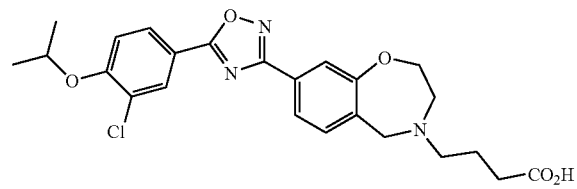

2M Sodium hydroxide (aq) (0.5 ml, 1.000 mmol) was added to a solution of ethyl 4-[8-(5-{3-chloro-4-[(1-methylethyl)oxy]phenyl}-1,2,4-oxadiazol-3-yl)-2,3-dihydro-1,4-benzoxazepin-4(5H)-yl]butanoate (Preparation 36) (0.103 g, 0.206 mmol) in ethanol (4 ml) and left at room temperature for 2 hours. The reaction mixture was evaporated and the residue dissolved in water/EtOAc (30 ml of each) and acidified with acetic acid. The organic layer was collected, dried (magnesium sulphate), evaporated and azeotroped with 15 ml of toluene. The title compound was obtained by triturating with ether and filtering off as a white solid (65 mg). δH (400 MHz, d$_6$DMSO) 1.36 (6H, d), 1.70 (2H, m), 2.23 (2H, t), 2.33 (2H, t), 3.02 (2H, m), 3.84 (2H, s), 4.06 (2H, m), 4.89 (1H, m), 7.44 (2H, m), 7.61 (1H, d), 7.72 (1H, dd), 8.10 (1H, dd), 8.18 (1H, d); MS (ES) $C_{24}H_{26}{}^{35}ClN_3O_5$ requires 471; found 472 [M+H]$^+$.

EXAMPLE 16

[8-(5-{3-Chloro-4-[(1-methylethyl)oxy]phenyl}-1,2,4-oxadiazol-3-yl)-2,3-dihydro-1,4-benzoxazepin-4(5H)-yl]acetic acid

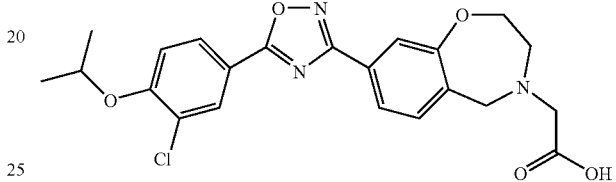

1,1-Dimethylethyl [8-(5-{3-chloro-4-[(1-methylethyl)oxy]phenyl}-1,2,4-oxadiazol-3-yl)-2,3-dihydro-1,4-benzoxazepin-4(5H)-yl]acetate (Preparation 37) (0.13 g, 0.260 mmol) was dissolved in 1,4-dioxane (1 ml) and 4M HCl (4 ml, 16.00 mmol) in dioxan was added and the reaction mixture was left at room temperature for 24 hours. Then the reaction mixture was evaporated, triturated with ether and the resulting solid filtered off. The solid was dissolved in 5 ml of 2M sodium hydroxide and acidified with acetic acid when solid separated. Attempted to dissolve in EtOAc but insoluble so filtered off and washed well with water, acetone and ether to give the title compound (44 mgs) as a white solid. δH (400 MHz, d$_6$DMSO) 1.36 (6H, d), 3.13 (2H, br. s), 3.96 (2H, s), 4.08 (2H, br. s), 4.89 (1H, m), 7.38 (1H, d), 7.44 (1H, d), 7.61 (1H, s), 7.72 (1H, d), 8.11 (1H, d), 8.18 (1H, d), (remaining 2H signal obscured by solvent peak); MS (ES) $C_{22}H_{22}{}^{35}ClN_3O_5$ requires 443; found 444 [M+H]$^+$.

EXAMPLE 17

7-(5-{3-Chloro-4-[(1-methylethyl)oxy]phenyl}-1,2,4-oxadiazol-3-yl)-2,3,4,5-tetrahydro-1H-3-benzazepine hydrochloride

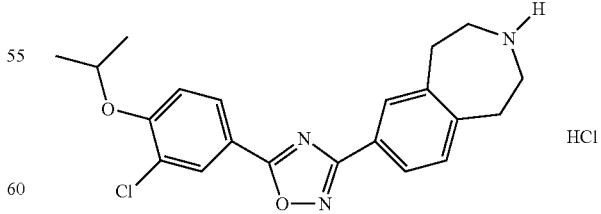

A solution of 1,1-dimethylethyl 7-(5-{3-chloro-4-[(1-methylethyl)oxy]phenyl}-1,2,4-oxadiazol-3-yl)-1,2,4,5-tetrahydro-3H-3-benzazepine-3-carboxylate (Preparation 42) (950 mg, 1.963 mmol) in hydrochloric acid (a 4M solution in dioxane, 10 ml, 40.0 mmol) and 1,4-dioxane (10 ml) was stirred at room temperature for 5 hours (a precipitate had formed). The reaction mixture was filtered and washed with dioxane (~5 ml), and the solid dried under vacuum (pistol) overnight to yield the title compound (711 mg, 1.607 mmol, 82% yield) as a white solid. δH (CDCl$_3$, 400 MHz): 10.17 (2H, br s), 8.25 (1H, d), 8.06 (1H, dd), 7.98-8.03 (2H, m), 7.33 (1H, d), 7.06 (1H, d), 4.72 (1H, sept), 3.35-3.47 (8H, m), 1.46 (6H, d). MS (ES): C$_{21}$H$_{22}$$^{35}$ClN$_3$O$_2$ requires 383; found 384 [M+H]$^+$.

EXAMPLE 18

2-[(1-Methylethyl)oxy]-5-[3-(2,3,4,5-tetrahydro-1H-3-benzazepin-7-yl)-1,2,4-oxadiazol-5-yl]benzonitrile hydrochloride

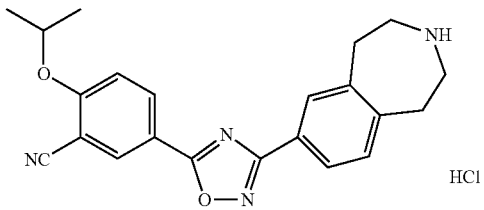

1,1-Dimethylethyl-7-(5-{3-cyano-4-[(1-methylethyl)oxy] phenyl}-1,2,4-oxadiazol-3-yl)-1,2,4,5-tetrahydro-3H-3-benzazepine-3-carboxylate (Preparation 43) (735 mg, 1.55 mmol) was dissolved in 4M HCl in dioxane and the solution stirred for 1 h. The title compound was filtered off as a white solid and dried in a vacuum oven (462 mg, 1.13 mmol). δH (d$_6$DMSO, 400 MHz): 9.24 (2H, brs), 8.51 (1H, d), 8.40 (1H, dd), 7.95 (1H, d), 7.92 (1H, dd), 7.57 (1H, d), 7.45 (1H, d), 4.98 (1H, septet), 3.28-3.18 (8H, m), 1.39 (6H, d). MS (ES): C$_{22}$H$_{22}$N$_4$O$_2$ requires 374; found 375 [M+H]$^+$.

EXAMPLE 19

7-{5-[4-[(1-Methylethyl)oxy]-3-(trifluoromethyl) phenyl]-1,2,4-oxadiazol-3-yl}-2,3,4,5-tetrahydro-1H-3-benzazepine hydrochloride

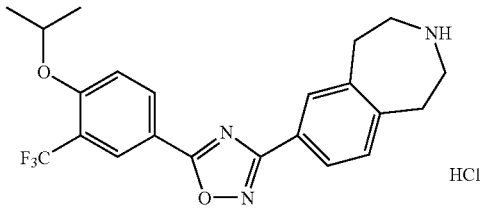

1,1-Dimethylethyl-7-{5-[4-[(1-methylethyl)oxy]-3-(trifluoromethyl)phenyl]-1,2,4-oxadiazol-3-yl}-1,2,4,5-tetrahydro-3H-3-benzazepine-3-carboxylate (Preparation 44) (550 mg, 1.06 mmol) was dissolved in 4M HCl in dioxane (5 ml) and the solution stirred for 2 h. The title compound was filtered off as a white solid and dried in a vacuum oven (259 mg, 0.57 mmol). δH (d$_6$DMSO, 400 MHz): 9.23 (2H, brs), 8.40 (1H, dd), 8.31 (1H, d), 7.96 (1H, d), 7.93 (1H, dd), 7.59 (1H, d), 7.44 (1H, d), 4.98 (1H, septet), 3.27-3.18 (8H, m), 1.36 (6H, d); MS (ES): C$_{22}$H$_{22}$F$_3$N$_3$O$_2$ requires 417; found 418 [M+H]$^+$.

EXAMPLE 20

7-{5-[2-(Trifluoromethyl)-4-biphenylyl]-1,2,4-oxadiazol-3-yl}-2,3,4,5-tetrahydro-1H-3-benzazepine hydrochloride

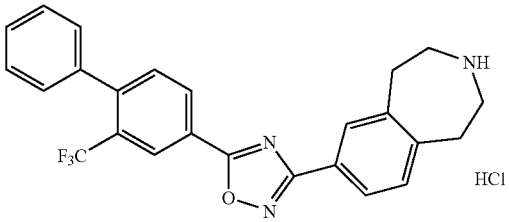

1,1-Dimethylethyl-7-{5-[2-(trifluoromethyl)-4-biphenylyl]-1,2,4-oxadiazol-3-yl}-1,2,4,5-tetrahydro-3H-3-benzazepine-3-carboxylate (Preparation 45) (440 mg, 0.82 mmol) was dissolved in 4M HCl in dioxane (3 ml) and the solution stirred for 2 h. The title compound was filtered off as a white solid (376 mg, 0.82 mmol). δH (d$_6$DMSO, 400 MHz): 9.27 (2H, brs), 8.53 (1H, d), 8.51 (1H, dd), 8.01 (1H, d), 7.97 (1H, dd), 7.74 (1H, d), 7.54-7.50 (3H, m), 7.47 (1H, d), 7.43-7.39 (2H, m), 3.28-3.20 (8H, m). MS (ES): C$_{25}$H$_{20}$F$_3$N$_3$O requires 435; found 436 [M+H]$^+$.

EXAMPLE 21

3-[7-(5-{3-Chloro-4-[(1-methylethyl)oxy]phenyl}-1,2,4-oxadiazol-3-yl)-1,2,4,5-tetrahydro-3H-3-benzazepin-3-yl]propanoic acid

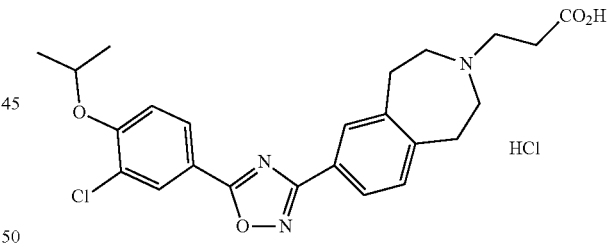

A mixture of 7-(5-{3-chloro-4-[(1-methylethyl)oxy]phenyl}-1,2,4-oxadiazol-3-yl)-2,3,4,5-tetrahydro-1H-3-benzazepine hydrochloride (Example 17) (200 mg, 0.52 mmol), 1,1-dimethylethyl 2-propenoate (151 μL, 1.04 mmol) and diisopropylethylamine (453 μL, 2.60 mmol) in methanol (5 ml) was heated in the microwave at 90° C. for 30 minutes before the solvent was removed in vacuo. The residue was dissolved in 4M HCl (2 ml) in dioxane and the mixture stirred at room temperature for 5 h. The solvent was removed in vacuo and the residue purified by MDAP. To the product containing fractions was added 2M HCl and the solution concentrated in vacuo to give the title compound as a white solid (116 mg, 0.24 mmol). δH (d$_6$DMSO, 400 MHz): 12.73 (1H, br.s), 10.76 (1H, br.s), 8.19 (1H, d), 8.11 (1H, dd), 7.98 (1H, d), 7.93 (1H, dd), 7.46 (1H, d), 7.45 (1H, d), 4.89 (1H, septet), 3.76-3.64 (2H, m), 3.44-3.31 (4H, hidden under H$_2$O peak), 3.25-3.03 (4H, m), 2.89 (2H, t), 1.37 (6H, d). MS (ES): $C_{24}H_{26}{}^{35}ClN_3O_4$ requires 455; found 456 [M+H]⁺.

EXAMPLE 22

[7-(5-{3-Chloro-4-[(1-methylethyl)oxy]phenyl}-1,2,4-oxadiazol-3-yl)-1,2,4,5-tetrahydro-3H-3-benzazepin-3-yl]acetic acid

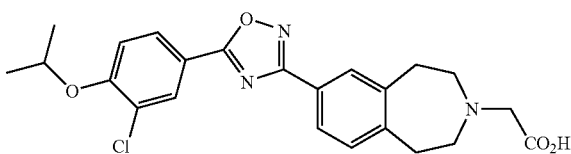

A solution of ethyl [7-(5-{3-chloro-4-[(1-methylethyl)oxy]phenyl}-1,2,4-oxadiazol-3-yl)-1,2,4,5-tetrahydro-3H-3-benzazepin-3-yl]acetate (Preparation 46) (77 mg, 0.164 mmol) in methanol (30 ml) was stirred at room temp and sodium hydroxide (3 ml, 6.00 mmol) added. The reaction mixture was stirred at room temperature overnight. The solvent was removed in vacuo, the solid was triturated with methanol (~5 ml) and the resultant solid filtered off and dried. The solid was suspended in methanol (~30 ml) and acetic acid added to take the pH of the solution to 5-6, the solvent was removed in vacuo. The resultant residue was dissolved in DCM (~30 ml) and water (~30 ml) and the layers partitioned. The aqueous was re-extracted with DCM (~20 ml) and the combined organics were passed through a phase separation cartridge and the solvent reduced in vacuo. The resultant residue was dried in a drying pistol at 60° C. to yield the title compound (22 mg, 0.047 mmol, 29% yield) as an off white solid. δH (d₆DMSO, 400 MHz): 8.19 (1H, s), 8.11 (1H, d), 7.82-7.90 (2H, m), 7.44 (1H, d), 7.36 (1H, d), 4.89 (1H, sept), 3.34 (2H, s), 3.07-2.98 (4H, m), 2.91-2.86 (4H, m), 1.37 (6H, d. MS (ES⁺): $C_{23}H_{24}{}^{35}ClN_3O_4$ requires 441; found 442 [M+H]⁺.

EXAMPLE 23

[7-(5-{3-Cyano-4-[(1-methylethyl)oxy]phenyl}-1,2,4-oxadiazol-3-yl)-1,2,4,5-tetrahydro-3H-3-benzazepin-3-yl]acetic acid

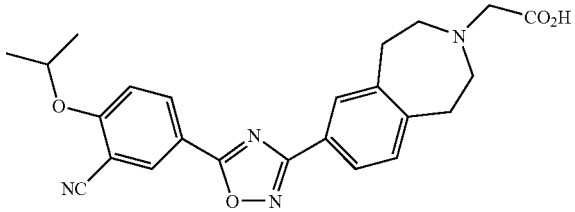

A mixture of ethyl [7-(5-{3-cyano-4-[(1-methylethyl)oxy]phenyl}-1,2,4-oxadiazol-3-yl)-1,2,4,5-tetrahydro-3H-3-benzazepin-3-yl]acetate (Preparation 47) (43 mg, 0.09 mmol), aqueous sodium hydroxide (2M, 430 μL, 0.86 mmol) and ethanol (4.3 ml) was heated at 40° C. for 1 h. The reaction mixture was cooled to room temperature and concentrated. The residue was taken up in water, which was then acidified to pH 6 with acetic acid. The aqueous phase was extracted with EtOAc (2×20 ml) and the combined organic fractions concentrated to give a white solid, which was then triturated with EtOAc to give the title compound as a white solid (36 mg, 0.08 mmol). δH (d₆DMSO, 400 MHz): 8.50 (1H, d), 8.41 (1H, dd), 7.85-7.80 (2H, m), 7.55 (1H, d), 7.32 (1H, d), 4.98 (1H, septet), 3.00-2.91 (6H, m), 2.75-2.66 (4H, m), 1.39 (6H, d); MS (ES−): $C_{24}H_{24}N_4O_4$ requires 432; found 431 [M−H]⁺.

EXAMPLE 24

(7-{5-[4-[(1-Methylethyl)oxy]-3-(trifluoromethyl) phenyl]-1,2,4-oxadiazol-3-yl}-1,2,4,5-tetrahydro-3H-3-benzazepin-3-yl)acetic acid

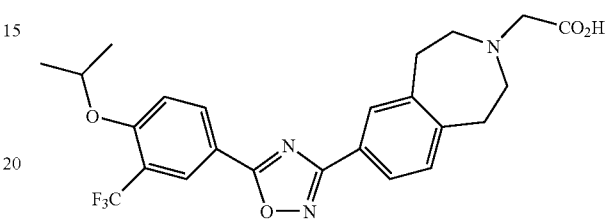

A mixture of ethyl (7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)acetate (Preparation 48) (59 mg, 0.12 mmol), aqueous sodium hydroxide (2M, 590 μL, 1.18 mmol) and ethanol (6 ml) was heated at 40° C. for 1 hr. The reaction mixture was cooled to room temperature and concentrated. The residue was taken up in water, which was then acidified to pH 6 with acetic acid. The aqueous phase was extracted with EtOAc (2×20 ml) before the combined organic fractions were concentrated and the residue was triturated with EtOAc and the title compound was filtered off and dried in a vacuum oven to give a white solid (36 mg, 0.08 mmol). δH (d₆DMSO, 400 MHz): 8.41 (1H, dd), 8.30 (1H, d), 7.88-7.82 (2H, m), 7.58 (1H, d), 7.35 (1H, d), 4.98 (1H, septet), 3.25 (2H, s), 3.06-2.96 (4H, m), 2.89-2.81 (4H, m), 1.36 (6H, d); MS (ES−): $C_{24}H_{24}F_3N_3O_4$ requires 475; found 474 [M−H⁺].

EXAMPLE 25

(7-{5-[2-(Trifluoromethyl)-4-biphenylyl]-1,2,4-oxadiazol-3-yl}-1,2,4,5-tetrahydro-3H-3-benzazepin-3-yl)acetic acid

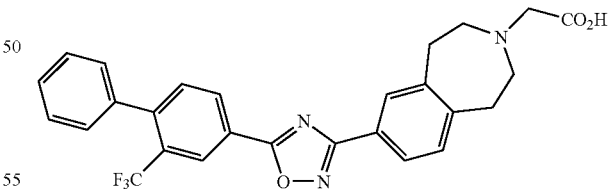

A mixture of ethyl (7-{5-[2-(trifluoromethyl)-4-biphenylyl]-1,2,4-oxadiazol-3-yl}-1,2,4,5-tetrahydro-3H-3-benzazepin-3-yl)acetate (Preparation 49) (22 mg, 0.04 mmol), aqueous sodium hydroxide (2M, 220 μL, 0.44 mmol) and ethanol (2.2 ml) was heated at 40° C. for 1 h. The reaction mixture was cooled to room temperature and concentrated. The residue was taken up in water, which was then acidified to pH 6 with acetic acid. The aqueous phase was extracted with EtOAc (2×20 ml) before the combined organic fractions were concentrated and the residue was triturated with EtOAc and the title compound was filtered off and dried in a vacuum oven to give a white solid (13 mg, 0.03 mmol). δH (d₆DMSO, 400 MHz): 8.52 (1H, d), 8.50 (1H, dd), 7.92-7.86 (2H, m), 7.73 (1H, d), 7.54-7.49 (3H, m), 7.44-7.35 (3H, m), 3.18 (2H, s), 3.05-2.96 (4H, m), 2.85-2.79 (4H, m); MS (ES-): $C_{27}H_{22}F_3N_3O_3$ requires 493; found 492 [M-H⁺].

EXAMPLE 26

4-[7-(5-{3-Chloro-4-[(1-methylethyl)oxy]phenyl}-1,2,4-oxadiazol-3-yl)-1,2,4,5-tetrahydro-3H-3-benzazepin-3-yl]butanoic acid

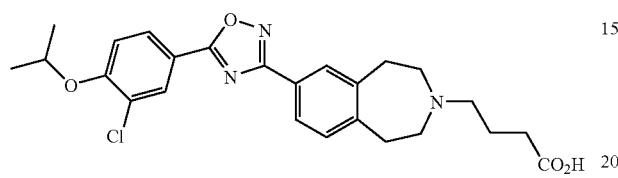

A solution of ethyl 4-[7-(5-{3-chloro-4-[(1-methylethyl)oxy]phenyl}-1,2,4-oxadiazol-3-yl)-1,2,4,5-tetrahydro-3H-3-benzazepin-3-yl]butanoate (Preparation 50) (100 mg, 0.201 mmol) in ethanol (6 ml) was stirred at room temp and sodium hydroxide (1.5 ml, 3.00 mmol) added. The reaction mixture was stirred at room temperature for 90 mins and was then acidified with acetic acid to pH 5, and the mixture concentrated in vacuo. The resultant residue was dissolved in EtOAc (~30 ml) and water (~30 ml) and the layers partitioned, the aqueous was re-extracted with EtOAc (~20 ml) and the combined organics were passed through a phase separation cartridge and the solvent reduced in vacuo. The residue was purified by trituration with methanol, the solid filtered and dried on the sinter to yield the title compound (30 mg, 0.061 mmol, 30% yield). δH (d₆DMSO, 400 MHz): 8.19 (1H, s), 8.11 (1H, d), 7.79-7.90 (2H, m), 7.44 (1H, d), 7.34 (1H, d), 4.89 (1H, sept), 3.46-3.24 (2H, hidden under H₂O peak), 3.01-2.93 (4H, m), 2.68-2.59 (4H, m), 2.28 (2H, t), 1.70 (2H, quintet) 1.37 (6H, d). MS (ES): $C_{25}H_{28}{}^{35}ClN_3O_4$ requires 469; found 470 [M+H]⁺.

EXAMPLE 27

4-[7-(5-{3-cyano-4-[(1-methylethyl)oxy]phenyl}-1,2,4-oxadiazol-3-yl)-1,2,4,5-tetrahydro-3H-3-benzazepin-3-yl]butanoic acid hydrochloride

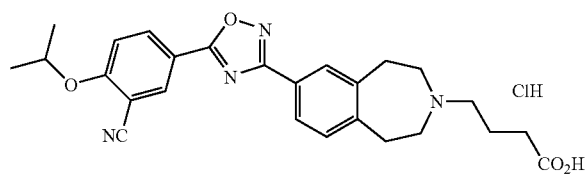

A solution of ethyl 4-[7-(5-{3-cyano-4-[(1-methylethyl)oxy]phenyl}-1,2,4-oxadiazol-3-yl)-1,2,4,5-tetrahydro-3H-3-benzazepin-3-yl]butanoate (Preparation 51) (218 mg, 0.446 mmol) in ethanol (6 ml) was stirred at room temp and sodium hydroxide (2 ml, 4.00 mmol) added. The reaction mixture was stirred at room temperature for 90 minutes and was then acidified with acetic acid to pH 5, and the mixture concentrated in vacuo. The resultant residue was dissolved in EtOAc (~30 ml) and water (~30 ml) and the layers partitioned, the aqueous was re-extracted with EtOAc (~20 ml) and the combined organics were passed through a phase separation cartridge and the solvent reduced in vacuo. The residue was purified by addition of 10 drops of 2M HCl in ether, followed by trituration with ether, the solid filtered and dried on the sinter and then under vacuum at 60° C. to yield the title compound (68 mg, 0.130 mmol, 29% yield). δH (d₆DMSO, 400 MHz): 8.51 (1H, s), 8.40 (1H, d), 7.97 (1H, s), 7.93 (1H, d), 7.56 (1H, d), 7.47 (1H, d), 4.99 (1H, sept), 3.07-3.80 (10H, m), 2.35 (2H, t), 1.92-2.02 (2H, m), 1.39 (6H, d); MS (ES): $C_{26}H_{28}N_4O_4$ requires 460; found 461 [M+H]⁺.

EXAMPLE 28

4-(7-{5-[4-[(1-Methylethyl)oxy]-3-(trifluoromethyl) phenyl]-1,2,4-oxadiazol-3-yl}-1,2,4,5-tetrahydro-3H-3-benzazepin-3-yl)butanoic acid hydrochloride

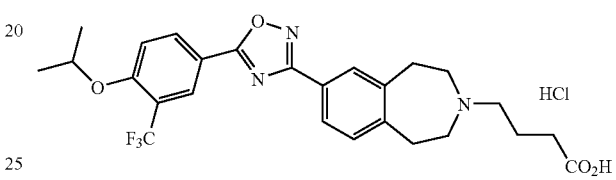

A solution of ethyl 4-(7-{5-[4-[(1-methylethyl)oxy]-3-(trifluoromethyl)phenyl]-1,2,4-oxadiazol-3-yl}-1,2,4,5-tetrahydro-3H-3-benzazepin-3-yl)butanoate (Preparation 52) (181 mg, 0.341 mmol) in ethanol (6 ml) was stirred at room temp and sodium hydroxide (2 ml, 4.00 mmol) added. The reaction mixture was stirred at room temperature for 90 minutes. The reaction mixture was acidified with acetic acid to pH 5, and the mixture concentrated in vacuo. The resultant residue was dissolved in ethyl acetate (~30 ml) and water (~30 ml) and the layers partitioned, the aqueous phase was re-extracted with ethyl acetate (~20 ml) and the combined organics were passed through a phase separation cartridge and the solvent reduced in vacuo.

The residue was purified by addition of 10 drops of 2M HCl in ether, followed by trituration with ether, the solid filtered and dried on the sinter to yield the title compound (119 mg, 0.21 mmol, 62% yield). δH (d₆DMSO, 400 MHz): 8.40 (1H, d), 8.32 (1H, s), 7.97 (1H, s), 7.94 (1H, d), 7.59 (1H, d), 7.45 (1H, d), 4.98 (1H, sept), 3.09-3.82 (10H, m), 2.35 (2H, t), 1.90-2.01 (2H, m), 1.36 (6H, d); MS (ES): $C_{26}H_{28}F_3N_3O_4$ requires 503; found 504 [M+H]⁺.

EXAMPLE 29

4-(7-{5-[2-(Trifluoromethyl)-4-biphenylyl]-1,2,4-oxadiazol-3-yl}-1,2,4,5-tetrahydro-3H-3-benzazepin-3-yl)butanoic acid hydrochloride

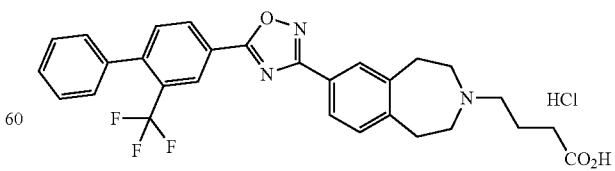

A solution of ethyl 4-(7-{5-[4-{(1E)-1-[(1Z)-1-propen-1-yl]-1,3-butadien-1-yl}-3-(trifluoromethyl)phenyl]-1,2,4-oxadiazol-3-yl}-1,2,4,5-tetrahydro-3H-3-benzazepin-3-yl)butanoate (Preparation 53) (277 mg, 0.504 mmol) in ethanol (6 ml) was stirred at room temperature and sodium hydroxide (2 ml, 4.00 mmol) added. The reaction mixture was stirred at room temperature for 90 minutes and was then acidified with acetic acid to pH 5, and the mixture concentrated in vacuo. The resultant residue was dissolved in EtOAc (~30 ml) and water (~30 ml) and the layers partitioned, the aqueous was re-extracted with EtOAc (~20 ml) and the combined organics were passed through a phase separation cartridge and the solvent reduced in-vacuo. The residue was purified by addition of 10 drops of 2M HCl in ether, followed by trituration with ether, the solid filtered and dried on the sinter and overnight under vacuum at 60° C. to yield the title compound (120 mg, 0.20 mmol, 41% yield). δH (d$_6$DMSO, 400 MHz): 8.53 (1H, s), 8.50 (1H, d), 8.01 (1H, s), 7.97 (1H, d), 7.75 (1H, d), 7.37-7.56 (6H, m), 3.14-3.41 (8H, m), 3.07 (2H, br s), 2.34 (2H, t), 1.87-1.99 (2H, m). MS (ES): $C_{29}H_{26}F_4N_3O_3$ requires 521; found 522 [M+H]$^+$.

EXAMPLE 30

2-(Methyloxy)-5-[3-(2,3,4,5-tetrahydro-1H-3-benzazepin-7-yl)-1,2,4-oxadiazol-5-yl]benzonitrile hydrochloride

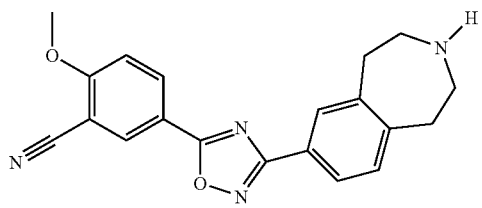

A solution of 1,1-dimethylethyl 7-{5-[3-cyano-4-(methyloxy)phenyl]-1,2,4-oxadiazol-3-yl}-1,2,4,5-tetrahydro-3H-3-benzazepine-3-carboxylate (Preparation 54) (280 mg, 0.627 mmol) in hydrochloric acid 4M solution in dioxane (5 ml, 20.00 mmol) and 1,4-dioxane (5 ml) was stirred at room temperature overnight. The reaction mixture was filtered and washed with dioxane (~5 ml), and the solid dried under vacuum to yield the title compound (177 mg, 0.393 mmol, 62.7% yield) as an off white solid. δH (d$_6$DMSO, 400 MHz): 8.99-9.31 (2H, m), 8.53 (1H, s), 8.46 (1H, d), 7.96 (1H, s), 7.93 (1H, d), 7.54 (1H, d), 7.46 (1H, d), 4.07 (3H, s), 3.09-3.31 (7H, m); MS (ES): $C_{20}H_{18}N_4O_2$ requires 346; found 347 [M+H]$^+$.

EXAMPLE 31

9-(5-{3-Chloro-4-[(1-methylethyl)oxy]phenyl}-1,2,4-oxadiazol-3-yl)-2,3,4,5-tetrahydro-1,4-benzoxazepine hydrochloride

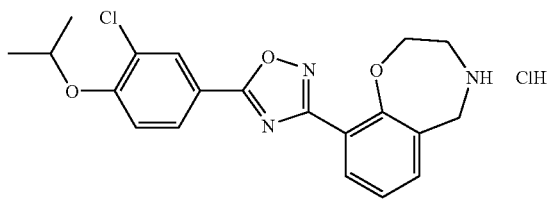

1,1-Dimethylethyl 9-(5-{3-chloro-4-[(1-methylethyl)oxy]phenyl}-1,2,4-oxadiazol-3-yl)-2,3-dihydro-1,4-benzoxazepine-4(5H)-carboxylate (Preparation 66) (320 mg, 0.658 mmol) was dissolved in 1,4-dioxane (1 ml) and treated with HCl (2 ml, 8.00 mmol) in 1,4-dioxane. The reaction mixture was left at RT for 1 hr, evaporated and then triturated with ether to give the title compound (180 mg) as a white solid. MS (ES): $C_{20}H_{20}{}^{35}ClN_3O_3$ requires 385; found 386 [M+H]$^+$.

The following compound was prepared by a similar method.

EXAMPLE 32

2-[(1-Methylethyl)oxy]-5-[3-(2,3,4,5-tetrahydro-1,4-benzoxazepin-9-yl)-1,2,4-oxadiazol-5-yl]benzonitrile hydrochloride

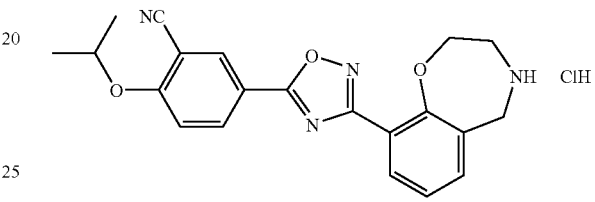

Prepared in a similar way to Example 31 from Preparation 67. MS (ES): $C_{21}H_{20}N_4O_3$ requires 376; found 377 [M+H]$^+$.

EXAMPLE 33

4-[9-(5-{3-Chloro-4-[(1-methylethyl)oxy]phenyl}-1,2,4-oxadiazol-3-yl)-2,3-dihydro-1,4-benzoxazepin-4(5H)-yl]butanoic acid

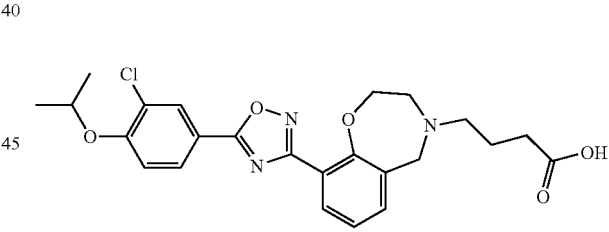

A solution of ethyl 4-[9-(5-{3-chloro-4-[(1-methylethyl)oxy]phenyl}-1,2,4-oxadiazol-3-yl)-2,3-dihydro-1,4-benzoxazepin-4(5H)-yl]butanoate (Preparation 68) (130 mg, 0.260 mmol) in ethanol was treated with sodium hydroxide (10.4 mg in 1 ml, 0.260 mmol). The reaction mixture was left standing at RT for 1 hour then evaporated. The resulting crude was partitioned between EtOAc/water, acidified with acetic acid, separated and the organivs dried over magnesium sulphate and evaporated. The title compound (61 mg) was obtained by trituration with ether as a white solid. δH (d$_6$DMSO, 400 MHz): 1.36 (6H, d), 1.69 (2H, m), 2.23 (2H, t), 2.43 (2H, t), 3.05 (2H, m), 3.86 (2H, s), 4.07 (2H, m), 4.88 (1H, m), 7.20 (1H, t), 7.43-7.49 (2H, m), 7.78 (1H, dd), 8.09 (1H, dd), 8.17 (1H, d), 12.10 (1H, br. s); MS (ES−): $C_{24}H_{26}{}^{35}ClN_3O_5$ requires 471; found 470 [M−H]$^+$.

EXAMPLE 33

Alternative Preparation

4-[9-(5-{3-Chloro-4-[(1-methylethyl)oxy]phenyl}-1,2,4-oxadiazol-3-yl)-2,3-dihydro-1,4-benzoxazepin-4(5H)-yl]butanoic acid

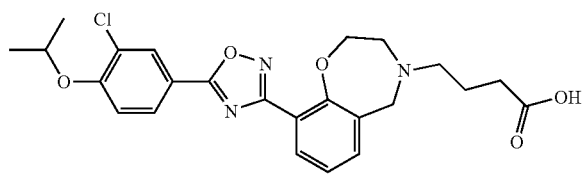

A solution of ethyl 4-[9-(5-{3-chloro-4-[(1-methylethyl)oxy]phenyl}-1,2,4-oxadiazol-3-yl)-2,3-dihydro-1,4-benzoxazepin-4(5H)-yl]butanoate (Preparation 68) (61.7 g, 123 mmol) in ethanol (600 ml) was treated with 2M sodium hydroxide (123 ml, 247 mmol) and the mixture stirred at room temperature overnight. The solvent was evaporated and the residue dissolved in water (1 liter). The aqueous solution was cooled in ice/water and treated slowly with glacial acetic acid (28.3 ml, 494 mmol). The resulting gum was stirred vigorously until a filterable solid was obtained which was then collected by filtration and washed with more water (2×500 ml). After sucking the pad dry the material was dissolved in a 95:5 mixture of dichloromethane/methanol and dried (sodium sulphate). The solvent was removed by evaporation and the resulting solid was triturated under diethyl ether (200 ml), collected by filtration, washed with diethyl ether and dried to give the title compound as a colourless solid (54 g).

MS (ES) $C_{24}H_{26}{}^{35}ClN_3O_6$ requires 471; found 472 [M+H]$^+$.

EXAMPLE 34

4-[9-(5-{3-Cyano-4-[(1-methylethyl)oxy]phenyl}-1,2,4-oxadiazol-3-yl)-2,3-dihydro-1,4-benzoxazepin-4(5H)-yl]butanoic acid

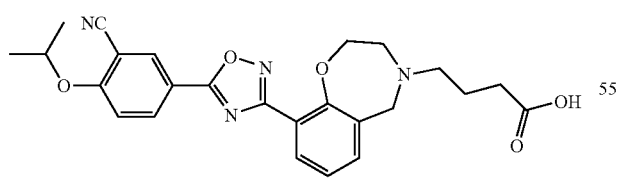

Prepared in a similar way to Example 33 from Preparation 69. δH (d$_6$DMSO, 400 MHz): 1.38 (6H, d), 1.69 (2H, m), 2.23 (2H, t), 2.43 (2H, t), 3.05 (2H, m), 3.86 (2H, s), 4.07 (2H, m), 4.98 (1H, m), 7.20 (1H, t), 7.47 (1H, dd), 7.54 (1H, d), 7.77 (1H, dd), 8.38 (1H, dd), 8.49 (1H, d), 12.10 (1H, br. s); MS (ES): $C_{26}H_{26}N_4O_6$ requires 462; found 463 [M+H]$^+$.

EXAMPLE 35

2-[(1-Methylethyl)oxy]-5-[3-(2,3,4,5-tetrahydro-1,4-benzoxazepin-7-yl)-1,2,4-oxadiazol-5-yl]benzonitrile hydrochloride

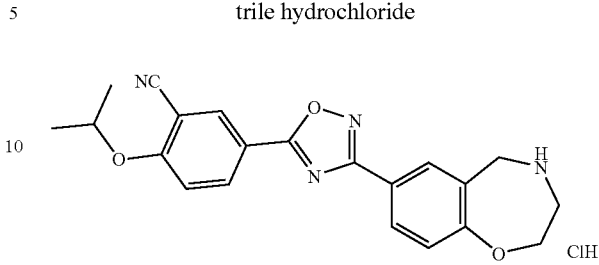

1,1-Dimethylethyl 7-(5-{3-cyano-4-[(1-methylethyl)oxy]phenyl}-1,2,4-oxadiazol-3-yl)-2,3-dihydro-1,4-benzoxazepine-4(5H)-carboxylate (Preparation 76) (0.410 g, 0.860 mmol) was dissolved in 1,4-dioxane (1 ml). Added HCl (1 ml, 4.00 mmol) in dioxane (4M) and stirred at R.T. for 2 hours. Added ether, filtered and dried in the oven under vacuum at R.T. to give 0.26 g of white solid. 50 mg was purified by MDAP to give the title compound (13 mg) as a cream solid. δH (MeOD, 400 MHz): 1.44 (6H, d), 3.63 (2H, m), 4.33 (2H, m), 4.52 (2H, s), 4.92 (1H, m), 7.30 (1H, d), 7.43 (1H, d), 8.15 (1H, dd), 8.21 (1H, d), 8.38 (1H, dd), 8.45 (1H, d); MS (ES): $C_{21}H_{20}N_4O_3$ requires 376; found 377 [M+H]$^+$.

EXAMPLE 36

7-(5-{3-chloro-4-[(1-methylethyl)oxy]phenyl}-1,2,4-oxadiazol-3-yl)-2,3,4,5-tetrahydro-1,4-benzoxazepine hydrochloride

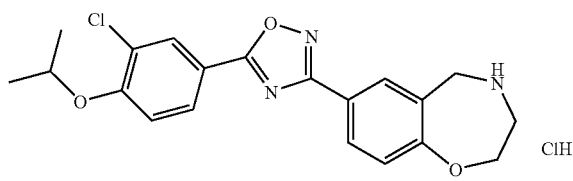

Prepared by a similar method to Example 35 from Preparation 77. δH (d$_6$DMSO, 400 MHz): 1.35 (6H, d), 3.51 (3H, m), 4.31 (2H, m), 4.82 (2H, s), 4.85 (1H, m), 7.23 (1H, d), 7.45 (1H, d), 7.97-8.12 (2H, m), 8.18 (2H, m); MS (ES): $C_{20}H_{20}{}^{35}ClN_3O_3$ requires 385; found 386 [M+H]$^+$.

EXAMPLE 37

3-[7-(5-{3-Cyano-4-[(1-methylethyl)oxy]phenyl}-1,2,4-oxadiazol-3-yl)-2,3-dihydro-1,4-benzoxazepin-4(5H)-yl]propanoic acid

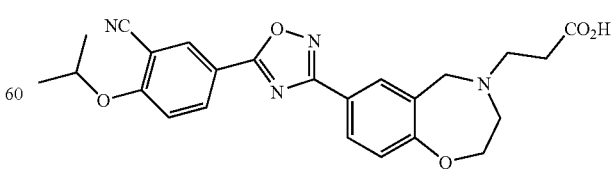

Ethyl 3-[7-(5-{3-cyano-4-[(1-methylethyl)oxy]phenyl}-1,2,4-oxadiazol-3-yl)-2,3-dihydro-1,4-benzoxazepin-4(5H)-yl]propanoate (Preparation 78) (0.092 g, 0.193 mmol) was dissolved in Ethanol (2 ml). Then 2N NaOH (1 ml, 2.000 mmol) was added and the reaction mixture left standing at RT for 2 hours. Ethanol was removed by evaporation and the resulting residue dissolved in EtOAc and water, acidified with acetic acid and the layers separated. Solid separated from the aqueous phase and was filtered off solid and dried under vacuum overnight at 50° C. to give the title compound (8 mg) as a white solid. δH (d$_6$DMSO, 400 MHz): 1.37 (6H, d), 2.38 (2H, t), 2.67 (2H, m), 3.03 (2H, m), 3.89 (2H, s), 4.07 (2H, m), 4.97 (1H, m), 7.14 (1H, d), 7.54 (1H, d), 7.89 (1H, dd), 7.98 (1H, d), 8.39 (1H, dd), 8.51 (1H, d); MS (ES): $C_{24}H_{24}N_4O_5$ requires 448; found 449 [M+H]$^+$.

EXAMPLE 38

3-[7-(5-{3-Chloro-4-[(1-methylethyl)oxy]phenyl}-1,2,4-oxadiazol-3-yl)-2,3-dihydro-1,4-benzoxazepin-4(5H)-yl]propanoic acid

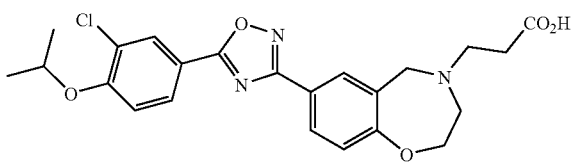

Prepared by a similar method to Example 37 from Preparation 79. δH (d$_6$DMSO, 400 MHz): 1.36 (6H, d), 2.43 (2H, t), 2.70 (2H, m), 3.04 (2H, m), 3.91 (2H, s), 4.07 (2H, m), 4.87 (1H, m), 7.14 (1H, d), 7.43 (1H, d), 7.89 (1H, dd), 7.99 (1H, d), 8.09 (1H, dd), 8.18 (1H, d); MS (ES): $C_{23}H_{24}{}^{35}ClN_3O_6$ requires 457; found 458 [M+H]$^+$.

EXAMPLE 39

4-[7-(5-{3-Cyano-4-[(1-methylethyl)oxy]phenyl}-1,2,4-oxadiazol-3-yl)-2,3-dihydro-1,4-benzoxazepin-4(5H)-yl]butanoic acid

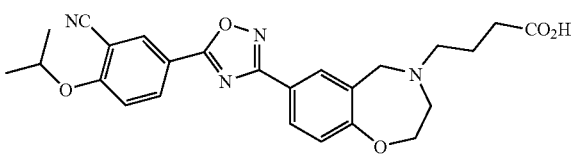

Ethyl 4-[7-(5-{3-cyano-4-[(1-methylethyl)oxy]phenyl}-1,2,4-oxadiazol-3-yl)-2,3-dihydro-1,4-benzoxazepin-4(5H)-yl]butanoate (Preparation 80) (0.084 g, 0.171 mmol) was dissolved in Ethanol (2 ml). Then 2N NaOH (1 ml, 2.000 mmol) was added and the reaction left standing at RT for 3 hours. Ethanol was removed by evaporation and the resulting residue dissolved in EtOAc and water, acidified with acetic acid and the phases separated. The organic phase was dried (MgSO$_4$), evaporated and triturated with ether. Drying under vacuum overnight at 50° C. yielded the title compound (22 mg) as a white solid. δH (d$_6$DMSO, 400 MHz): 1.37 (6H, d), 1.66 (2H, t), 2.22 (2H, t), 2.45 (2H, m), 3.01 (2H, m), 3.82 (2H, s), 4.07 (2H, m), 4.95 (1H, m), 7.14 (1H, d), 7.54 (1H, d), 7.89 (1H, dd), 7.96 (1H, d), 8.38 (1H, dd), 8.50 (1H, d); MS (ES): $C_{25}H_{26}N_4O_5$ requires 462; found 463 [M+H]$^+$.

EXAMPLE 40

4-[7-(5-{3-chloro-4-[(1-methylethyl)oxy]phenyl}-1,2,4-oxadiazol-3-yl)-2,3-dihydro-1,4-benzoxazepin-4(5H)-yl]butanoic acid

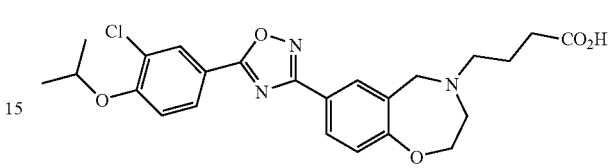

Prepared by hydrolysis of the ester, Preparation 81, using the method described for Example 37. δH (d$_6$DMSO, 400 MHz): 1.36 (6H, d), 1.68 (2H, t), 2.23 (2H, t), 2.45 (2H, m), 3.01 (2H, m), 3.87 (2H, s), 4.07 (2H, m), 4.87 (1H, m), 7.13 (1H, 7.43 (1H, d), 7.89 (1H, dd), 7.95 (1H, d), 8.09 (1H, dd), 8.52 (1H, d); MS (ES): $C_{24}H_{26}{}^{35}ClN_3O_6$ requires 471; found 472 [M+H]$^+$.

EXAMPLE 41

2-[(1-Methylethyl)oxy]-5-[3-(2,3,4,5-tetrahydro-1,4-benzoxazepin-8-yl)-1,2,4-oxadiazol-5-yl]benzonitrile

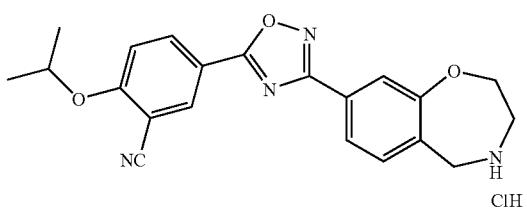

Prepared from Preparation 82 using a similar procedure to Example 35. MS (ES): $C_{21}H_{20}N_4O_3$ requires 376; found 377 [M+H]$^+$.

EXAMPLE 42

4-[8-(5-{3-cyano-4-[(1-methylethyl)oxy]phenyl}-1,2,4-oxadiazol-3-yl)-2,3-dihydro-1,4-benzoxazepin-4(5H)-yl]butanoic acid

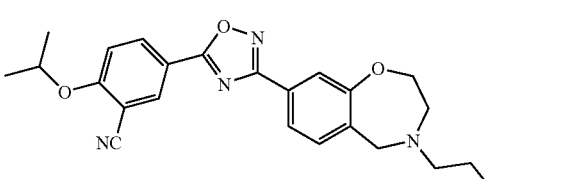

Prepared from Preparation 83 using the method described in Example 15. δH (d$_6$DMSO, 400 MHz): 1.38 (6H, d), 1.69 (2H, m), 2.21 (2H, t), 2.42 (2H, t), 3.02 (2H, m), 3.84 (2H, s), 4.06 (2H, m), 4.97 (1H, m), 7.44 (1H, d), 7.54 (1H, d), 7.61 (1H, d), 7.71 (1H, dd), 8.39 (1H, dd), 8.50 (1H, d), 12.10 (1H, br.s); MS (ES): $C_{26}H_{26}N_4O_5$ requires 462; found 463 [M+H]$^+$.

EXAMPLE 43

5-[9-(5-{3-Cyano-4-[(1-methylethyl)oxy]phenyl}-1,2,4-oxadiazol-3-yl)-2,3-dihydro-1,4-benzoxazepin-4(5H)-yl]pentanoic acid

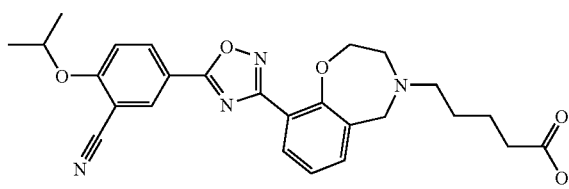

2M sodium hydroxide (0.347 mL, 0.694 mmol) was added to a stirred solution of ethyl 5-[9-(5-{3-cyano-4-[(1-methylethyl)oxy]phenyl}-1,2,4-oxadiazol-3-yl)-2,3-dihydro-1,4-benzoxazepin-4(5H)-yl]pentanoate (Preparation 93) (70 mg, 0.139 mmol) in ethanol (5 mL) and the mixture was heated to 60° C. overnight. The reaction mixture was allowed to cool to room temperature and the solvent evaporated. The residue was diluted with water, acidified with 2M hydrochloric acid and extracted with ethyl acetate. The organic phase was washed with water, dried and evaporated to give the product as an off white solid (20 mg).

δH (400 MHz, CDCl$_3$). 1.47 (6h, d), 1.59-1.70 (4H, m), 2.3 (2H, t), 2.61 (2H, t), 3.25-3.29 (2H, m), 4.05 (2H, s), 4.24-4.28 (2H, m), 4.79 (1H, m), 7.12 (1H, d), 7.20 (1H, dd), 7.39 (1H, d), 7.95 (1H, d), 8.30 (1H, dd), 8.43 (1H, s).

MS (ES) $C_{26}H_{28}N_4O_5$ requires 476 Found 477 [M+H]$^+$.

EXAMPLE 44

[9-(5-{3-Cyano-4-[(1-methylethyl)oxy]phenyl}-1,2,4-oxadiazol-3-yl)-2,3-dihydro-1,4-benzoxazepin-4(5H)-yl]acetic acid

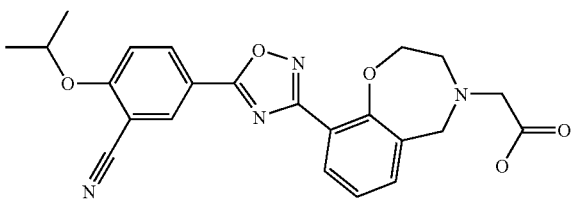

2M sodium hydroxide (0.54 ml, 1.08 mmol) was added to a stirred solution of ethyl [9-(5-{3-cyano-4-[(1-methylethyl)oxy]phenyl}-1,2,4-oxadiazol-3-yl)-2,3-dihydro-1,4-benzoxazepin-4(5H)-yl]acetate (Preparation 86) (100 mg, 0.216 mmol) in ethanol (10 ml) and the mixture was stirred at room temperature for 2 h. The solvent was evaporated before diluting with water, acidifying with 2M hydrochloric acid and extracting with ethyl acetate. The organic extract was washed with water, dried and evaporated to give the product as an off white solid (30 mg).

δH (400 MHz, D$_6$-DMSO). 1.39 (6H, d), 3.88-4.02 (2H, m), 4.09-4.13 (2H, m), 4.98 (1H, m), 7.43 (1H, d), 7.56 (1H, d), 7.82 (1H, d), 8.39 (1H, d), 8.50 (1H, s). Missing peaks obscured by water and residual solvent.

MS (ES) $C_{23}H_{22}N_4O_5$ requires 434 Found 435 [M+H]$^+$.

EXAMPLE 45

3-[9-(5-{5-Chloro-6-[(1-methylethyl)oxy]-3-pyridinyl}-1,2,4-oxadiazol-3-yl)-2,3-dihydro-1,4-benzoxazepin-4(5H)-yl]propanoic acid

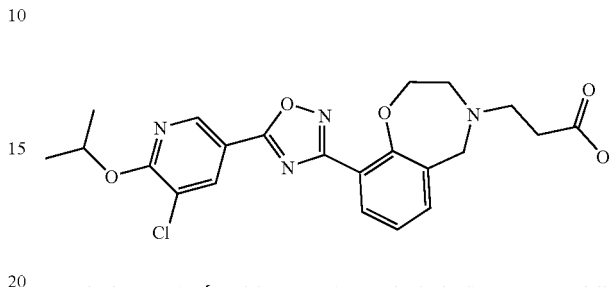

Ethyl 3-[9-(5-{5-chloro-6-[(1-methylethyl)oxy]-3-pyridinyl}-1,2,4-oxadiazol-3-yl)-2,3-dihydro-1,4-benzoxazepin-4(5H)-yl]propanoate (Preparation 91) (28 mg, 0.058 mmol) was dissolved in ethanol (5 ml). 2M sodium hydroxide (0.144 ml, 0.288 mmol) was added and the reaction mixture stirred at 60° C. for 4 hours. The solvent was evaporated and the reaction mixture diluted with water, neutralised with 2M hydrochloric acid and extracted with ethyl acetate. The organic phase was washed with water, dried and evaporated to give the product as a white solid (26 mg).

δH (400 MHz, CDCl$_3$). 1.46 (6H, d), 2.54 (2H, br t), 2.91 (2H, br t), 3.36 (2H, m), 4.12 (2H, s), 4.28 (2H, br m), 5.48 (1H, m), 7.21-7.29 (1H, m), 7.39 (1H, d), 8.00 (1H, d), 8.38 (1H, s), 8.88 (1H, s).

MS (ES) $C_{22}H_{23}{}^{35}ClN_4O_5$ requires 458 Found 459 [M+H]$^+$.

EXAMPLE 46

3-[9-(5-{3-Cyano-4-[(1-methylethyl)oxy]phenyl}-1,2,4-oxadiazol-3-yl)-2,3-dihydro-1,4-benzoxazepin-4(5H)-yl]propanoic acid

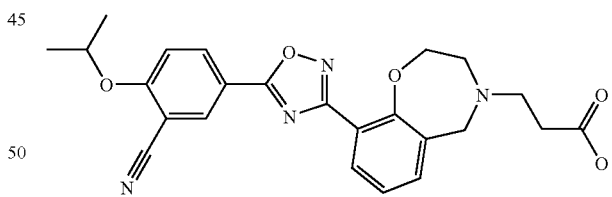

Ethyl 3-[9-(5-{3-cyano-4-[(1-methylethyl)oxy]phenyl}-1,2,4-oxadiazol-3-yl)-2,3-dihydro-1,4-benzoxazepin-4(5H)-yl]propanoate (Preparation 92) (40 mg, 0.084 mmol) was dissolved in ethanol (5 ml). 2M sodium hydroxide (0.210 ml, 0.420 mmol) was added and the reaction mixture stirred at 60° C. for 4 hours. The solvent was evaporated, then the reaction mixture was diluted with water, neutralised with 2M hydrochloric acid and extracted with ethyl acetate. The organic phase was washed with water, dried and evaporated to give the product as a colourless solid (16 mg).

δH (400 MHz, CDCl$_3$). 1.47 (6H, d), 2.56 (2H, br t), 2.92 (2H, br t), 3.34-3.39 (2H, m), 4.13 (2H, br s), 4.25-4.31 (2H, m), 4.79 (1H, m), 7.13 (1H, d), 7.20-7.28 (1H, m), 7.40 (1H, d), 8.00 (1H, d), 8.33 (1H, d), 8.42 (1H, s).

MS (ES) $C_{22}H_{24}N_4O_5$ requires 448 Found 449 [M+H]$^+$.

EXAMPLE 47

3-[9-(5-{3-Chloro-4-[(1-methylethyl)oxy]phenyl}-1,2,4-oxadiazol-3-yl)-2,3-dihydro-1,4-benzoxazepin-4(5H)-yl]propanoic acid

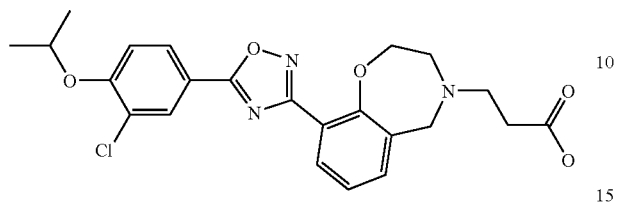

Ethyl 3-[9-(5-{3-chloro-4-[(1-methylethyl)oxy]phenyl}-1,2,4-oxadiazol-3-yl)-2,3-dihydro-1,4-benzoxazepin-4(5H)-yl]propanoate (Preparation 88) (60 mg, 0.123 mmol) was dissolved in ethanol (5 ml). 2M sodium hydroxide (0.309 ml, 0.617 mmol) was added and the reaction mixture was stirred at 60° C. for 4 h. The solvent was evaporated then the reaction mixture was diluted with water and neutralised with 2M hydrochloric acid and extracted with ethyl acetate. The organic phase was washed with water, dried and evaporated to give the product as a colourless solid (27 mg).

$\delta$H (400 MHz, D$_6$-DMSO). 1.36 (6H, d), 2.42 (2H, br t), 2.65-2.70 (2H, m), 3.90 (2H, s), 4.04-4.09 (2H, m), 4.88 (1H, m), 7.21 (1H, dd), 7.44 (1H, d), 7.51 (1H, d), 7.79 (1H, d), 8.09 (1H, d), 8.17 (1H, s).

MS (ES) $C_{23}H_{24}{}^{35}ClN_3O_6$ requires 457 Found 458 [M+H]$^+$.

EXAMPLE 48

2-[(1-Methylethyl)oxy]-5-[3-(2,3,4,5-tetrahydro-1H-3-benzazepin-7-yl)-1,2,4-oxadiazol-5-yl]-3-pyridinecarbonitrile formate

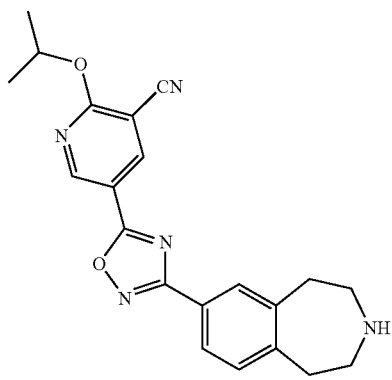

1,1-Dimethylethyl 7-(5-{5-cyano-6-[(1-methylethyl)oxy]-3-pyridinyl}-1,2,4-oxadiazol-3-yl)-1,2,4,5-tetrahydro-3H-3-benzazepine-3-carboxylate (Preparation 95) (224 mg, 0.471 mmol) in dichloromethane (1 ml) was treated with 4M HCl in dioxan (5 ml, 20.0 mmol). The colourless solution was left at room temperature over the week-end to give a colourless precipitate. The reaction mixture was concentrated, triturated with ether and dried. The crude product was treated with DMSO:MeOH (1:1; 1.9 ml), the mixture filtered and the filtrate purified by MDAP. The title compound was obtained as a formate salt (55 mgs), $\delta$H (400 MHz, d$_6$DMSO), 1.41 (6H, d), 3.07-3.20 (4H, m), 5.51 (1H, m), 7.42 (1H, d), 7.88 (1H dd), 7.91 (1H, d), 8.24 (1H, s), 8.98 (1H, d) and 9.20 (1H, d); MS (ES) $C_{21}H_{21}N_5O_2$ requires 375; found 376[M+H]$^+$.

EXAMPLE 49

7-(5-{5-Chloro-6-[(1-methylethyl)oxy]-3-pyridinyl}-1,2,4-oxadiazol-3-yl)-2,3,4,5-tetrahydro-1H-3-benzazepine hydrochloride

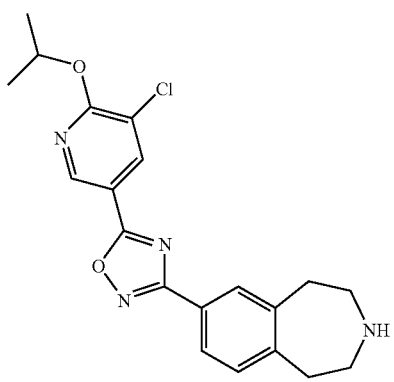

1,1-Dimethylethyl 7-(5-{5-chloro-6-[(1-methylethyl)oxy]-3-pyridinyl}-1,2,4-oxadiazol-3-yl)-1,2,4,5-tetrahydro-3H-3-benzazepine-3-carboxylate (Preparation 96) (305 mg, 0.629 mmol) in dichloromethane (2 mL) at room temperature was treated with trifluoroacetic acid (1 ml, 12.98 mmol) and the mixture stirred for 1 hr. The reaction mixture was concentrated and the residue partitioned between 2M NaOH and ethyl acetate. The ethyl acetate extract was washed with brine, dried and concentrated to a colourless gum which slowly crystallized, to give the title compound free base (229 mgs).

A portion of the free base (37 mg) was dissolved in methanol (0.5 ml) and treated with excess HCl in methanol (1.25M; 0.4 ml). The solution was evaporated to give the title compound as a colourless solid (42 mgs).

$\delta$H (400 MHz, d$_6$DMSO), 1.39 (6H, d), 3.21 (8H, d), 5.45 (1H, m), 7.45 (1H, d), 7.91 (1H, dd), 7.95 (1H, d), 8.55 (1H, d), 8.92 (1H, d) and 9.33 (2H, br s); MS (ES) $C_{20}H_{21}{}^{35}ClN_4O_2$ requires 384; found 385 [M+H]$^+$.

EXAMPLE 50

4-[7-(5-{5-Chloro-6-[(1-methylethyl)oxy]-3-pyridinyl}-1,2,4-oxadiazol-3-yl)-1,2,4,5-tetrahydro-3H-3-benzazepin-3-yl]butanoic acid

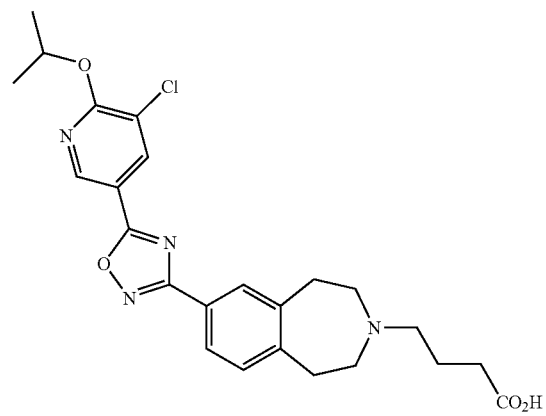

A suspension of ethyl 4-[7-(5-{5-chloro-6-[(1-methylethyl)oxy]-3-pyridinyl}-1,2,4-oxadiazol-3-yl)-1,2,4,5-tetrahydro-3H-3-benzazepin-3-yl]butanoate (Preparation 97) (185 mg, 0.371 mmol) in ethanol (3 ml), was treated with 2M sodium hydroxide (0.556 ml, 1.11 mmol) at room temperature overnight to give a colourless precipitate. A further 1-2 mls of ethanol was added and the temperature was raised to 50° C. to complete the reaction. Acetic acid (0.07 ml, 1.22 mmol) was added to the solution and the mixture concentrated. The resultant oily residue was treated with water (ca 3 ml) then stirred at room temperature for 1-2 hr and filtered. The solid was washed with water, then dissolved in methanol and the solvent evaporated. The resultant solid was dried overnight in vacuo at ca 60° C. to give the title compound (153 mgs).

$\delta$H (400 MHz, $d_6$DMSO), 1.39 (6H, d), 1.69 (2H, m) 2.26 (2H, t), 2.47 (2H, t), 2.61 (4H, br s), 2.95 (4H, br m), 5.45 (1H, m), 7.34 (1H, d), 7.80-7.85 (2H, m), 8.53 (1H, d) and 8.90 (1H, d); MS (ES) $C_{24}H_{27}{}^{35}ClN_4O_4$ requires 470; found 471 [M+H]$^+$.

Membrane Preparation for S1P1 GTPγS Assay

For membrane preparations all steps were performed at 4° C. Rat hepatoma cells stably expressing the human S1P1 receptor or Rat Basophilic Leukaemia cells (RBL) stably expressing human S1P3 receptor were grown to 80% confluency before being harvested into 10 ml Phospho-Buffered Saline (PBS) and centrifuged at 1200 rpm for 5 minutes. After removal of the supernatant, the pellet was re-suspended and cells were homogenised within a glass Waring blender for 2 bursts of 15 secs in 200 mls of buffer (50 mM HEPES, 1 mM leupeptin, 25 µg/ml bacitracin, 1 mM EDTA, 1 mM PMSF, 2 µM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

Alternative Membrane Preparation for S1P1 GTPγS Assay

All steps were performed at 4° C. Cells were homogenised within a glass Waring blender for 2 bursts of 15 secs in 200 mls of buffer (50 mM HEPES, 1 mM leupeptin, 25 µg/ml bacitracin, 1 mM EDTA, 1 mM PMSF, 2 µM pepstatin A). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and pepstatin A. The material was then forced through a 0.6 mm needle, made up to the required volume, (usually ×4 the volume of the original cell pellet), aliquoted and stored frozen at −80° C.

S1P1 GTPγS Assay

Human S1P1 rat hepatoma membranes (1.5 µg/well) were adhered to a wheatgerm agglutinin (WGA)-coated scintillation proximity assay (SPA) beads (0.125 mg/well) in assay buffer (HEPES 20 mM, $MgCl_2$ 10 mM, NaCl 100 mM and pH adjusted to 7.4 using KOH 5M, GDP 10 µM FAC (final assay concentration) and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radioligand conc) made up in assay buffer was then added to agonist plates. The final assay cocktail (10.1 µl) was then centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Alternative Method for S1P1 GTPγS Assay $S_1P_1$ expressing RH7777 membranes (1.5 µg/well) membranes (1.5 µg/well) were homogenised by passing through a 23 G needle. These were then adhered to WGA-coated SPA beads (0.125 mg/well) in assay buffer (HEPES 20 mM, $MgCl_2$ 10 mM, NaCl 100 mM and pH adjusted to 7.4 using KOH 5M). GDP 10 µM FAC and saponin 90 µg/ml FAC were also added After 30 minutes precoupling on ice, the bead and membrane suspension was dispensed into white Greiner polypropylene LV 384-well plates (5 µl/well), containing 0.1 µl of compound. 5 µl/well [$^{35}$S]-GTPγS (0.5 nM for $S_1P_1$ or 0.3 nM for $S_1P_3$ final radioligand concentration) made in assay buffer was then added to the plates. The final assay cocktail (10.1 µl) was then sealed, spun on a centrifuge, then read immediately on a Viewlux instrument.

Exemplified compounds of the invention had a pEC50>5, many had a pEC50>7. Examples 6, 7, 8, 12, 18, 19, 21 to 29, 31 to 35, 37, 39, 41, 43, 47, 48 and 50 had a pEC50>7. Examples 7, 21, 23, 24 and 26 to 28 had a pEC50≦3.

S1P3 GTPγS Assay

S1P3 membranes from rat basophilic leukaemia cells (RBL-2H3)(1.5 µg/well) were adhered to WGA-coated SPA beads (0.125 mg/well) in assay buffer (HEPES 20 mM, $MgCl_2$ 3 mM, NaCl 100 mM and pH adjusted to 7.4 using KOH 5M), GDP 10 µM FAC and saponin 90 µg/ml FAC was also added).

After 30 minutes pre-coupling on ice the bead and membrane suspension was dispensed into a white Greiner polypropylene LV384-well plate (5 µl/well), containing 0.1 µl of the compound. 5 µl/well [$^{35}$S]-GTPγS (0.5 nM final radioligand conc) made up in assay buffer was then added to agonist plates. The final assay cocktail (10.1 µl) was centrifuged at 1000 rpm for 5 minutes then read immediately on a Viewlux reader.

All test compounds were dissolved in DMSO at a concentration of 10 mM and were prepared in 100% DMSO using a 1 in 4 dilution step to provide 11 point dose response curves. The dilutions were transferred to the assay plates ensuring that the DMSO concentration was constant across the plate for all assays.

All data was normalized to the mean of 16 high and 16 low control wells on each plate. A four parameter curve fit was then applied.

Alternative Method for S1P3 GTPγS Assay $S_1P_3$ expressing RBL membranes (1.5 µg/well) were homogenised by passing through a 23 G needle. These were then adhered to WGA-coated SPA beads (0.125 mg/well) in assay buffer (HEPES 20 mM, $MgCl_2$ 10 mM, NaCl 100 mM and pH adjusted to 7.4 using KOH 5M). GDP 10 µM FAC and saponin 90 m/ml FAC were also added After 30 minutes precoupling on ice, the bead and membrane suspension was dispensed into white Greiner polypropylene LV 384-well plates (5 µl/well), containing 0.1 µl of compound. 5 µl/well [$^{35}$S]-GTPγS (0.5 nM for $S_1P_1$ or 0.3 nM for $S_1P_3$ final radioligand concentration) made in assay buffer was then added to the plates. The final assay cocktail (10.1 μl) was then sealed, spun on a centrifuge, then read immediately on a Viewlux instrument.

Exemplified compounds had a pEC50<6, many had a pEC50<5. Examples 1 to 5, 8 to 14, 16, to 22, 26, 30 to 34, 36, 37, 39 to 41, 43 to 50 had a pEC50≦55.

The invention claimed is:
1. A compound of formula (I) or a pharmaceutically acceptable salt thereof:

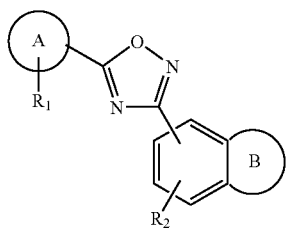

(I)

A is phenyl or a 5 or 6-membered heteroaryl ring;
$R_1$ is up to two substituents independently selected from halogen, $C_{(1-3)}$alkoxy, $C_{(1-3)}$fluoroalkyl, cyano, optionally substituted phenyl, $C_{(1-3)}$fluoroalkoxy, $C_{(1-6)}$alkyl and $C_{(3-6)}$cycloalkyl;
$R_2$ is hydrogen, halogen or $C_{(1-4)}$alkyl;
B is a 7 membered saturated ring selected from the following:

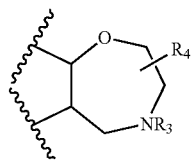

(b)

$R_3$ is hydrogen or $(CH_2)_{1-4}CO_2H$;
$R_4$ is hydrogen or $C_{(1-3)}$alkyl optionally interrupted by oxygen.

2. A compound of formula (I) or claim 1 or a pharmaceutically acceptable salt thereof, wherein:
A is phenyl or pyridinyl; and/or
$R_1$ is up to two substituents independently selected from chloro, isopropoxy and cyano; and/or
$R_2$ is hydrogen; and/or
B is (b); and/or
$R_3$ is hydrogen or $(CH_2)_{1-4}CO_2H$; and/or
$R_4$ is hydrogen.

3. A compound according to claim 1 selected from:
8-(5-{3-Chloro-4-[(1-methylethyl)oxy]phenyl}-1,2,4-oxadiazol-3-yl)-2,3,4,5-tetrahydro-1,4-benzoxazepine;
3-[8-(5-{3-Chloro-4-[(1-methylethyl)oxy]phenyl}-1,2,4-oxadiazol-3-yl)-2,3-dihydro-1,4-benzoxazepin-4(5H)-yl]propanoic acid
4-[8-(5-{3-Chloro-4-[(1-methylethyl)oxy]phenyl}-1,2,4-oxadiazol-3-yl)-2,3-dihydro-1,4-benzoxazepin-4(5H)-yl]butanoic acid;
[8-(5-{3-Chloro-4-[(1-methylethyl)oxy]phenyl}-1,2,4-oxadiazol-3-yl)-2,3-dihydro-1,4-benzoxazepin-4(5H)-yl]acetic acid;
9-(5-{3-chloro-4-[(1-methylethyl)oxy]phenyl}-1,2,4-oxadiazol-3-yl)-2,3,4,5-tetrahydro-1,4-benzoxazepine;
2-[(1-methylethyl)oxy]-5-[3-(2,3,4,5-tetrahydro-1,4-benzoxazepin-9-yl)-1,2,4-oxadiazol-5-yl]benzonitrile;
4-[9-(5-{3-Chloro-4-[(1-methylethyl)oxy]phenyl}-1,2,4-oxadiazol-3-yl)-2,3-dihydro-1,4-benzoxazepin-4(5H)-yl]butanoic acid;
4-[9-(5-{3-cyano-4-[(1-methylethyl)oxy]phenyl}-1,2,4-oxadiazol-3-yl)-2,3-dihydro-1,4-benzoxazepin-4(5H)-yl]butanoic acid;
2-[(1-methylethyl)oxy]-5-[3-(2,3,4,5-tetrahydro-1,4-benzoxazepin-7-yl)-1,2,4-oxadiazol-5-yl]benzonitrile;
3-[7-(5-{3-cyano-4-[(1-methylethyl)oxy]phenyl}-1,2,4-oxadiazol-3-yl)-2,3-dihydro-1,4-benzoxazepin-4(5H)-yl]propanoic acid;
3-[7-(5-{3-chloro-4-[(1-methylethyl)oxy]phenyl}-1,2,4-oxadiazol-3-yl)-2,3-dihydro-1,4-benzoxazepin-4(5H)-yl]propanoic acid;
4-[7-(5-{3-cyano-4-[(1-methylethyl)oxy]phenyl}-1,2,4-oxadiazol-3-yl)-2,3-dihydro-1,4-benzoxazepin-4(5H)-yl]butanoic acid;
4-[7-(5-{3-chloro-4-[(1-methylethyl)oxy]phenyl}-1,2,4-oxadiazol-3-yl)-2,3-dihydro-1,4-benzoxazepin-4(5H)-yl]butanoic acid;
2-[(1-methylethyl)oxy]-5-[3-(2,3,4,5-tetrahydro-1,4-benzoxazepin-8-yl)-1,2,4-oxadiazol-5-yl]benzonitrile;
4-[8-(5-{3-cyano-4-[(1-methylethyl)oxy]phenyl}-1,2,4-oxadiazol-3-yl)-2,3-dihydro-1,4-benzoxazepin-4(5H)-yl]butanoic acid;
5-[9-(5-{3-Cyano-4-[(1-methylethyl)oxy]phenyl}-1,2,4-oxadiazol-3-yl)-2,3-dihydro-1,4-benzoxazepin-4(5H)-yl]pentanoic acid;
[9-(5-{3-Cyano-4-[(1-methylethyl)oxy]phenyl}-1,2,4-oxadiazol-3-yl)-2,3-dihydro-1,4-benzoxazepin-4(5H)-yl]acetic acid;
3-[9-(5-{5-Chloro-6-[(1-methylethyl)oxy]-3-pyridinyl}-1,2,4-oxadiazol-3-yl)-2,3-dihydro-1,4-benzoxazepin-4(5H)-yl]propanoic acid;
3-[9-(5-{3-Cyano-4-[(1-methylethyl)oxy]phenyl}-1,2,4-oxadiazol-3-yl)-2,3-dihydro-1,4-benzoxazepin-4(5H)-yl]propanoic acid;
3-[9-(5-{3-Chloro-4-[(1-methylethyl)oxy]phenyl}-1,2,4-oxadiazol-3-yl)-2,3-dihydro-1,4-benzoxazepin-4(5H)-yl]propanoic acid;
and pharmaceutically acceptable salts thereof.

4. A pharmaceutical composition comprising a compound according to claim 1.

5. A method of treatment of lupus erythematosis which comprises administering to the sufferer a therapeutically safe and effective amount of a compound of formula (I) of claim 1 or a pharmaceutically acceptable salt thereof.

* * * * *